United States Patent
Russell et al.

(10) Patent No.: US 9,539,338 B2
(45) Date of Patent: Jan. 10, 2017

(54) POLYMER-BASED PROTEIN ENGINEERING METHODS TO RATIONALLY TUNE ENZYME ACTIVITY, PH-DEPENDENCE AND STABILITY

(71) Applicants: Alan J. Russell, Gibsonia, PA (US); Richard R. Koepsel, Pittsburgh, PA (US); Chad Cummings, Pittsburgh, PA (US); Hironobu Murata, Pittsburgh, PA (US)

(72) Inventors: Alan J. Russell, Gibsonia, PA (US); Richard R. Koepsel, Pittsburgh, PA (US); Chad Cummings, Pittsburgh, PA (US); Hironobu Murata, Pittsburgh, PA (US)

(73) Assignees: Carnegie Mellon University, Pittsburgh, PA (US); University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 14/785,868

(22) PCT Filed: Apr. 22, 2014

(86) PCT No.: PCT/US2014/035033
§ 371 (c)(1),
(2) Date: Oct. 21, 2015

(87) PCT Pub. No.: WO2014/176279
PCT Pub. Date: Oct. 30, 2014

(65) Prior Publication Data
US 2016/0101190 A1    Apr. 14, 2016

Related U.S. Application Data

(60) Provisional application No. 61/854,321, filed on Apr. 22, 2013, provisional application No. 61/961,098, filed on Oct. 3, 2013.

(51) Int. Cl.
| | |
|---|---|
| A61K 47/48 | (2006.01) |
| C08F 289/00 | (2006.01) |
| C08H 1/00 | (2006.01) |
| A61K 38/48 | (2006.01) |

(52) U.S. Cl.
CPC ..... *A61K 47/48176* (2013.01); *A61K 38/4826* (2013.01); *A61K 47/48769* (2013.01); *C08F 289/00* (2013.01); *C08H 1/00* (2013.01); *C12Y 304/21001* (2013.01)

(58) Field of Classification Search
CPC .............. A61K 47/48176; A61K 47/48769; A61K 38/4826; C12Y 304/21001; C08F 289/00; C08H 1/00
See application file for complete search history.

(56) References Cited

U.S. PATENT DOCUMENTS

| | | |
|---|---|---|
| 5,639,633 A | 6/1997 | Callstrom et al. |
| 5,998,588 A | 12/1999 | Hoffman et al. |
| 2007/0123646 A1 | 5/2007 | Lele et al. |
| 2007/0219330 A1* | 9/2007 | Haddleton ............ C07C 233/07 526/217 |
| 2007/0276088 A1 | 11/2007 | Maynard et al. |
| 2011/0091957 A1* | 4/2011 | Lele ................. A61K 47/48176 435/188 |

FOREIGN PATENT DOCUMENTS

WO    WO 2013/028756 A1    2/2013

OTHER PUBLICATIONS

Venkataraman, S., et al.; Macromolecules, 2006, p. 9661-9664.*
Limer, A., et al.; Macromolecules, 2006, p. 1353-1358.*
Written Opinion of the International Searching Authority for International Application No. PCT/US2014/035033 mailed Aug. 28, 2014.
International Search Report for International Application No. PCT/US2014/035033 mailed Aug. 28, 2014.
International Preliminary Report on Patentability for International Application No. PCT/US2014/035033 issued Oct. 27, 2015.
Alconcel, S., et al., "FDA-approved poly(ethylene blycol)-protein conjugate drugs,". *Polym ChemUk* 2011, 2, pp. 1442-1448.
Arotcarena, M., et al., "Switching the Inside and the Outside of Aggregates of Water-Soluble Block Copolymers with Double Termoresponsivity," *J. Am. Chem. Soc.* 2002, 124, pp. 3787-3793.
Averick, S., et al., "Preparation of Cationic Nanogels for Nucleic Acid Delivery," *Biomacromolecules* 2012, 13, pp. 3445-3449.
Averick, et al., "ATRP under Biologically Relevant Conditions: Grafting from a Protein," ACS Macro Lett. 2011, 1, 6-10.
Baldwin, R., "How Hofmeister Ion Interactions Affect Protein Stability*," *Biophys J* 1996, 71, pp. 2056-2063.
Benns, J., et al., " pH-Sensitive Cationic Polymer Gene Delivery Vehicle: N-Ac-poly(L-histidine)- graft-poly(L-lysine) Comb Shaped Polymer," *Bioconjugate Chem* 2000, 11, pp. 637-645.
Boyer, C., et al., "Well-Defined Protein-Polymer Conjugates via in Situ RAFT Polymerization," J. Am. Chem. Soc. 2007, 129, pp. 7145-7154.
Brittain, W. J., et al., "A Structural Definition of Polymer Brushes," *Polym. Sci.: Part A: Polym. Chem.* 2007, 45, 3505-3512.
Callahan, D., et al., "Triple Stimulus-Responsive Polypeptide Nanoparticles That Enhance Intratumoral Spatial Distribution," *Nano Lett.* 2012, 12, pp. 2165-2170.
Charles, M., "Soluble-Insoluble Enzyme Catalysts," *Biotech. Bioeng.* 1974, 16, pp. 1553-1556.

(Continued)

*Primary Examiner* — Robert Jones, Jr.
(74) *Attorney, Agent, or Firm* — K&L Gates LLP

(57) ABSTRACT

Using a novel water-soluble, active ester amide-containing functionalized controlled radical polymerization initiator, stimuli responsive polymers have been grown from the surface of a protein, exemplified by chymotrypsin or any protein having surface amino acids that will covalently bind to the active ester amide-containing functionalized initiator. It is shown that changes in temperature or pH can change the conformation of the polymer surrounding the enzyme, which in turn enabled the rational tailoring of enzyme activity and stability. This method has afforded an increase in the activity and stability of the enzyme by an order of magnitude at pH's where the enzyme is usually inactive or unstable. Multimodal temperature responsive protein-block copolymer conjugates are described.

39 Claims, 29 Drawing Sheets

(56) References Cited

OTHER PUBLICATIONS

Chen, C., et al., "Quaternary Ammonium Functionalized Poly(propylene imine) Dendrimers as Effective Antimicrobials: Structure-Activity Studies,"*Biomacromolecules*2000, 1, pp. 473-480.
Chen, J., et al., "Polymer-protein conjugates: II. Affinity precipitation separation of human immunogammaglobulbiny a poly(Wisopropylacrylamide-) protein A conjugate," *Biomaterials* 1990, 11, pp. 631-634.
Chen, L., et al., "Effects of polyelectrolyte complexation on the UCST of zwitterionic polyer," *Polymer* 2000, 41, pp. 141-147.
Chilkoti, a., "Targeted drug delivery by thermally responsive polymers," *Adv Drug Deliver Rev* 2002, 54, pp. 613-630.
Ciampolini, M., et al., "Five-Coordinated High-Spin Complexes of Bivalent Cobalt, Nickel, and Copper with Tris(2-dime thylaminoe thyl)amine," *Inorg. Chem.* 1966, 5, pp. 41-44.
De, P. et al., "Temperature-Regulated Activity of Responsive Polymer-Protein Conjugates Prepared by Grafting-from via RAFT Polymerization," B. S. *J. Am. Chem. Soc.* 2008, 130, pp. 11288-11289.
Dinndorf, P., et al., "FDA Drug Approval Summary: Pegaspargase (Oncaspar®) for the First-Line Treatment of Children with Acute Lymphoblastic Leukemia (ALL)," Oncologist 2007, 12, pp. 991998.
Dong, Z., et al., "Synthesis and responsive behavior of poly(N,N-dimethylaminoethyl methacrylate) brushes grafted on silica nanoparticles and their quaternized derivatives," *Polymer* 2012, 53, pp. 2074-2084.
Fuhrmann, G., et al., "Sustained gastrointestinal activity of dendronized polymer-enzyme conjugates," *Nat. Chem.* 2013, 5, pp. 582-589.
Gao, W. et al., "In situ growth of a stoichiometric PEG-like conjugate at a protein's N-terminus with significantly improvided pharmocoknetics," A. *Proc. Natl. Acad. Sci. USA* 2009, 106, pp. 1523115236.
*Handbook of Radical Polymerization*, K. Matyjaszewski and T. Davis, Ed., John Wiley & Sons, Inc. pub. (2002), pp. 553-555, 567.
Hedstrom, L., et al., "Serine Protease Mechanism and Specificity," *Chem. Rev.* 2002, 102, pp. 4501-4523.
Heredia, K., et al., "In Situ Preparation of Protein-"Smart" Polymer Conjugates with Retention of Bioactivity," *J Am Chem Soc* 2005, 127, pp. 16955-16960.
Hoffman, A., et al., "Conjugates of Stimuli-responsive polymers and proteins," *Prog. Polym. Sci.* 2007, 32,pp. 922-932.
Huang, J., et al., "Nonleaching Antibacterial Glass Surfaces via "Grafting Onto": The Effect of the Number of Quaternary Ammonium Groups on Biocidal Activity," *Langmuir* 2008, 24, pp. 6785-6795.
Keefe, A. et al., "Poly(zwitterionic)protein conjugates offer increased stability without sacrificing binding affinity or bioactivity," *Nat Chem* 2012, 4, pp. 59-63.
Kulkarni, S., et al., "Controlling the Aggregation of Conjugates of Streptavidin with Smart Block Copolymers Prepared via the RAFT Copolymerization Technique," *Biomacromolecules* 2006, 7, pp. 2736-2741.
Kulkarni, S., et al., "Reversible Meso-Scale Smart Polymer-Protein Particles of Controlled Sizes," Bioconjugate Chem. 2004, 15, pp. 747-753.
Kumar, A., et al., "Overview of the Stability of α-Chymotrypsin in Different Solvent Media," *Chem. Rev.* 2012, 112, pp. 4283-4307.
Lackey, C. , et al., "Hemolytic Activity of pH-Responsive Polymer-Streptavidin Bioconjugates," Bioconjugate Chem. 1999, 10, pp. 401-405.
Larger, E. et al., "Pancreatic exocrine function in patients with diabetes," *Diabetic Medicine* 2012, 29, pp. 104710-54.
Lele, B., et al., "Synthesis of Uniform Protein-Polymer Conjugates," *Biomacromolecules* 2005, 6, pp. 3380-3387.
Li, H. , et al., "Block copolymer conjugates prepared by sequentially grafting from proteins via RAFT," *Polym. Chem.* 2011, 2, pp. 1531-1535.
Li et al., "Thermoresponsive Block Copolymer-Protein Conjugates Prepared by Grafting-from via Raft Polymerization", Macromol. Rapid Commun., 2011, 32, pp. 354-359.
Li et al., "Thermoresponsive Block Copolymer-Protein Conjugates Prepared by Grafting-from via RAFT Polymerization" Supporting Information for Macromol. Rapid Commun., 2011, 32, pp. 354-359.
Liu, J., et al., "In Situ Formation of Protein-Polymer Conjugates through Reversible Addition Fragmentation Chain Transfer Polymerization," *Angew. Chem., Int. Ed.* 2007, 46, pp. 3099-3103.
Lo Nostro, P, et al., "Hofmeister Phenomena: An Update on Ion Specificity in Biology," *Chem Rev* 2012, 112, pp. 2286-2322.
Magnusson, J., et al., "In Situ Growth of Side-Chain PEG Polymers from Functionalized Human Growth Hormone-A New Technique for Preparation of Enhanced Protein-Polymer Conjugates," *Bioconjugate Chem.* 2010, 21, pp. 671-678.
McDaniel, J., et al., "Actively targeting solid tumours with thermoresponsive drug delivery systems that respond to mild hyperthermia," Int. J. Hyperthermia. 2013, 29, pp. 501-510.
Naito, H., "Three-Dimensional Cardiac Tissue Engineering Using a Thermoresponsive Artificial Extracellular Matrix," *ASAIO J.* 2004, 50, pp. 344-348.
Nasongkla, N., et al., "Multifunctional Polymeric Micelles as Cancer-Targeted, MRI-Ultrasensitive Drug Delivery Systems," *Nano Lett* 2006, 6, pp. 2427-2430.
Nesbitt, A., et al., "Mechanism of action of certolizumab pegol (CDP870): in vitro comparison with other anti-tumor necrosis factor alpha agents," *Inflamm Bowel Dis* 2007, 13, pp. 1323-1332.
Nicolas, J., et al., "Fluorescently tagged polymer bioconjugates from protein derived macroinitiators," *Chem. Commun.* 2006, 46, pp. 4697-4699.
Nordwald, E., et al., "Stabilization of Enzymes in Ionic Liquids Via Modification of Enzyme Charge," *Biotechnol Bioeng* 2013, 110, pp. 2352-2360.
O'Sullivan, A. K., "Use of Peginterferon Alfa-2B in Chronic Hepatitis C Patients Failing Prior Therapy: A Cost-Effectiveness Analysis," *Value Health* 2008, 11, p. A437.
Paterova, J., et al., "Reversal of the Hofmeister Series: Specific Ion Effects on Peptides," *J Phys Chem B* 2013, 117, pp. 81508158.
Qi, Y., et al., "Sortase-Catalyzed Initiator Attachment Enables High Yield Growth of a Stealth Polymer from the C Therminus of a Protein," *Macromol. Rapid Commun.* 2013, 34, pp. 1256-1260.
Reineke, J., et al., "Can bioadhesive nanoparticles allow for more effective particle uptake from the small intestine?," *J. Controlled Release* 2013, 170, pp. 477-484.
Rodriguez-Martinez, J. A., et al., "Enzymatic activity and thermal stability of PEG-a-chymotrypsin conjugates," *Biotechnol. Lett.* 2009, 31, pp. 883-887.
Rodriguez-Martinez, J., et al., "Stabilization of a-Chymotrypsin Upon PEGylation Correlates With Reduced Structural Dynamics," *Biotechnol. Bioeng.* 2008, 101, pp. 1142-1149.
Russell, A., et al., "Rational Modification of enzyme catalysis by engineering surface charge," *Nature* 1987, 328, pp. 496-500.
Russell, A., et al., "Electrostatic Effects on Modification of Charged Groups in the Active Site Cleft of Subtilisin by Protein Engineering," *Mol. Biol.* 1987, 193, pp. 803-813.
Sandanaraj, B., et al., "Noncovalent Modification of Chymotrypsin Surface Using an Amphiphilic Polymer Scaffold: Implications in Modulating Protein Function," J Am Chem Soc 2005, 127, pp. 10693-10698.
Schild, H. G., "Poly(N-Isopropylacrylamide): Experiment, Theory and Application," *Prog. Polym. Sci.* 1992, 17, pp. 163-249.
Simakova, A., et al., "Aqueous ARGET ATRP," *Macromolecules* 2012, 45, pp. 6371-6379.
Sioud, M., et al., "Cationic liposome-mediated delivery of siRNAs in adult mice," *Biochemical and Biophysical Research Communications* 2003, 312, pp. 1220-1225.
Smith, R. S., et al., "Vascular Catheters with a Nonleaching Poly-Sulfobetaine Surface Modification Reduce Thrombus Formation and Microbial Attachment," *Sci. Transl.* Med. 2012, 4, pp. 1-10.
Strozyk, M. et al., "Protein/Polymer-Based Dual-Responsive Gold Nanoparticles with pH-Dependent Thermal Sensitivity," *Adv. Funct. Mater.* 2012, 22, pp. 1436-1444.
Su, J., et al. "Catechol Polymers for pH-Responsive, Targeted Drug Delivery to Cencer Cells," *J. Am. Chem. Soc.* 2011, 133, pp. 11850-11853.
Tsarevsky, N., et al., "Deactivation Efficiency and Degree of Control over Polymerization in ATRP in Protic Solvents," *Macromolecules* 2004, 37, pp. 9768-9778.

(56) References Cited

OTHER PUBLICATIONS

Turner, K., et al., "Stabilization of a supplemental digestive enzyme by post-translational engineering using chemically-activiated polyethylene glycol," *Biotechnol. Lett.* 2011, 33, pp. 617-621.

Uchida, E., et al., "Topography of Polymer Chains Grafted on a Polymer Surface Underwater," *Macromolecules* 1997, 30, pp. 5464-5469.

van de Wetering, P., et al., "A Mechanistic Study of the Hydrolytic Stability of Poly(2-(dimethylamino)ethyl methacrylate)," *Macromolecules*, 1998, 31, pp. 8063-8068.

Van Leemputten, E., et al., "Soluble-Insoluble Complex of Trypsin Immobilized on Acrolein-Acrylic Acid Copolymer," *Biotech. Bioeng.* 1976, 18, pp. 587-590.

Veronese, F. M., "Peptide and Protein PEGylation: a review of problems and solutions," *Biomaterials* 2001, 22, pp. 405-417.

Weaver, J., et al. "Synthesis and aqueous solution properties of a well-defined thermo-responsive schizophrenic diblock copolymer," *Chem. Commun.* 2002, pp. 2122-2123.

Wijmans, C., et al., "Polymer Brushes at Curved Surfaces," *Macromolecules* 1993, 26, pp. 72147224.

Xu, Q., et al., "Scalable method to produce biodegradable nanoparticles that rapidly penetrate human mucus," *J. Controlled Release* 2013, 170, pp. 279-286.

Yang, Z., et al., "Polyethylene gylcol-induced stabilization of subtilisin," *Enzyme Microb. Technol.* 1996, 18, pp. 82-89.

Yaşayan, G., et al., "Responsive hybrid block co-polymer conjugates of proteins-controlled architecture to modulate substrate specificity and solution behavior," *C. Polym. Chem.*, 2011, 2, pp. 1567-1578.

Zhang, Y., et al., "Interactions between macromolecules and ions: the Hofmeister series," *Current Opinion in Chemical Biology* 2006, 10, pp. 658-663.

Zhang, Y., et al., "Effects of Hofmeister Anions on the LCST of PNIPAM as a Function of Molecular Weight," *J. Phys. Chem. C* 2007, 111, pp. 8916-8924.

Zhang, Z., et al., "Polysulfobetaine-Grafted Surfaces as Environmentally Benign Ultralow Fouling Marine Coatings," *Langmuir* 2009, 25, pp. 13516-13521.

Zhou, P. et al., "Electrophoretic separation of DNA using a new matrix in uncoated capillaries," *J. Chromatography A* 2005, 1083, pp. 173-178.

Elmouelhi, N., et al., Biotechnology Bioengineering; Flynne, W. G., Ed.; Nova Science Publishers, Inc. New York, 2008, pp. 37-74, "Chapter 2—Building on What Nature Gave Us: Engineering Cell Glycosylation Pathways".

\* cited by examiner

Step 1: Immobilization of ATRP initiator
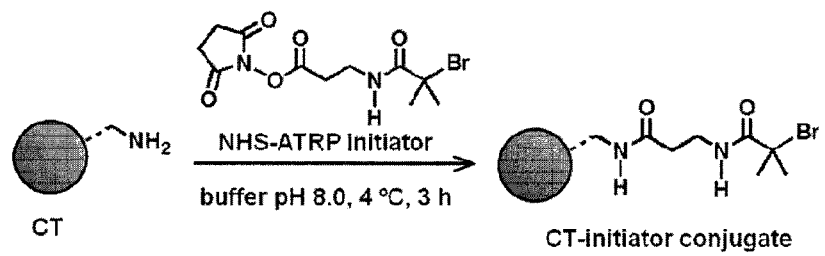
Step 2: ATRP of DMAEMA from CT-Initiator conjugate
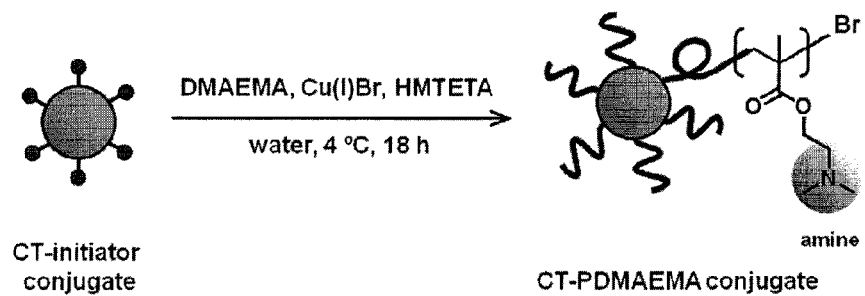
FIGURE 1

Table 6
Temperature dependence of chymotrypsin and bioconjugate activity, specificity and productivity for the hydrolysis of Suc-AAPF-pNA.

| Sample | $V_{max}$ [μM/sec] | $K_M$ [μM] | $k_{cat}$ [sec$^{-1}$] | $k_{cat}/K_M$ [sec$^{-1}$/μM] | $(K_M)x/(K_M)_{CT}$ | $(k_{cat})x/(k_{cat})_{CT}$ | $(k_{cat}/K_M)x/(k_{cat}/K_M)_{CT}$ |
|---|---|---|---|---|---|---|---|
| 5 °C | | | | | | | |
| Native CT | 0.37 ± 0.03 | 70.2 ± 18.4 | 9.32 ± 0.68 | 0.13 ± 0.04 | — | — | — |
| CT-Initiator | 0.34 ± 0.02 | 48.8 ± 13.8 | 8.62 ± 0.59 | 0.18 ± 0.05 | 0.69 | 0.92 | 1.33 |
| CT-pDMAPS | 0.27 ± 0.02 | 65.2 ± 17.2 | 6.84 ± 0.49 | 0.11 ± 0.03 | 0.93 | 0.73 | 0.79 |
| CT-pNIPAm | 0.26 ± 0.01 | 64.3 ± 13.0 | 6.55 ± 0.36 | 0.10 ± 0.02 | 0.92 | 0.70 | 0.77 |
| 25 °C | | | | | | | |
| Native CT | 1.10 ± 0.05 | 75.2 ± 12.6 | 27.4 ± 1.30 | 0.36 ± 0.06 | — | — | — |
| CT-Initiator | 1.14 ± 0.05 | 52.1 ± 8.99 | 28.5 ± 1.20 | 0.55 ± 0.10 | 0.69 | 1.04 | 1.50 |
| CT-pDMAPS | 0.82 ± 0.03 | 52.1 ± 7.13 | 20.5 ± 0.69 | 0.39 ± 0.06 | 0.69 | 0.75 | 1.08 |
| CT-pNIPAm | 0.87 ± 0.01 | 111 ± 5.16 | 21.7 ± 1.38 | 0.19 ± 0.02 | 1.48 | 0.79 | 0.53 |
| 40 °C | | | | | | | |
| Native CT | 1.72 ± 0.05 | 87.2 ± 8.20 | 43.0 ± 1.28 | 0.49 ± 0.05 | — | — | — |
| CT-Initiator | 2.00 ± 0.05 | 73.6 ± 6.52 | 50.0 ± 1.25 | 0.68 ± 0.06 | 0.84 | 1.16 | 1.38 |
| CT-pDMAPS | 1.31 ± 0.04 | 69.0 ± 7.57 | 32.8 ± 0.99 | 0.47 ± 0.05 | 0.79 | 0.76 | 0.96 |
| CT-pNIPAm | 0.56 ± 0.06 | 235 ± 53.0 | 13.9 ± 1.38 | 0.06 ± 0.01 | 2.70 | 0.32 | 0.12 |

Michaelis–Menten kinetic parameters were calculated at 5 °C, 25 °C, and 40 °C for native CT, CT-I, and each of the CT-polymer conjugates, $K_M$ and $V_{max}$ were calculated using EnzFitter software, $k_{cat}$ was calculated by dividing $V_{max}$ by the initial enzyme concentration.

FIGURE 26 ial Application Ser. No. 61/854,321 filed Apr. 22, 2013 and U.S. Provisional Application Ser. No. 61/961,098 filed Oct. 3, 2013, of which the contents of both are incorporated by reference in their entirety.

POLYMER-BASED PROTEIN ENGINEERING METHODS TO RATIONALLY TUNE ENZYME ACTIVITY, PH-DEPENDENCE AND STABILITY

PRIORITY

This application claims the benefit of U.S. Provisional Application Ser. No. 61/854,321 filed Apr. 22, 2013 and U.S. Provisional Application Ser. No. 61/961,098 filed Oct. 3, 2013, of which the contents of both are incorporated by reference in their entirety.

BACKGROUND

The covalent attachment of polymers to therapeutic proteins (such as the addition of poly(ethyleneglycol) (PEG) to interferon) has led to extensive commercial use. Since the advent of protein PEGylation in 1979 (Veronese, F. M. *Biomaterials* 2001, 22, 405), much of the research devoted to improving the efficacy of protein therapeutics has been focused on increasing circulation time and reducing immunogenicity. As of 2011, at least nine PEGylated protein drugs had been approved by the U.S. Food and Drug Administration (FDA) for treatment of diseases including Hepatitis C (O'Sullivan, A. K.; Buti, M.; Delong, K.; Prasad, M.; Sabater, F. J.; Esteban, R.; Weinstein, M. C. *Value Health* 2008, 11, A437), acute lymphoblastic leukemia (Dinndorf, P. A.; Gootenberg, J.; Cohen, M. H.; Keegan, P.; Pazdur, R. *Oncologist* 2007, 12, 991.), and Crohn's disease (Nesbitt, A.; Fossati, G.; Bergin, M.; Stephens, P.; Stephens, S.; Foulkes, R.; Brown, D.; Robinson, M.; Bourne, T. *Inflamm Bowel Dis* 2007, 13, 1323; Alconcel, S. N. S.; Baas, A. S.; Maynard, H. D. *Polym Chem-Uk* 2011, 2, 1442.). While PEGylation is a useful tool to hide protein based therapeutics from the immune system, and to increase size to slow elimination from the body, little additional specific functionality is added by PEGylation. In recent years, targeted drug delivery and drug carriers with responsive functionality (Chilkoti, A.; Dreher, M. R.; Meyer, D. E.; Raucher, D. *Adv Drug Deliver Rev* 2002, 54, 613; Su, J.; Chen, F.; Cryns, V. L.; Messersmith, P. B. *J Am Chem Soc* 2011, 133, 11850; Nasongkla, N.; Bey, E.; Ren, J.; Ai, H.; Khemtong, C.; Guthi, J. S.; Chin, S.-F.; Sherry, A. D.; Boothman, D. A.; Gao, J. *Nano Lett* 2006, 6, 2427) have been investigated to improve efficacy of current therapeutics.

Polymer conjugation to proteins can be completed using one of two methods: "grafting to" or "grafting from." In "grafting to," pre-synthesized, end functionalized polymers are coupled to accessible amino acid side chains or end termini on the protein surface. The "grafting-to" technique dominates the literature. The grafting site of a functionalized synthetic polymer to a protein surface through a coupling reaction is often a random process in which the density and site(s) of the grafted polymer cannot be controlled. Naturally, once a first polymer chain has "grafting-to" the protein surface steric hindrance will often prohibit further polymer binding to near-by sites on the protein surface, resulting in a low density of the grafting polymer. (Lele, B. S.; Murata, H.; Matyjaszewski, K.; Russell, A. J. *Biomacromolecules* 2005, 6, 3380-3387; Yang, Z.; Domach, M.; Auger, R.; Yang, F. X.; Russell, A. J. *Enzyme Microb. Technol.* 1996, 18, 82-89.) Although "Grafting to" techniques provide a wide range of polymerization reactions and monomers to select from, a large excess of polymer is often required to overcome steric limitations caused by coupled polymers. In addition, separation of protein-polymer conjugates from unreacted polymer can prove to be difficult when using the "grafting to" method.

Many pH-responsive polymers show a reversible phase transition between expanded and collapsed forms due to ionization and deionization of the side groups on the polymer that leads to alteration in hydrodynamic volume and solubility in aqueous media. Early studies on pH-responsive polymer-protein conjugates showed that conjugation of carboxylated polymers such as poly(acrylic acid) to proteins influenced the pH dependence of solubility and activity. (see Charles, M.; Coughlin, R. W.; Hasselberger, F. X. *Biotech. Bioeng.* 1974, 16, 1553-1556; Van Leemputten, E.; Horisberger, M. *Biotech. Bioeng.* 1976, 18, 587-590) Thermoresponsive polymers respond to changes in temperature and exhibit reversible transitions between collapsed and expanded forms at temperatures above and below their critical solution temperature. For example, poly(N-isopropylacrylamide) (pNIPAm) has a low critical solution temperature (LCST) around 32° C. in the aqueous solution. At temperatures above the LCST, pNIPAm becomes dehydrated and collapses into micelle-like particles which precipitate from solution. This property of temperature-responsive polymer-protein conjugates has been used to enhance purifications using pNIPAm-modified Protein A and monoclonal antibodies that were synthesized with the "grafting-to" approach. "Grafted-to" enzyme-pNIPAm conjugates are unpredictable however in that some enzymes exhibit modulated bioactivity but others do not.

In order to provide an alternative approach to synthesis of polymer-enzyme conjugates that would allow higher densities, and finer site control, a protein surface initiated "grafting from" technique was previously developed (Lele et al, *Biomacromolecules* 2005, 6, 3380-3387) This resulted in a higher density of polymer on the enzyme surface but because the initiator binding and polymerization were done in an organic solvent-water biphasic medium the recovery of activity was low and the density was still not optimal. (see also Heredia, K. L.; Bontempo, D.; Ly, T.; Byers, J. T.; Halstenberg, S.; Maynard, H. D. *J Am Chem Soc* 2005, 127, 16955)

"Grafting from" techniques initiate polymerization directly from the surface of proteins using controlled radical polymerization. Most often, either atom transfer radical polymerization (ATRP) (see Lele, B. S.; Murata, H.; Matyjaszewski, K.; Russell, A. J. *Biomacromolecules* 2005, 6, 3380; Nicolas, J.; San Miguel, V.; Mantovani, G.; Haddleton, D. M. *Chem. Commun.* 2006, 4697; Heredia, K. L.; Bontempo, D.; Ly, T.; Byers, J. T.; Halstenberg, S.; Maynard, H. D. *J. Am. Chem. Soc.* 2005, 127, 16955; Qi, Y.; Amiram, M.; Gao, W.; McCafferty, D. G.; Chilkoti, A. *Macromol. Rapid Commun.* 2013, 34, 1256; Gao, W.; Liu, W.; Mackay, J. A.; Zalutsky, M. R.; Toone, E. J.; Chilkoti, A. *Proc. Natl. Acad. Sci. U.S.A.* 2009, 106, 15231) or reversible-addition fragmentation chain transfer (RAFT) (Liu, J.; Bulmus, V.; Herlambang, D. L.; Barner-Kowollik, C.; Stenzel, M. H.; Davis, T. P. *Angew. Chem., Int. Ed.* 2007, 46, 3099; De, P.; Li, M.; Gondi, S. R.; Sumerlin, B. S. *J. Am. Chem. Soc.* 2008, 130, 11288) are used, because each provide low polydispersity indices (PDI), a large library of monomers, and biologically relevant reaction conditions (aqueous solvent and ambient temperature). In "grafting from," unreacted monomer is easily separated from the bioconjugate and high polymer density is achieved more easily due to the lack of steric limitations seen in "grafting to." One drawback to "grafting from" is the necessity to have vinyl monomers for radical polymerization. Thus, some polymers, such as PEG, must be slightly modified to use with the "grafting from" approach.

Another major limitation of the current "grafting-from" ATRP techniques for polymer based protein engineering is in the attachment or immobilization of an ATRP-initiator to the enzyme. Until recently most functionalized ATRP initiator compounds were insoluble or of low solubility in aqueous solution. Thus, immobilization of an ATRP initiator to a protein was performed in mixtures of water and organic solvents such as dichloromethane, methanol, DMF, or DMSO. (Nicolas, J.; San Miguel, V.; Mantovani, G.; Haddleton, D. M. *Chem. Commun.* 2006, 46, 4697-4699; Magnusson, J. P.; Bersani, S.; Salmaso, S.; Alexander, C.; Caliceti, P. *Bioconjugate Chem.* 2010, 21, 671-678; Ya şayan, G.; Saeed, A. O.; Fernández-Trillo, F.; Allen, S.; Davies, M. C.; Jangher, A.; Paul, A.; Thurecht, K. J.; King, S. M.; Schweins, R.; Griffiths, P. C.; Magnusson, J. P.; Alexander, C. *Polym. Chem.* 2011, 2, 1567-1578; Averick, S.; Simakova, A.; Park, S.; Konkolewicz, D.; Magenau, A. J. D.; Mehl, R. A.; Matyjaszewski, K. *ACS Macro Lett.* 2011, 1, 6-10.) Such mixtures often lead to inactivation and/or denaturation of enzymes during the immobilization reaction. Further, initiator immobilizations performed on chymotrypsin (CT) in a biphasic solution and on trypsin in 2% DMSO resulted in 21-50% and 46% occupation of available conjugation sites, respectively.

Techniques to synthesize protein-polymer conjugates have developed rapidly in recent years due to advancements in both protein and polymer science. One of the first, and still most common polymers to attach to proteins is poly (ethylene glycol) (PEG), (see Alconcel, S. N. S.; Baas, A. S.; Maynard, H. D. *Polym. Chem.* 2011, 2, 1442), which imparts stealth properties on the protein by reducing immunogenicity and increases in vivo stability by slowing renal clearance and degradation. However, this polymer does not add specific functionality to the protein and often results in reduced activity. (see Veronese, F. M. *Biomaterials* 2001, 22, 405) More recently, different polymers have been utilized to synthesize "smart conjugates" (see Hoffman, A. S.; Stayton, P. S. *Prog. Polym. Sci.* 2007, 32, 922 that respond to external stimuli such as pH (Lackey, C. A.; Murthy, N.; Press, O. W.; Tirrell, D. A.; Hoffman, A. S.; Stayton, P. S. *Bioconjugate Chem.* 1999, 10, 401; Strozyk, M. S.; Chanana, M.; Pastoriza-Santos, I.; Pérez-Juste, J.; Liz-Marzán, L. M. *Adv. Funct. Mater.* 2012, 22, 1436.). In addition, specific polymer choices for tailored applications, such as increased substrate affinity (Keefe, A. J.; Jiang, S. Y. *Nat. Chem.* 2012, 4, 60) have been reported. Polymer-based protein engineering refers to these tailored polymer conjugation applications that target problems that previously could only potentially be solved with molecular biology-dependent techniques.

Poly(sulfobetaine methacrylamide) (pSBAm) and poly (N-isopropylacrylamide) (pNIPAm) are two polymers that have been investigated for a wide range of chemical and biological applications. Specifically, pNIPAm can be used in applications for cardiac repair (Naito, H.; Takewa, Y.; Mizuno, T.; Ohya, S.; Nakayama, Y.; Tatsumi, E.; Kitamura, S.; Takano, H.; Taniguchi, S.; Taenaka, Y. *ASAIO J.* 2004, 50, 344), protein drug release, and biomolecule separations (Zhou, P.; Yu, S. B.; Liu, Z. H.; Hu, J. M.; Deng, Y. Z. *J. Chromatogr. A* 2005, 1083, 173). pSBAm is used frequently for non-fouling surface modification (Zhang, Z.; Finlay, J. A.; Wang, L.; Gao, Y.; Callow, J. A.; Callow, M. E.; Jiang, S. *Langmuir* 2009, 25, 13516; Smith, R. S.; Zhang, Z.; Bouchard, M.; Li, J.; Lapp, H. S.; Brotske, G. R.; Lucchino, D. L.; Weaver, D.; Roth, L. A.; Coury, A.; Biggerstaff, J.; Sukavaneshvar, S.; Langer, R.; Loose, C. *Sci. Transl. Med.* 2012, 4, 153ra132). Both pSBAm and pNIPAm respond to changes in temperature by predictable alterations in polymer folding. pNIPAm has a lower critical solution temperature (LCST), where above ~32° C. in deionized water the polymer experiences a reversible collapse, in which it becomes hydrophobic and dehydrated. (Schild, H. G. *Prog. Polym. Sci.* 1992, 17, 163.) pSBAm exhibits a similar, but opposite behavior known as upper critical solution temperature (UCST) phase transition. pSBAm UCST values are more dependent on molecular weight than the LCST of pNIPAm, but below a given temperature polymer chains collapse from a coil to globule orientation as they phase separate and become insoluble in aqueous media. (Chen, L.; Honma, Y.; Mizutani, T.; Liaw, D. J.; Gong, J. P.; Osada, Y. *Polymer* 2000, 41, 141.) Free block copolymers with both UCST and LCST properties have been reported previously (Arotcarena, M.; Heise, B.; Ishaya, S.; Laschewsky, A. *J. Am. Chem. Soc.* 2002, 124, 3787; Weaver, J. V. M.; Armes, S. P.; Butun, V. *Chem. Commun.* 2002, 2122), but protein-polymer conjugates are most often only synthesized with single temperature responsiveness imparted by homopolymer conjugation (Kulkarni, S.; Schilli, C.; Muller, A. H. E.; Hoffman, A. S.; Stayton, P. S. *Bioconjugate Chem.* 2004, 15, 747; Boyer, C.; Bulmus, V.; Liu, J. Q.; Davis, T. P.; Stenzel, M. H.; Barner-Kowollik, C. *J. Am. Chem. Soc.* 2007, 129, 7145). While block copolymers are sometimes conjugated to proteins with the "grafting to" approach, there are few reports of block copolymers being grown from proteins using "grafting from." Previously, Sumerlin and coworkers used "grafting from" to synthesize a block copolymer using two consecutive RAFT polymerizations from lysozyme (Li, H. M.; Li, M.; Yu, X.; Bapat, A. P.; Sumerlin, B. S. *Polym. Chem.* 2011, 2, 1531) and bovine serum albumin (Li, M.; Li, H. M.; De, P.; Sumerlin, B. S. *Macromol. Rapid Commun.* 2011, 32, 354.). Kulkarni et al. synthesized a block copolymer with modified temperature sensitivity, but used the "grafting to" process for protein conjugation (see Kulkarni, S.; Schilli, C.; Grin, B.; Muller, A. H. E.; Hoffman, A. S.; Stayton, P. S. *Biomacromolecules* 2006, 7, 2736).

SUMMARY OF THE INVENTION

The inventors hypothesized that if one could find a way to grow responsive polymers from the surface of a protein, for example, an enzyme, then one could influence the functionality of catalytically active proteins in a controlled reliable manner by polymer-based protein engineering (PBPE) as an alternative to site-directed mutagenesis.

In the "grafting-from" approach using the methods and macroinitiator described hereinto, a wide range of monomers can be used for conjugation and the molecular weight of the grafted polymer on the conjugate can be exquisitely controlled with a narrow polymer distribution. Thus, "grafting-from" bioconjugates can be rationally designed using the methods described herein, allowing structure-function relationships between the polymer and the protein to predict the functionality of the resulting covalent conjugate. One important variable that had heretofore been unresolved was the control of polymer density.

The various embodiments of the methods of the present invention permit the growth of polymer chains from the surface of proteins. In various embodiments, the polymer chains may be stimuli responsive polymers, such as pH- and temperature-responsive polymers, grown from the surface of proteins in order to tune the pH- and temperature-dependence of bioactivity. Controlled manipulation of the bioactivity of proteins, and in particular, enzymes, opens the door to a new class of biomolecules that may be used, for example, in therapeutic applications.

An embodiment of the composition may comprise a densely modified protein-polymer conjugate with a density of polymer chains per unit surface area exceeding one polymer chain per 20 nm² of protein surface area. The density may be greater than one polymer chain per 10 nm² of protein surface area or in some embodiments, densities between about one polymer chain per less than 20 nm² of protein surface area.

In this invention, a novel, water soluble, active ester-functionalized amide-containing controlled radical polymerization (CRP) initiator is designed and immobilized to the amines on the surface of a protein in aqueous solution. The CRP initiator comprises the general structure

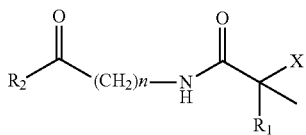

wherein

X is a halogen, such as Br, Cl, or F, or a chain transfer agent;

$R_1$ is H or alkyl;

$R_2$ is an active ester moiety; and n is an integer from 1 to 6.

The active ester moiety may be N-oxysuccinimde ester, nitrophenyl ester, pentahalophenyl ester wherein the halogen is F or Cl, 1-oxybenzotriazole ester, or 2-oxy-4,6-dimethyloxy-1,3,5-triazine ester. The chain transfer agent may be any suitable known chain transfer agent used in a RAFT polymerization procedure. See, for example, *Handbook of Radical Polymerization*, K. Matyjaszewski and T. Davis, Ed., John Wiley & Sons, Inc. pub. (2002), Section 12.4, incorporated herein by reference. Exemplary chain transfer agents of the general structure

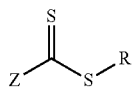

fall into four classes of thiocarbonylthio agents: (1) dithioesters, where Z is aryl or alkyl, (2) trithiocarbonates where Z is a substituted sulphur, (3) dithiocarbonates (xanthates), where Z is substituted oxygen, and (4) dithiocarbamates, where Z is substituted nitrogen.

In one example, the active ester-functionalized amide-containing CRP initiator is an N-2-bromo-2-methylpropanoyl-β-alanine N'-oxysuccinimide ester.

In various embodiments, the active ester-functionalized amide-containing CRP initiator is an NHS-functionalized ATRP initiator which may be immobilized to the surface reactive amino acid side chains of a protein, for example, an enzyme. In one embodiment, the active ester-functionalized amide-containing controlled radical polymerization (CRP) initiator may be immobilized to lysines on a serine protease α-chymotrypsin (CT) surface in aqueous solution. Herein, it is demonstrated that in various embodiments, the initiator occupied a plurality of the binding sites on the surface of the protein, and more particularly, a majority of binding sites, and of significance, occupied from about 85-100%, and in some embodiments, occupied all of the binding sites, or about 90% of the binding sites, or about 86% of the binding sites, and at least 85% of the binding sites on the surface of the enzyme, without significantly affecting enzyme activity.

In various embodiments, the method of the invention comprises immobilizing an active ester-functionalized amide-containing CRP initiator in an aqueous solution on each of a majority of amino binding sites on a protein surface to form a protein-initiator conjugate, isolating the protein-initiator conjugate, mixing a first group of monomers having one or more desired properties with the protein-initiator conjugate, polymerizing the monomers from the protein-initiator conjugate to grow a polymer under controlled radical polymerization conditions to form a protein-polymer conjugate; and, isolating the protein-polymer conjugate. The chain length of the polymers is controlled by adjusting the molar concentration of the first group of monomers added to the protein initiator conjugate to a desired amount.

The controlled radical polymerization conditions may include ATRP or RAFT polymerization procedures. If ATRP is the polymerization procedure of choice, then the functional group, X, in the active ester-functionalized amide-containing CRP initiator structure (I) above is preferably a halogen. If RAFT is the polymerization procedure of choice, then the functional group, X, in the initiator structure (I) above is a chain transfer agent.

The step of immobilizing the initiator may include mixing protein and the active ester-functionalized amide-containing CRP initiator in buffer, for example, at a pH of about 8 to 9, and stirring for a period of time sufficient to allow the formation of covalent bonds between the initiator and the plurality of amino binding sites. The step of isolating the protein-initiator conjugate may include removing unreacted and unattached compounds from the solution, by for example, passing the solution through a dialysis membrane. Similarly, the step of isolating the protein-polymer conjugate may be done by passing the mixture through a dialysis membrane under refrigeration for a period of time sufficient to remove catalyst and unreacted monomer. The method may further comprise the step of lyophilizing the protein-polymer conjugate.

The step of mixing the monomers with the protein-initiator conjugate under controlled radical polymerization conditions may include mixing under ATRP conditions, for example, mixing in buffer and removing oxygen from the mixture, adding a deoxygenated ligand to a separate aqueous copper catalyst solution, transferring the copper-ligand catalyst solution to the protein-initiator conjugate and monomer mixture, and stirring at 4-25° C. for a sufficient time to allow polymerization to proceed. Removing oxygen from the protein-initiator conjugate and monomer mixture may be done by bubbling Ar or $N_2$ through the mixture.

The protein may be an enzyme selected from the group consisting of chymotrypsin, lysozyme, β-Galactosidase, carbonic anhydrase, glucose oxidase, laccase, and acetylcholinesterase. Other proteins and enzymes or hormones may be used provided they have surface amino groups, such as surface lysine or cysteine groups available for covalent binding with the active ester of the active ester-functionalized amide-containing CRP initiator. Suitable surface amino groups include any amino acid residue having surface reactive amino acids that can covalently bind to the active ester of the amide-containing initiator. The structures of amino acids are well known. Those skilled in the art may determine suitable amino acid residues that can covalently bind to the active ester by reference to the literature.

The polymers used for the protein-polymer conjugate are preferably stimuli responsive polymers that respond to at least one stimulus. The stimulus may be one or both of pH and temperature. The polymer may also be one that changes the charge of the protein. The protein-polymer conjugate may be, for example, a chymotrypsin modified through high density attachment of thermo-responsive polymers.

In certain embodiments of the method described herein, the protein-polymer conjugate formed from the controlled radical polymerization may be a protein-homopolymer conjugate of different polymer chain lengths. Following the polymerization of the first group of monomers from the protein-initiator conjugate, the method may further include the steps of mixing a second group of monomers having one or more desirable properties with the protein-homopolymer conjugate under controlled radical polymerization conditions to form a block copolymer. In an exemplary embodiment, the block copolymer may be a dual temperature responsive enzyme-pSBAm-block-pNIPAm conjugate having different polymer chain lengths and molecular weights. In another exemplary embodiment, the protein may be, for example, an enzyme with a surface charge modified by growing cationic pQA from multiple sites on the surface of enzyme. In another exemplary embodiment, the polymers grown from the plurality of surface amino sites of the protein core may form a high density cationic polymer shell around the protein core.

The method described herein provides a macroinitiator comprising a water soluble active ester-functionalized amide-containing controlled radical polymerization initiator having the structure

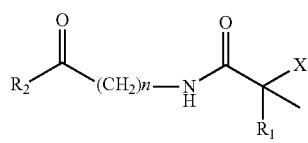

(I)

wherein X is a halogen, such as Br, F, or Cl, or a chain transfer agent; $R_1$ is H or alkyl; $R_2$ is an active ester moiety; and n is an integer from 1 to 6, covalently bound to each of a plurality of surface amino residues on a protein, such as lysine or cysteine residues, and in some embodiments, the N-terminal amino residue. The active ester-functionalized amide-containing CRP initiator may bind to at least 85% of the surface amino residues on the protein, and may also covalently bind to the N-terminus of the protein. Examples of the active ester moieties that may be used in the initiator are described above.

An embodiment of the method described herein provides a protein-polymer conjugate that comprises an enzyme core having surface amino residues covalently bound at each of at least a majority of the surface amino residues, and preferably at least 85% or more of the surface amino residues, to a stimuli responsive polymer grown from the surface of the enzyme under controlled radical polymerization conditions, such as ATRP or RAFT. Exemplary enzyme may be selected from the group consisting of chymotrypsin, lysozyme, β-Galactosidase, carbonic anhydrase, glucose oxidase, laccase, and acetylcholinesterase. Those skilled in the art will recognize that other proteins, for example, other enzymes, with free reactive amino acid side chains residues on one or both of the surface or the N-terminus, may be used in the method described herein. The polymer of the protein-polymer conjugate may form a block copolymer, or may form a cationic shell around the enzyme core.

In certain embodiments, the "grafting from" synthesis of a block copolymer may include carrying out two consecutive ATRP reactions from the surface of a protein. For example, temperature sensitive polymers, such as pSBAm and pNIPAm, may be grafted from the surface of chymotrypsin (CT) using two consecutive ATRP reactions.

Using polymer-based protein engineering (PBPE) with aqueous atom transfer radical polymerization (ATRP), three different molecular weight CT-pSBAm-block-pNIPAm bioconjugates were synthesized that responded structurally to both low and high temperature. In the block copolymer grown from the surface of the enzyme, upper critical solution temperature (UCST) phase transition was dependent on the chain length of the polymers in the conjugates, whereas lower critical solution temperature (LCST) phase transition was independent of molecular weight. Each CT-pSBAm-block-pNIPAm conjugate showed temperature dependent changes in substrate affinity and productivity when assayed from 0 to 40° C. In addition, these conjugates showed higher stability to harsh conditions, including temperature, low pH, and protease degradation. Indeed, the PBPE-modified enzyme was active for over eight hours in the presence of a stomach protease at pH 1.0. Using PBPE a dual zone shell surrounding each molecule of enzyme was created. The thickness of each zone of the shell was engineered to be separately responsive to temperature.

Atom transfer radical polymerization-based protein engineering of, for example, the enzyme chymotrypsin with a cationic polymer, such as poly(quaternary ammonium) may be used to tune the activity, stability, and inhibitor binding of the enzyme. Poly(quaternary ammonium), for example, was grown from the surface of the enzyme using atom transfer radical polymerization after covalent attachment of a protein reactive, water soluble NHS-amide-containing halo functionalized initiator, sometimes referred to herein for brevity as an ATRP initiator. This "grafting from" conjugation approach generated highly concentrated cationic ammonium ions around the biocatalytic core. After modification, bioactivity was increased at low pH relative to the activity of the native enzyme. In addition, substrate affinity was increased after conjugation over a wide range of pH's. The massively cationic chymotrypsin was also more stable at extremes of temperature and pH. Most interestingly, the methods allow rational control of the binding of two oppositely charged protease inhibitors, aprotinin and Bowman-Birk trypsin-chymotrypsin inhibitor from glycine max, to the cationic derivative of chymotrypsin.

Poly(2-(dimethylamino)ethyl methacrylate) (PDMAEMA) exhibits a phase transfer between super-hydrophilic and hydrophobic characteristics below and above its $pK_a$. The chains of PDMAEMA are expanded in aqueous solution when tertiary amine groups of PDMAEMA are protonated and hydrated below the $pK_a$. In contrast, the polymer chains are collapsed by deprotonation and dehydration of the amine group above the $pK_a$. There are also conformational changes in PDMAEMA below and above its Low Critical Solution Temperature (LCST). PDMAMEA is used herein as a model to determine how "grafted-from" stimuli-responsive protein-polymer conjugates can be controlled with environmental variables such as pH, temperature and solvent. Growing the polymer from the surface of CT, it was demonstrated by several examples that changes in temperature or pH can change predictably the conformation of the polymer surrounding the enzyme, which in turn enabled the rational tailoring of enzyme activity and stability. Using this method and approach, the activity and stability of CT has increased by an order of magnitude at pH's where the enzyme is usually inactive or unstable.

BRIEF DESCRIPTION OF THE DRAWINGS

FIG. 1 illustrates an overview of Polymer-based protein engineering (PBPE) using ATRP with DMAEMA and chymotrypsin.

and native CT (closed circle). The inset picture shows the hypothesized effect of electrostatic attraction and repulsion on inhibitor binding.

Figure 19:
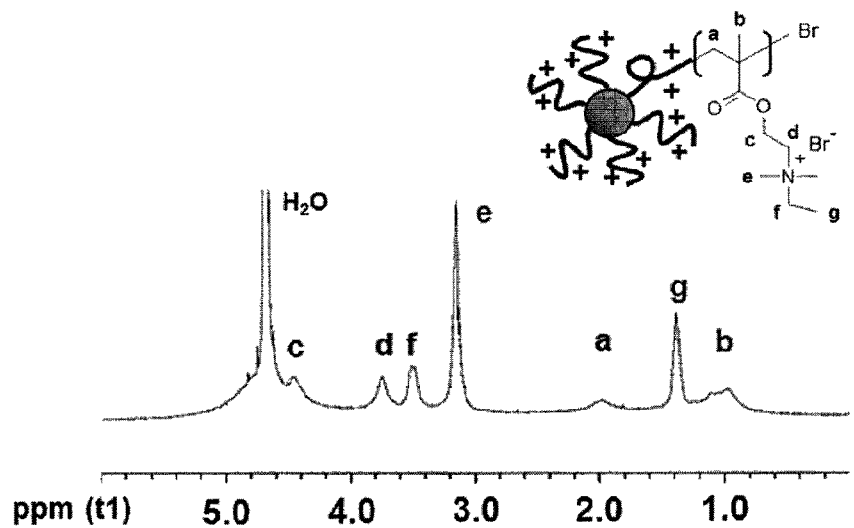

FIG. 19 shows the NMR spectra of chymotrypsin-pQA conjugates using CT-pQA$_{50}$ dissolved in D$_2$O (10 mg/mL). The NMR spectra peaks identifying correlating proton shifts are specified above.

Figure 20:
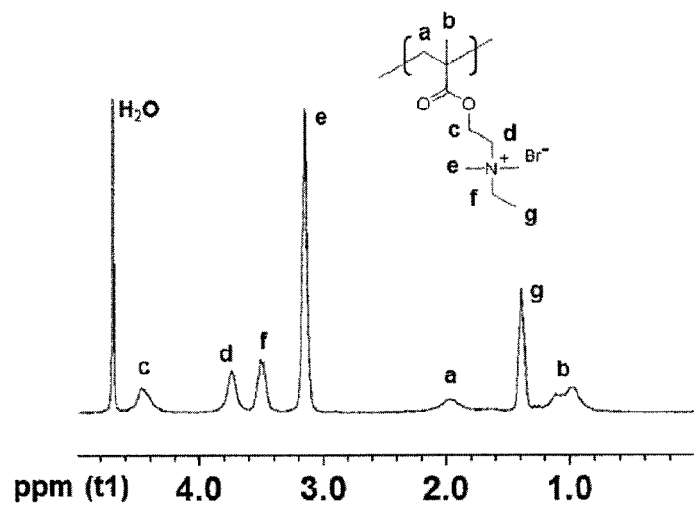

FIG. 20 shows the NMR spectra of pQA polymers cleaved from the surface of chymotrypsin using acid hydrolysis were determined using pQA$_{200}$ (10 mg/mL) in D$_2$O. Chymotrypsin-pQA conjugates were dissolved in 6 N HCl (10-20 mg/mL), followed by three freeze-pump-thaw cycles to remove air from the mixture. Conjugates were incubated at 110° C. for 24 hr. Dialysis filtering (MwCO 1000 Da) against DI water was used to remove digested enzyme and HCl from the solution.

Figure 21:
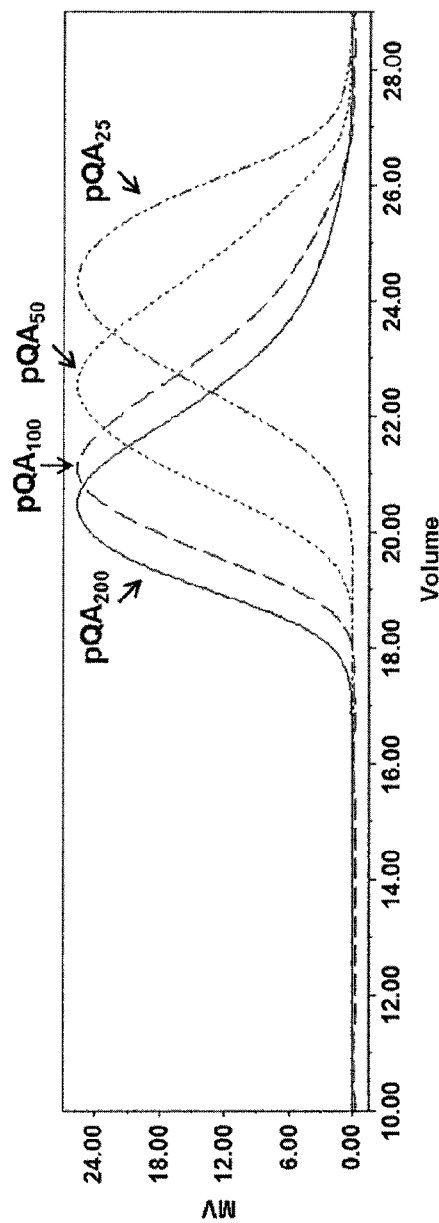

FIG. 21 represents the results of size exclusion chromatography (SEC) used to determine the molecular weight of pQA polymers cleaved from the surface of chymotrypsin using acid hydrolysis. Each of the four pQA conjugates was dissolved at 5 mg/mL using 0.1 M sodium phosphate buffer (pH 2) with 0.2 vol % TFA as the eluent. Samples were run at a flow rate of 1 mL/min. Poly(ethylene glycol) standards were used to determine the molecular weight.

FIGS. 22A and B show (A) Apparent K$_M$ and V$_{max}$ values were determined for native CT incubated with aprotinin protein inhibitor by monitoring enzyme catalyzed hydrolysis of Suc-AAPF-pNA after mixing inhibitor (0-0.49 µM), enzyme (39 nM), and substrate (0-750 µM) together at the same time. Apparent K$_M$ and V$_{max}$ values were calculated using EnzFitter by Michelis-Menten curve fitting of substrate against initial velocity plots. Values are shown in Table 11. (B) Secondary plots with calculated apparent K$_M$ and V$_{max}$ values were used to determine inhibition constants of aprotinin towards native chymotrypsin.

Figure 23:
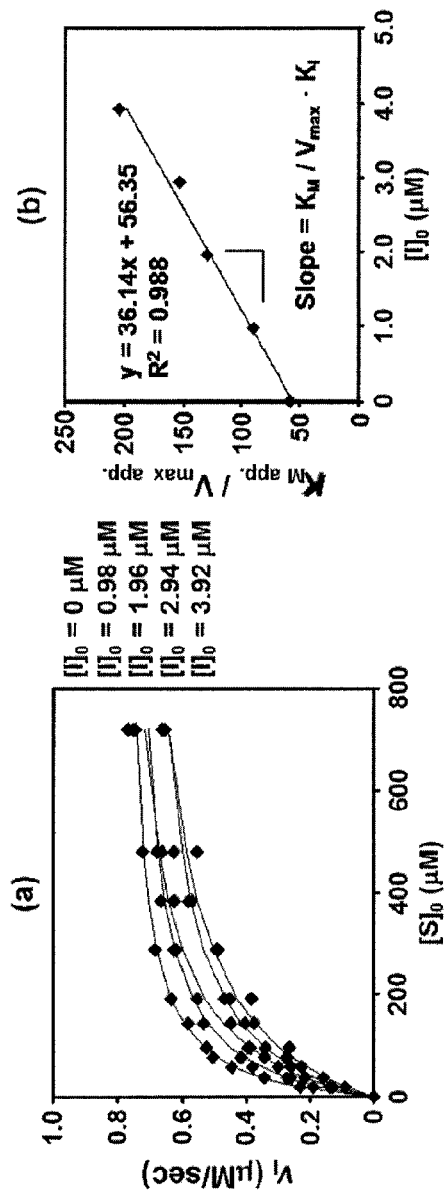

FIGS. 23A and B show (A) Substrate/initial velocity plots and (B) secondary plots to determine inhibitor constant for chymotrypsin-pQA$_{200}$ with aprotinin in 0.1 M sodium phosphate buffer (pH 8) at 25° C. The procedure used was the same as described above for aprotinin and native chymotrypsin.

FIGS. 24A and B show (A) Substrate/initial velocity plots and (B) secondary plots to determine inhibitor constant for native chymotrypsin with GM in 0.1 M sodium phosphate buffer (pH 8) at 25° C. The procedure used was the same as described above for aprotinin and native chymotrypsin except less inhibitor was used (0-0.294 µM).

Figure 25:
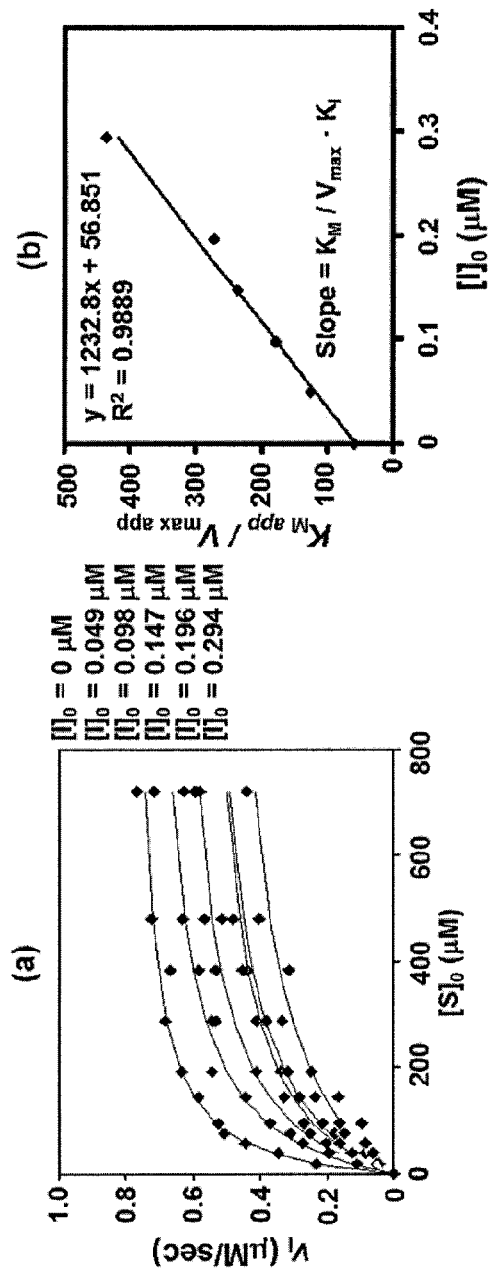

FIGS. 25A and B show (A) Substrate/initial velocity plots and (B) secondary plots to determine inhibitor constant for chyomtrypsin-pQA$_{200}$ with GM in 0.1 M sodium phosphate buffer (pH 8) at 25° C. The procedure used was the same as described above for aprotinin and native chymotrypsin except less inhibitor was used (0-0.294 µM).

FIG. 26 is a Table for Experimental Section II showing the temperature dependence of chymotrypsin and bioconjugate activity, specificity and productivity for the hydrolysis of Suc-AAPF-pNA.

Figure 27:
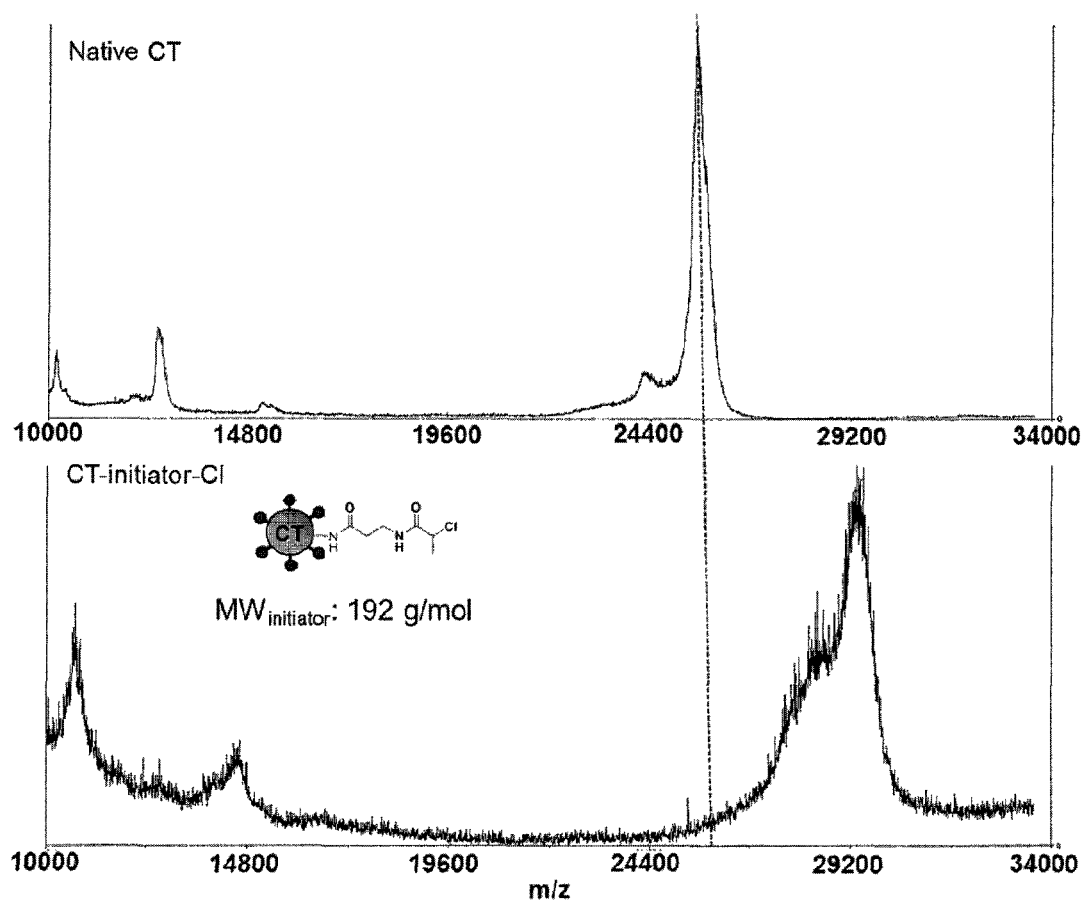

FIG. 27 shows the MALDI-TOF-MS spectra for native chymotrypsin (top) and ATRP initiator modified chymotrypsin (bottom), described in Experimental Section IV.

Figure 28:
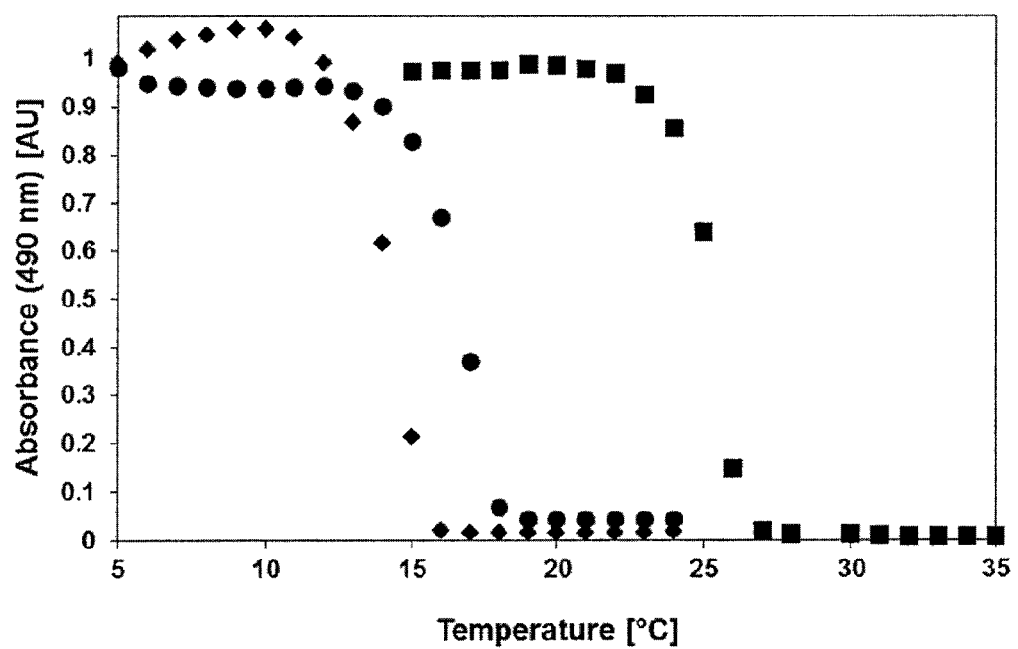

FIG. 28 shows UCST cloud point curves for CT-pSBAm conjugates described in Experimental Section IV.

Figure 29:
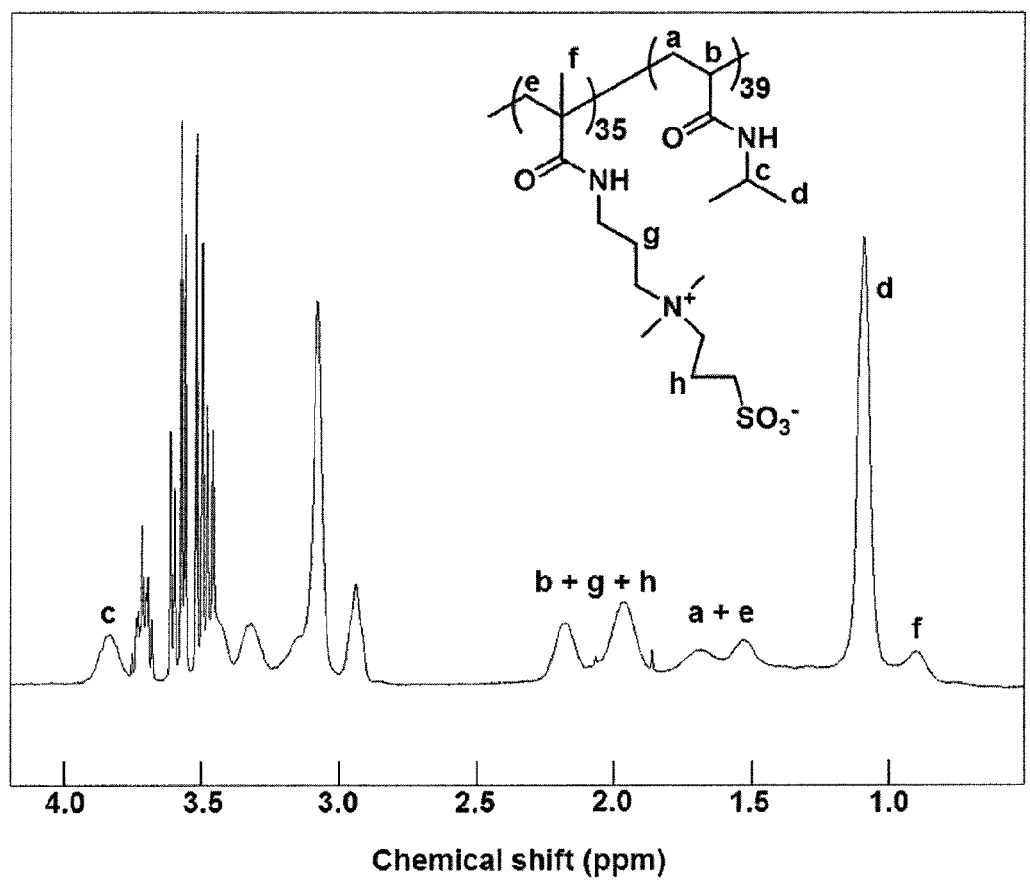
Figure 30:
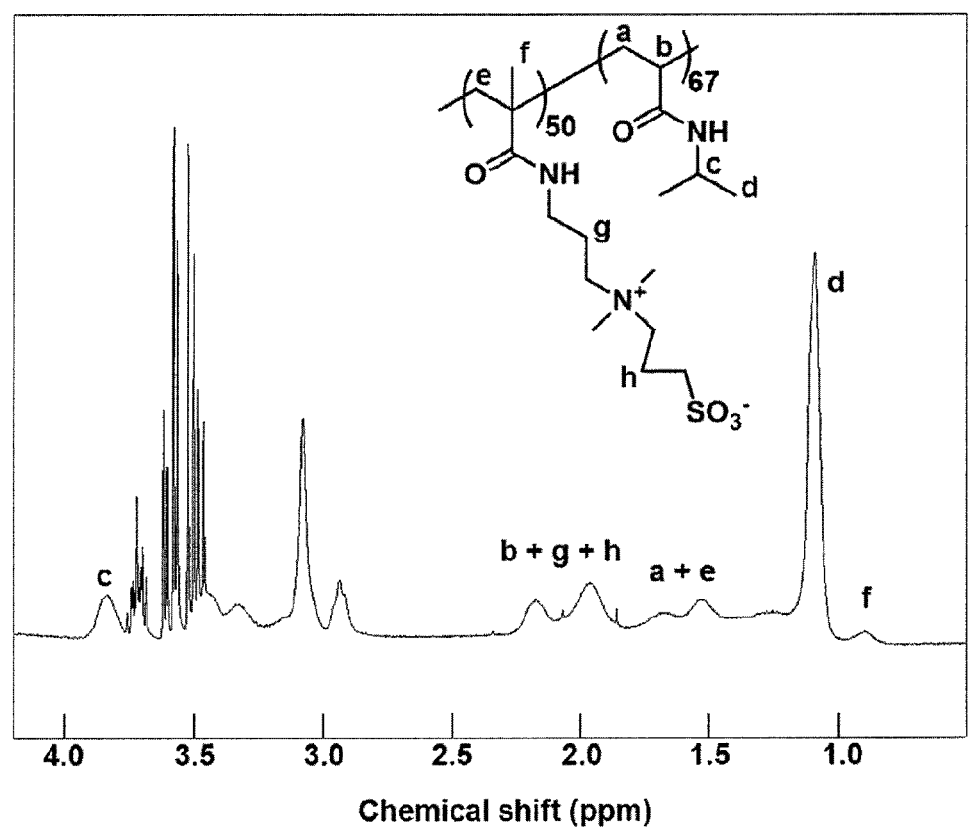
Figure 31:
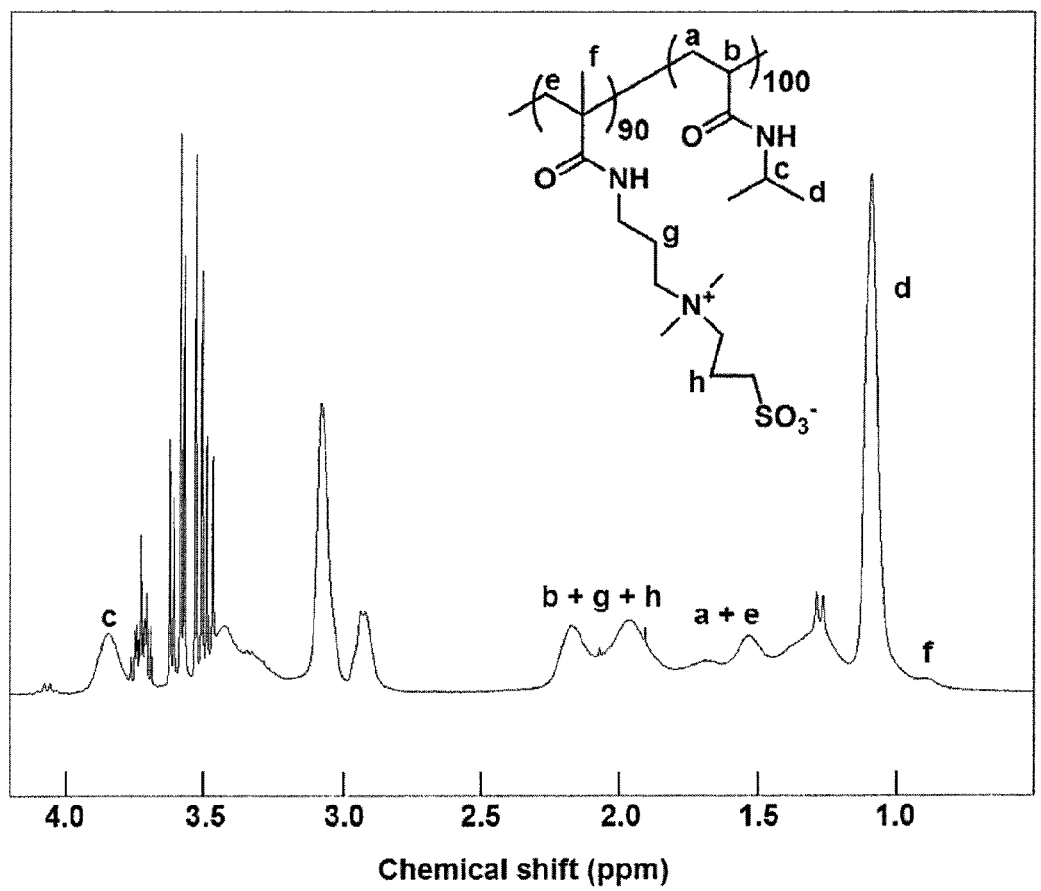

FIGS. 29-31 show NMR spectra for pSBAm$_{35}$-block-pNIPAm$_{39}$ in D$_2$O, pSBAm$_{50}$-block-pNIPAm$_{67}$ in D$_2$O, and pSBAm$_{90}$-block-pNIPAm$_{100}$ in D$_2$O, each cleaved from chymotrypsin using acid hydrolysis.

DETAILED DESCRIPTION AND BEST MODE OF IMPLEMENTATION

The attachment of synthetic polymers to proteins influences activity and stability and offers a means to add novel functions to the protein in a variety of microenvironments. The methods and compositions described herein add significantly to the body of work in this field by allowing a controlled rational approach to the attachment method that permits modification of proteins in a controlled reliable manner. By using monomers to grow polymers that have been determined to be responsive to stimuli to effect a desired property, the protein of interest can be modified with confidence that the polymer protein conjugate will exhibit the desired property, and importantly, will function in the manner for which it was designed in a relevant microenvironment.

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore unless otherwise specified, features, components, modules, and/or aspects of the illustrations can be combined, separated, interchanged, and/or rearranged without departing from the disclosed systems or methods.

Introduction

For convenience, certain terms employed in the specification, examples, and appended claims are collected here. Unless defined otherwise, all technical and scientific terms used herein have the same meaning as commonly understood by one of ordinary skill in the art.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims, may be read as if prefaced by the word "about" even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The articles "a" and "an" are used herein to refer to one or to more than one (i.e., to at least one) of the grammatical object of the article. By way of example, "an element" means one element or more than one element.

The term "microenvironment" refers to localized conditions within a larger area. For example, association of two molecules within a solution may alter the local conditions surrounding the associating molecules without affecting the overall conditions within the solution.

The term "protein", and the terms "polypeptide" and "peptide" which are used interchangeably herein, refers to a polymer of amino acids.

The term "densely modified" with respect to the protein-polymer conjugates described herein means a density of polymer chains per unit surface area of protein of one polymer chain per 1 to 10 nm² of protein surface area, or a density such that a majority of amine binding sites, and in various embodiments, from about 85-100%, and in some embodiments, all of the amine binding sites, or about 90% of the amine binding sites, or about 86% of the amine binding sites, and at least 85% of the amine binding sites on the surface of the protein are bound to a polymer chain.

The term "ligand" as used herein with respect to a controlled radical polymerization process means a moiety used to solubilize the transition metal salt in the reaction media and to adjust the redox potential and halogenophilicity of the metal center forming a complex with an appropriate reactivity and dynamics for the atom transfer. Exemplary ligands are described in *Handbook of Radical Polymerization*, K. Matyjaszewski and T. Davis, Ed., John Wiley & Sons, Inc. pub. (2002), pp 553-555, 567, incorporated herein by reference.

The terms "active ester functionalized amide-containing controlled radical polymerization initiator", "controlled radical polymerization initiator", or "CRP initiator", or "NHS-functionalized amide-containing initiator" or "NHS-functionalized ATRP initiator", or "ATRP initiator," and the like, are used herein interchangeably, and refer to the water soluble, active ester-functionalized amide-containing controlled radical polymerization (CRP) initiator used in the polymer-based protein engineering methods described herein and comprising the general structure

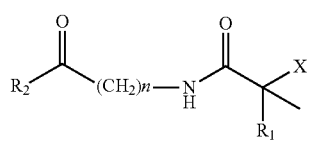

(I)

wherein X is a halogen, such as Br, Cl, or F, or a chain transfer agent; $R_1$ is H or alkyl; $R_2$ is an active ester moiety; and n is an integer from 1 to 6. The active ester moiety may be N-oxysuccinimde ester, nitrophenyl ester, pentahalophenyl ester wherein the halogen is F or Cl, 1-oxybenzotriazole ester, or 2-oxy-4,6-dimethyloxy-1,3,5-triazine ester.

Exemplary chain transfer agents that may form X in structure (I) may, in certain embodiments, comprise the general structure

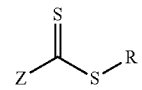

and fall into four classes of thiocarbonylthio agents: (1) dithioesters, where Z is aryl or alkyl, (2) trithiocarbonates where Z is a substituted sulphur, (3) dithiocarbonates (xanthates), where Z is substituted oxygen, and (4) dithiocarbamates, where Z is substituted nitrogen.

In one embodiment, the functionalized amide-containing initiator is an NHS-functionalized amide containing ATRP initiator, and more specifically refers to N-2-bromo-2-methylpropanoyl-β-alanine N'-oxysuccinimide ester (II).

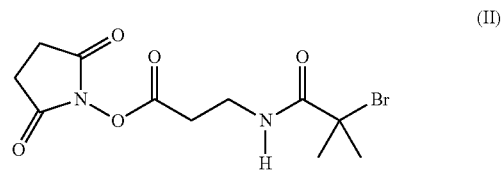 [SMILES: CC(C)(Br)C(=O)NCCC(=O)ON1C(=O)CCC1=O]

(II)

In another embodiment, the functionalized amide-containing initiator is an NHS-functionalized amide-containing ATRP initiator, specifically referring to N-2-chloro-propanoyl-β-alanine N'-oxysuccinimde ester (III), which has Cl as the halogen and one less methyl group next to the halogen than NHS initiator (II).

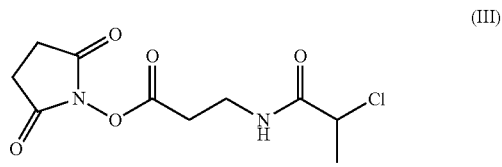 [SMILES: CC(Cl)C(=O)NCCC(=O)ON1C(=O)CCC1=O]

(III)

The active esters $R_2$ in structure (I) may be selected from the following:

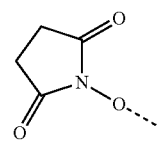

N-oxysuccinimide ester

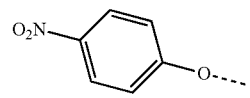

nitrophenyl ester

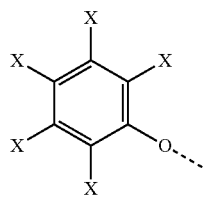

pentahalophenyl ester, wherein X is F or Cl;

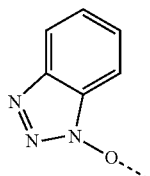

1-oxybenzotriazole ester; and,

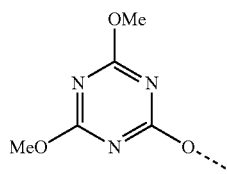

2-oxy-4,6-dimethoxy-1,3,5-triazine ester.

Proteins

Proteins are comprised of fewer than one hundred to thousands of amino acid residues linked by peptide bonds linearly and/or branched, and folded over in three-dimensional configurations. The configuration of the protein determines function. Enzymes, for example, function as biological catalysts that may increase the rate of a biological reaction by $10^6$ to $10^{14}$ fold. Most enzymes are reactive under mild physiological conditions. The configuration of an enzyme, and therefore, the position of available binding sites contribute to the specificity and selectivity of enzymes. Enzymes have an active binding site to receive and bind with a substrate, such as another molecule, to form enzyme-substrate complexes. Upon binding, the enzyme catalyzes the relevant reaction to produce the end product of the catalyzed reaction. Enzymes interact with their substrates and targets by removing them from a solvent, binding, reacting and then returning products to solution. In nature, there are complex protein-protein interactions to achieve modification of the polypeptide to form the final protein structure with its specific function.

Modification of proteins may be achieved biologically by random mutation, or by cloning/expression, expression systems, biodiversity mining, site directed mutagenesis, or directed evolution. These methods, however, often yield only incremental improvements, are difficult and expensive to scale, require long development times, and often only provide situational solutions. Modification of proteins may be achieved chemically by activity in organic solvents, immobilization, cross-linking, conjugation to antibodies, peptide or small molecule conjugation, encapsulation, or phase separation using micelles. These techniques are unsatisfactory because they often result in lower activity, often only provide situational solutions, and often have compatibility issues in vivo.

The invention described herein offers an alternative route to protein modification using polymer based protein engineering. Polymers are rationally designed to specifically alter a protein function. In one embodiment of the method of the invention, an enzyme, such as chymotrypsin, lysozyme, β-Galactosidase, carbonic anhydrase, glucose oxidase, laccase, or acetylcholinesterase, or any protein having surface reactive amino acid side chains that can be covalently coupled to the active ester functionalized amide-containing initiator, is reacted with the functionalized amide-containing initiator to form an initiator modified protein, or initiator modified enzyme, referred to herein as a macroinitiator. Exemplary initiators include, for example, an N-functionalized propanoyl-β-alanine N'-oxysuccinimide ester. The functional group for binding with the surface reactive amino acid on the protein is the active ester. The functional group that reacts with the monomers in the polymerization may be a halogen, such as Br, F, or Cl, or a chain transfer agent. The active ester functionalized amide-containing initiator is immobilized to the amines on the surface of the protein in aqueous solution. Using the "grafting from" approach, the macroinitiator is reacted with monomers of choice in a controlled radical polymerization reaction, such as atom transfer radical polymerization (ATRP) or reversible-addition fragmentation chain transfer (RAFT), to grow the polymer chains on each active site where the amide-containing initiator was immobilized. The result is a protein-polymer conjugate that provides a bioactive molecule having desired properties. The function of the originating protein will be modified by the properties of the conjugated polymers.

In various embodiments, the functionalized amide-containing initiator is formed by the introduction of amide group(s) in the initiator reagent to increase hydrophilicity. One embodiment of the method proceeds, in general, as follows:

1. immobilization of active ester functionalized amide-containing initiator on a protein surface, for example, by mixing the protein of choice and the active ester functionalized amide-containing initiator in a buffer (e.g., 100 mM Na phosphate, pH 8-9) and stirring at, for example, 4° C. for about 3 hours, or a sufficient time to allow the immobilization to occur.

2. isolating the protein-initiator conjugate, for example, by removing any unreacted or unattached small compounds, such as any free initiator, by for example, using a dialysis membrane. The step may also include lyophilizing, and characterizing the protein-initiator conjugate.

3. growing polymer from the protein by "grafting from" using a controlled radical polymerization procedure, such as ATRP or RAFT, or any of the other well documented controlled radical polymerization procedures. This step may include mixing the protein-initiator conjugate and monomer(s) in buffer, charging (bubble) Ar or $N_2$ to remove oxygen; adding a ligand in Ar or $N_2$ charged water, then adding a catalyst (for example, in an ATRP procedure, a copper catalyst, such as Cu(I)) with Ar or $N_2$ bubbling for oxygen removal. The copper-ligand catalyst solution is transferred to the protein/monomer solution using, for example, an Ar or $N_2$ charged syringe. The combined solutions are stirred at about 4-25° C. for a sufficient time to allow polymerization to proceed, typically about 4 hours or overnight.

4. isolating the protein-polymer conjugate, by for example, using a dialysis membrane and optionally refrigerating overnight to remove catalyst, such as any copper-ligand catalyst, and any unreacted monomer(s). The method may also include lyophilizing, and characterizing the protein-initiator conjugate.

Chymotrypsin (CT) is a serine protease that acts in the small intestine, and was selected for use as the exemplary protein in the series of experiments described herein due to the large amount of information available on enzyme activity and stability at a wide range of pH and temperature. (Hedstrom, L. Chem. Rev. 2002, 102, 4501; Kumar, A.; Venkatesu, P. Chem. Rev. 2012, 112, 4283). Chymotrypsin contains 14 surface lysine's, as well as the N-terminus, which allows for high density attachment of polymer around the protein when using the ATRP initiator described herein that reacts preferentially with primary amines.

In addition, chymotrypsin based protein-polymer conjugates could be used to treat exocrine pancreatic insufficiency (Larger, E.; Philippe, M. F.; Barbot-Trystram, L.; Radu, A.; Rotariu, M.; Nobécourt, E.; Boitard, C. Diabetic Medicine 2012, 29, 1047), but the enzyme would have to first survive passage through the stomach and into the small intestine. Previously, β-galactosidase (see Turner, K. M.; Pasut, G.; Veronese, F. M.; Boyce, A.; Walsh, G. Biotechnol. Lett. 2011, 33, 617) (for lactose intolerance) and proline specific endopeptidases (see Fuhrmann, G.; Grotzky, A.; Lukic, R.; Matoori, S.; Luciani, P.; Yu, H.; Zhang, B.; Walde, P.; Schluter, A. D.; Gauthier, M. A.; Leroux, J. C. Nat. Chem. 2013, 5, 582) (for coeliac disease) have been modified with polymers to stabilize proteins with varying success.

Other proteins may be used for the macroinitiator. For example, Lysozyme, β-Galactosidase, carbonic anhydrase, glucose oxidase, laccase, and acetylcholinesterase have each been successfully modified by attachhment to one of the NHS-functionalized initiators described herein to form various embodiments of the protein initiator conjugate of the invention. Most have additionally been modifed with polymer attachment using the growing from method described herein to form various embodiments of the protein-polymer conjugates. In further examples, a uricase based protein-polymer conjugate may be synthesized and could be used for treatment of chronic gout. A PEGylated uricase drug (PEG-loticase) currently approved by FDA for treatment of chronic gout must be injected intravenously. It lowers uric acid concentration in blood stream.

Polymers

Polymer choice is crucial in predicting efficacy of polymer conjugation for the desired purpose. The choice of polymer to bind to the protein of choice using an embodiment of the methods described herein will be dictated by the activity sought to be manipulated. Protein function can be altered by polymer based protein engineering using synthetic or biologically inspired monomers. For example, choosing one or more polymers for stabilization in the GI tract, will allow ingestion of the bioconjugate for in vivo delivery to a desired site where the protein may have a role. The polymer-based protein engineering approach with responsive polymers as described herein will be an improvement to conventional treatments because, in one embodiment, the protein-polymer conjugate produced by the methods described allows conjugation with polymers that will modify the enzyme function to increase stability and permit transport across the intestinal wall into bloodstream. The polymer additions protect the enzyme through low pH stomach conditions, as demonstrated in vitro for CT-pSBAm-block-pNIPAm and CT-pQA conjugates described in more detail in the Experimental series herein. Also, poly (acrylic acid) which collapses at low pH may give increased stability to the enzyme in the stomach. Piperazine may be used as the polymer to increase permeation across the intestinal membrane.

The results seen in the series of experiments described herein may be applied not only to chymotrypsin, but to other proteins, particularly enzymes, having accessible surface reactive amino acid side chains that can covalently couple to the active ester functionalized amide-containing initiator molecule. Two polymers, pSBAm and pNIPAm, were chosen to study the effect of phase transitions at both high and low temperature on CT bioactivity. The LCST temperature of pNIPAm is between room temperature and body temperature. Thus, it is a good candidate to incorporate into materials that might need to be synthesized in aqueous solution at room temperature, but then change behavior once in the body, such as an enzyme targeted to fat tissue where it would likely need to be hydrophobic. Attaching a UCST polymer to an enzyme can potentially increase stability at low temperature, and increase long term storage time before use. A protein-polymer conjugate incorporating both of these polymers, which is described herein, could serve both purposes. In addition, the unique geometry of both UCST and LCST containing polymers in the same chain allowed for the examination of the interaction between each polymer block and CT at different phase transition temperatures. Stimuli responsive protein-polymer conjugates that respond to one stimulus often show slightly different behavior than free polymer because of interactions with or shielding by the protein. It was hypothesized that temperature responsive properties could be altered by the enzyme as well as another polymer block that doesn't respond to stimuli (similar to pNIPAAm-b-PAA, see Kulkarni, S.; Schilli, C.; Grin, B.; Muller, A. H. E.; Hoffman, A. S.; Stayton, P. S. Biomacromolecules 2006, 7, 2736) or that responds to a different stimulus. Thus, a chymotrypsin protein-polymer conjugate was designed to easily examine this hypothesis as well as the effect of polymer conjugation of enzyme bioactivity at multiple stimuli (high and low temperature).

EXPERIMENTAL SECTION

Materials and Methods

Materials

α-Chymotrypsin (CT) from bovine pancreas (type II), 2-Bromo-2-methylpropionyl bromide, pepsin from porcine stomach mucosa, Aprotinin (Bovine, recombinant, expressed in Nicotiana (tobacco)), Bowman-Birk chymotrypsin inhibitor from glycine max (soybean), p-toluene sulfonic acid, β-alanine, N-hydroxysuccinimide, N,N'-diisopropylcarbodiimide, copper (I) bromide, copper (I) chloride, 1,1,4,7,10,10-Hexamethyltriethylenetetramine (HMTETA), 2-(dimethylamino)ethyl methacrylate (DMAEMA, passed over a column of basic alumina prior to use), N-succinyl-L-Ala-L-Ala-L-Pro-L-Phe-p-nitoroanilide (Suc-AAPF-pNA), bicinchoninic acid (BCA) solution, copper (II) sulfate solution, dichloromethane, ethyl acetate, 2-propanol, diethyl ether, n-hexane and [2-(Methacryloylamino)ethyl]dimethyl-(3-sulfopropyl)ammonium hydroxide) (sulfobetaine methacrylamide), (12-Meth-acryloyloxy)ethyl[dimethyl-(3-sulfopropyl ammonium hydroxide) (DMAPS) were purchased from Sigma Aldrich (St Louis, Mo.) and used without further purification. N-isopropylacrylamide was purchased from Sigma Aldrich (St. Louis, Mo.) and purified by recrystallization using hexane. Tris[2-(dimethylamino)ethyl]

amine (Me6TREN) was synthesized as described by Ciampolini, M.; Nardi, N. *Inorg. Chem.* 1966, 5, 41. Quaternary ammonium (QA) monomer (2-(dimethylethylammonium) ethyl methacrylate) was synthesized according to modified procedure reported by Tsarevsky and co-workers (Tsarevsky, N. V.; Pintauer, T.; Matyjaszewski, K. *Macromolecules* 2004, 37, 9768.) (see details in Experimental Series III below). Dialysis tubes (molecular weight cut off, 25-, 15- and 1-kDa (Spectra/Pore, Spectrum Laboratories Inc., CA)) were purchased from Fisher Scientific (Pittsburgh, Pa.).

Measurements $^1$H-NMR spectra were recorded on a spectrometer (300 MHz, Bruker Avance) in the NMR facility located in Center for Molecular Analysis, Carnegie Mellon University, Pittsburgh, USA with Deuterium oxide ($D_2O$), DMSO-$d_6$, and $CDCl_3$. Routine FT-IR spectra were obtained with a Nicolet Avatar 360 FT-IR spectrometer (Thermo). UV-VIS spectra were obtained and used for enzyme activity determination using a UV-VIS spectrometer (Lambda 2, PerkinElmer) with a temperature-controlled cell holder. Number and weight average molecular weights ($M_n$ and $M_w$) and the polydispersity index ($M_w/M_n$) were estimated by gel permeation chromatography (GPC) on a Water 2695 Series with a data processor, equipped with three columns (Waters ultrahydrogel Linear, 500 and 250), using 100 mM sodium phosphate buffer with 0.2 vol % trifluoroacetic acid (pH 2.5) as an eluent at a flow rate 1.0 mL/min and and [2-(Methacryloylamino)ethyl]dimethyl-(3-sulfopropyl)ammonium hydroxide) (sulfobetaine methacrylamide, with detection by a refractive index (RI) detector. Polyethylene glycol standards were used for calibration. Melting points (mp) were measured with a Laboratory Devices Mel-Temp.

Experimental Series I

Polymer Based Protein Engineering to Rationally Tune Enzyme Activity, pH Dependence and Stability Procedure for Synthesis of NHS-Functionalized ATRP Initiator.

N-2-bromo-2-methylpropanoyl-β-alanine N'-oxysuccinimide ester, the NHS-functionalized amide containing ATRP initiator described herein, was synthesized as follows. A mixture of 2-bromo-2-methylpropionyl bromide (12.4 mL, 100 mmol) and dichloromethane (50 ml) was slowly added into the solution of β-alanine (8.9 g, 100 mmol) and sodium hydrogen carbonate (21 g, 250 mmol) in de-ionized water (200 mL) at 0° C. then the mixture was stirred at room temperature for 2 h. The water phase was washed with dichloromethane (100 mL×3) and adjusted to pH 2 with 1.0 N HCl aq. at 0° C. The product was extracted with ethyl acetate (150 mL×6). The organic phase was dried with $MgSO_4$ and evaporated to remove solvent. N-2-bromomethylpropionyl-β-alanine was isolated by recrystallization from mixture of diethyl ether and n-hexane (1/9 volume ratio). N,N'-diisopropylcarbodiimide (2.8 g, 22 mmol) was slowly added to the solution of N-2-bromo-2-methylpropionyl-β-alanine (4.8 g, 20 mmol), and N-hydroxysuccinimide (2.5 g, 22 mmol) in dichloromethane (200 mL) at 0° C. The mixture was stirred at room temperature for 4 h. After filtering out the precipitated urea, the solution was evaporated to remove solvents. N-2-bromo-2-methylpropionyl-β-alanine N'-oxysuccinimide ester (1) was purified by recrystallization from 2-propanol with a yield of 5.7 g (85%) mp 120-124° C. The chemical structure was confirmed by $^1$H-NMR and IR.

Preparation of the CT-Initiator Conjugate.

CT (1.0 g, 0.56 mmol of amine groups contained) was dissolved in 100 mM sodium phosphate buffer (pH 8.0) at 0° C. After adding the NHS-functionalized ATRP initiator (619 mg, 1.85 mmol), the mixture was stirred in a refrigerator for 3 h and the CT-initiator conjugate was isolated by dialysis using a 15-kDa molecular weight cut-off dialysis tube in de-ionized water in a refrigerator for 24 h and then lyophilized.

Preparation of CT-PDMAEMA Conjugates.

A solution of DMAEMA (169 μL, 1.0 mmol for sample conjugate 1 (C1); 337 μL, 2.0 mmol for C2; 675 μL, 4.0 mmol for C3; 1.35 mL, 8.0 mmol for C4) and CT-initiator conjugate (100 mg, 0.046 mmol of initiator groups) in de-ionized water (30 mL) was sealed and bubbled with Argon in an ice bath for 50 min. Deoxygenated catalyst solutions of HMTETA (55 μL, 0.2 mmol) and Cu(I)Br (29 mg, 0.2 mmol) in de-ionized water (10 mL) was then added to the conjugation reactor under Argon bubbling. The mixture was sealed and stirred for 18 h at 4° C. to avoid self-polymerization of the DMAEMA. CT-PDMAEMA conjugates were isolated by dialysis with a 25-kDa molecular weight cut-off dialysis tube in de-ionized water in a refrigerator for 24 h, and then lyophilized.

Cleavage of the Grafted PDMAEMA from the Conjugate.

CT-PDMAEMA conjugate (10 to 20 mg) and 6 N HCl aq. (2 to 3 mL) were placed in a hydrolysis tube. After three freeze-pump-thaw cycles the hydrolysis was performed at 110° C. for 24 h in vacuum. The cleaved polymer was isolated by dialysis using a 1-kDa molecular weight cut off dialysis tube in de-ionized water and was then lyophilized. The molecular weight of the cleaved polymer was measured by GPC.

Determination of Molecular Weight of the Prepared Conjugates.

Molecular weights of the prepared CT-PDMAEMA conjugates were calculated from estimated molecular weight of cleaved PDMEAME from the conjugate. BCA and absorption assays were also carried out to determine molecular weight of the conjugates. Detailed procedures are provided in the Supplementary Materials section.

Matrix-Assisted Laser Desorption Ionization Time-of-Flight Spectrometry (MALDI-TOF MS).

The molecular weight of the CT-ATRP initiator conjugate was estimated with a Perseptive Biosystems Voyager Elite MALDI-TOF spectrometer in Center for Molecular Analysis, Carnegie Mellon University, Pittsburgh, Pa. The operation of MALDI-TOF spectrum was performed as described previously. (Lele, B. S.; Murata, H.; Matyjaszewski, K.; Russell, A. J. *Biomacromolecules* 2005, 6, 3380-3387).

Dynamic Light Scattering (DLS).

The DLS data were collected on a Malvern Zetasizer nano-ZS, which was located in the Department of Chemistry, Carnegie Mellon University, Pittsburgh, USA. The concentration of the sample solution was kept at 1.0 mg/mL. The hydrodynamic diameter of the native CT and the conjugate was measured three times (12 run to each measurement) at various pH's.

Low Critical Solution Temperature (LCST) Point Measurements.

Figure 9:
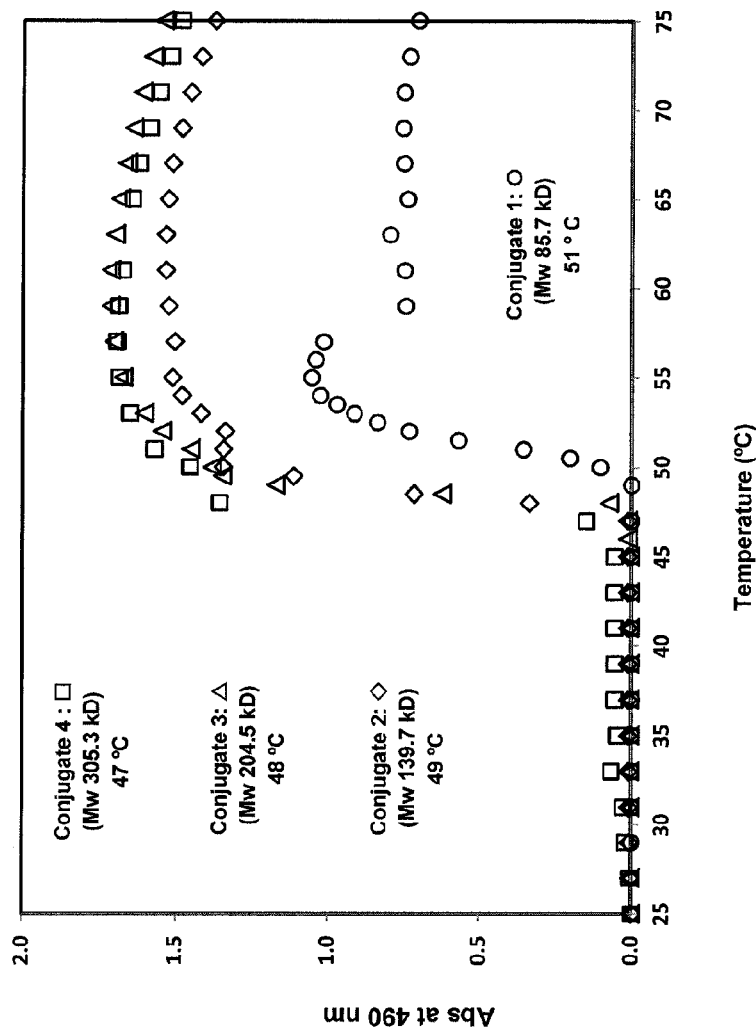
FIG. 9 illustrates the low critical solution temperature of the CT-PDMAEMA example conjugates.

The CT-PDMAEMA conjugate (1.0 mg/mL in 100 mM sodium phosphate buffer pH 8.0) was placed in a glass cuvette, in a UV-VIS spectrometer and the increase in absorption at 490 nm was monitored as function of temperature (0.5-1.0° C./min). The LCST was determined as the initial onset of a sharp increase in absorbance at 490 nm (FIG. 9).

Enzyme Kinetic Assay.

N-Succinyl-Ala-Ala-Pro-Phe p-nitroanilide (0 to 50 μL of 9.60 mM in DMSO) was added to sodium phosphate buffer (990 to 940 μL of 100 mM, pH 5-10). Native CT or conjugates solution (10 μL of 4.0 μM) was added to the substrate solution. The initial rate of hydrolysis of the peptide substrate was monitored by recording the increase in absorption at 412 nm using a UV-VIS spectrometer. The Michaelis-Menten parameters ($k_{cat}$, $K_m$ and $k_{cat}/K_m$) were determined by non-linear curve fitting (equation for Michaelis-Menten parameters) of plots of initial rate versus substrate concentration using the Enzfitter software.

Stability Study.

Native CT and the prepared conjugates (1.5 to 2.0 mL of 40.0 μM) were incubated in 100 mM sodium phosphate buffer at different pH's at 40° C. Aliquots (20 μL) were removed and added into sodium phosphate buffer (180 μL, 100 mM, at 0° C.). The residual activity was calculated as a ratio of initial rates of hydrolysis reaction at given incubation time over the initial activity, which monitored spectrophotometrically as described above. Half-lives for enzyme longevity were estimated by non-linear curve fitting (equation for single exponential decay) using Enzfitter.

Results and Discussion

Synthesis and Attachment of a Water Soluble ATRP Initiator

Figure 2:
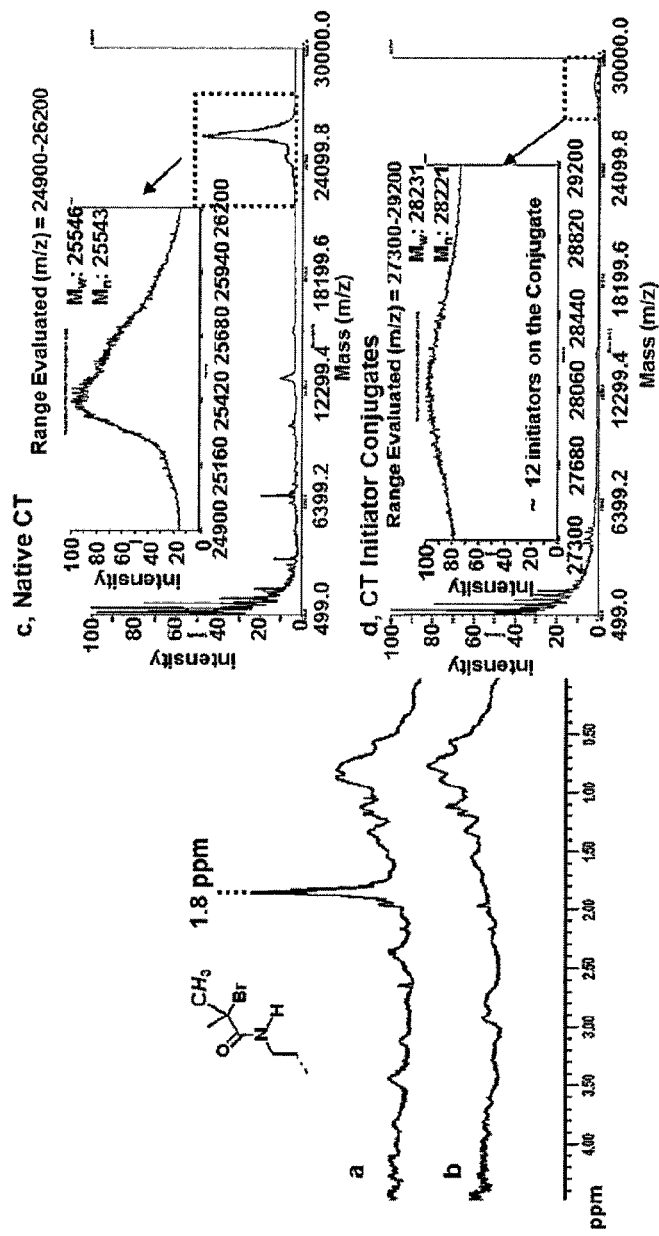
FIG. 2 illustrates the $^1$H NMR and MALDI TOF Mass spectra of native CT and CT-ATRP initiator conjugate. Spectrum a is $^1$H NMR of CT-ATRP initiator conjugate in $D_2O$ and spectrum b is of native CT in $D_2O$. Spectrum c is MALDI-TOF-MS of native CT, and d is that of the CT-ATRP initiator conjugate.

A clear gap in current protein engineering methods is the availability of a water-soluble protein-reactive ATRP initiator that could be used to avoid the exposure of proteins to mixtures of water and organic solvents during PBPE. A novel NHS-functionalized amide-containing ATRP initiator was designed and an example is illustrated in the schematic of FIG. 1. Results from $^1$H-NMR and MALDI-TOF MS demonstrated that that 85% of the CT surface lysines reacted with the initiator (12 of 14 amine groups), providing one initiating point per 5 nm$^2$ of enzyme surface and is illustrated in FIG. 2. Since the initiator density was less than highest practical grafting-from density of PDMAEMA on surfaces (0.6 to 0.99 nm$^{-2}$), it was expected every initiator point to be fully active. Further, this chain density should not lead to early termination and is higher than any other reported approach to protein-initiated ATRP by an order of magnitude. This implies that by simply varying the stoichiometry of the enzyme and initiator the number of sites of attachment can be fine-tuned to exhibit desired properties.

In one embodiment, polymer-based protein engineering (PBPE) was performed with DMAEMA and CT in the presence of copper (I) bromide and HMTETA in buffer (FIG. 1). The chain length of the extending polymeric chains was dependent on the initial molar concentration of DMAEMA and the results are illustrated in Table 1.

TABLE 1

Impact of polymerization conditions on the size of CT-PDMAEMA conjugates.

| | Polymerization | | Cleaved | | | Mw of Conjugate (kDa) | | | | |
|---|---|---|---|---|---|---|---|---|---|---|
| Sample | Concentrations[1] $[I]_0:[M]_0$ | Yield[2] (%) | Polymer[3] $M_n$ ($M_w/M_n$) | $R_g$[4] (nm) | $R_g/$ D[5] | Cleaved Polymer[6] | BCA[7] | Absorption[7] | $D_h$[8] (nm) | LCST[9] (° C.) |
| C1 | 1:21 | 63 | 4,800 (1.51) | 2.8 | 1.2 | 85.7 | 53.8 | 66.7 | 13.0 ± 2.3 | 51 |
| C2 | 1:42 | 65 | 9,300 (1.55) | 3.8 | 1.7 | 139.7 | 131.4 | 120.0 | 18.6 ± 3.3 | 49 |
| C3 | 1:83 | 82 | 14,700 (1.52) | 4.8 | 2.2 | 204.5 | 196.2 | 202.7 | 25.2 ± 3.8 | 48 |
| C4 | 1:163 | 95 | 23,100 (1.57) | 6.1 | 2.7 | 305.3 | 350.3 | 354.2 | 34.3 ± 3.3 | 47 |

[1] The enzyme was modified with 12 initiator units per molecule and the initial initiator concentration ($[I]_0$) was used to calculate the initial concentrations of copper bromide and HMTETA so as to achieve a starting ratio of 1:5:5 ($[I]_0:[Cu(I)Br]_0:[HMTETA]_0$) in deionized water at 4° C.
[2] The yield was defined as the percentage of the total weight of lyophilized CT-PDMAEMA conjugate/total weight of initiator-modified chymotrypsin.
[3] Grafted PDMAEMA was cleaved by vacuum hydrolysis method using 6N HCl at 110° C. for 24 h. Cleaved polymer was isolated by dialysis and the molecular weight of cleaved polymer was estimated by GPC.
[4] The radius of gyration of the polymer in the solution ($R_g$) was assumed to be $0.5N^{0.5}$.
[5] The average distances between polymer chains (D) was assumed to be =2.2 nm ($1/\sigma^{-2}$).
[6] The molecular weight of conjugates was calculated from the measured molecular weight ($M_n$) of the cleaved polymer (assuming 12 chains of equal length) and the initial molecular weight of the initiator-modified enzyme.
[7] The details of the BCA and absorption methods for molecular weight determination are described in the Supplementary Materials.
[8] The hydrodynamic diameter ($D_h$) of the CT-PDMAEMA conjugate was determined by dynamic light scattering at 1.0 mg/mL in 100 mM sodium phosphate (pH 7.0) at 25° C. The $D_h$ of native CT was 4.4 ± 1.3 nm.
[9] The LSCT was measured with a UV-VIS spectrophotometer at 1.0 mg/mL in 100 mM sodium phosphate buffer (pH 8.0).

Figure 3:
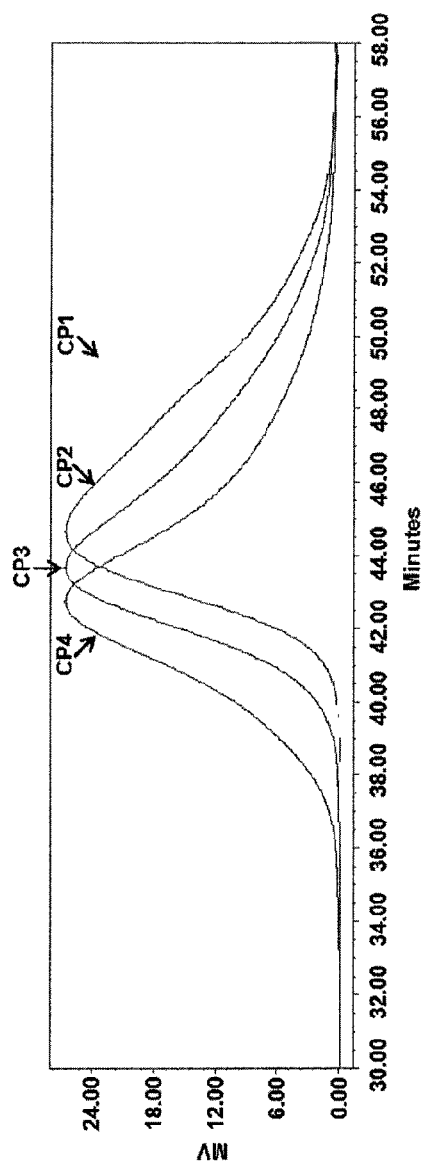
FIG. 3 illustrates the gel permeation chromatography (GPC) experiments for molecular weight determination of cleaved PDMAEMA from the conjugates.

A particular challenge in PBPE is to determine the actual chain length of the polymers. Polymer chains were cleaved from the conjugate by vacuum hydrolysis in 6 N HCl aq at 110° C., followed by isolation with dialysis, and then determined chain length by GPC. The data is illustrated in FIG. 3 and Table 2, and demonstrates rational control of chain length and that all chains grow at the same rate resulting in a relatively low PDI.

TABLE 2

Properties of cleaved PDMAEMA from the conjugates

| Sample | Cleaved polymer[1] $M_n$ ($M_w/M_n$) | Degree of polymerization[2] | $R_g$[3] |
|---|---|---|---|
| CP1 | 4,800 (1.51) | 30.6 | 2.8 |
| CP2 | 9,300 (1.55) | 59.2 | 3.8 |
| CP3 | 14,700 (1.52) | 93.6 | 4.8 |
| CP4 | 23,100 (1.57) | 147.1 | 6.1 |

[1] Molecular weight and the polymer dispersity index of cleaved pDMAEMA from the conjugate was determined by GPC.
[2] Degree of polymerization = $M_n$ of cleaved pDMAEMA/$M_w$ of DMAEMA unit (157 g/mol).
[3] Radius of gyration of cleaved pDMAEMA $R_g = 0.5N^{0.5}$, N is degree of polymerization ref).

In another example, the conformation of the grafted polymer chains and its impact on CT activity and stability was explored. Polymers on surfaces switch between "mushroom" and "brush" regime as a function of surface density and chain length. (Brittain, W. J.; Minko, S. *J. Polym. Sci.: Part A: Polym. Chem.* 2007, 45, 3505-3512). For conjugate C1 and C2 the calculated $R_g/D$ values imply that the polymer had a "mushroom" structure whereas in C3 and C4 the surface density and length would yield a "brush" structure. (Dong, Z.; Wei, H.; Mao, J.; Wang, D.; Yang, M.; Bo, S.; Ji, X. *Polymer* 2012, 53, 2074-2084; Uchida, E.; Ikada, Y. *Macromolecules* 1997, 30, 5464-5469). The hydrodynamic diameters ($D_h$) of the conjugates were determined using dynamic light scattering (DLS). As expected, $D_h$ increased with the length of the grafted PDMAEMA. This result was consistent with theoretical studies relating layer thickness to polymer length on spherical surfaces. (Wijmans, C. M.; Zhulina, E. B. *Macromolecules* 1993, 26, 7214-7224). Thus, PBPE using ATRP provided us with rational control of enzyme-polymer conjugate size.

Tailoring pH-Dependence of Enzyme Activity using PBPE

Figure 4:
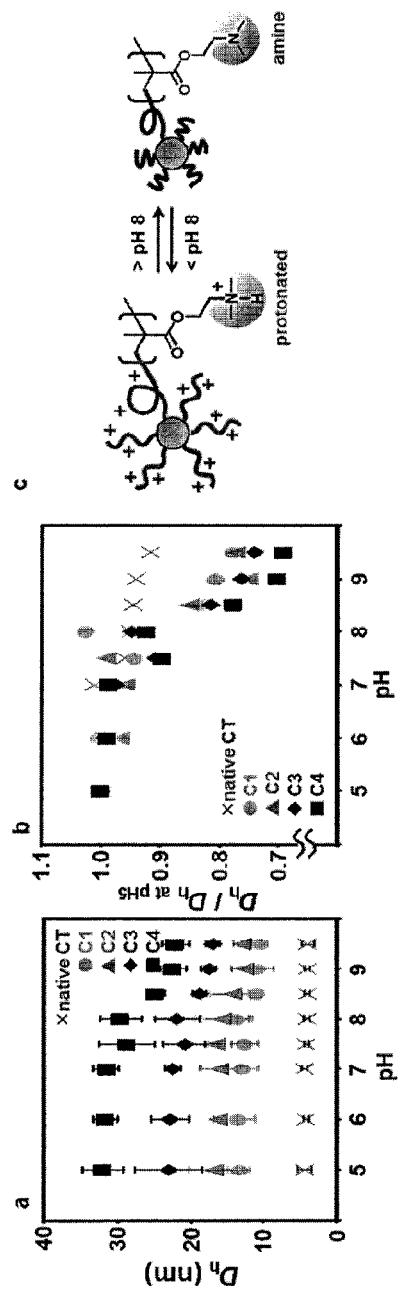
FIG. 4 illustrates the hydrodynamic diameter of native and polymer-modified chymotrypsin as a function of pH. a) pH-dependence of the hydrodynamic diameter of native CT and conjugates; b) Hydrodynamic diameter (for native and modified enzyme) relative to those at pH 5; c) schematic representation of the impact of pH on the conformation of the grafted PDMAEMA chains below and above pH 8.

At pH's below the $pK_a$, PDMAEMA chains stretch and swell as result of electrostatic repulsion between the protonated tertiary amine groups. At pH's above the $pK_a$, the tertiary amine groups of the PDMAEMA are deprotonated and hydrophobic, resulting in collapsed chains. The influence of pH on the size and catalytic activity of the CT-PDMAEMA bioconjugates was investigated in another example. Conjugate diameter increased at low pH (pH 5 to 7), indicating that the grafted PDMAEMA behaved as the polymer did in solution, with the same $pK_a$ (FIG. 4c). (van de Wetering, P.; Zuidam, N. J.; van Steenbergen, M. J.; van der Houwen, O. A. G. J.; Underberg, W. J. M.; Hennink, W. E. *Macromolecules* 1998, 31, 8063-8068). The largest decrease of the particle size as a function of increased pH (30% size reduction) was observed on the conjugate with the longest chains (FIG. 4b).

PBPE would be most useful if one could rationally tailor enzymatic activity by designing the properties and length of the polymer chains. The activity of chymotrypsin is dependent on a catalytic triad that is stabilized by a charge relay network, and therefore charged polymer conjugates may influence activity. Additionally, the conformation of the polymer chains may influence the ability of substrate to bind to the enzyme. The complete kinetic behavior of the CT-catalyzed hydrolysis of the model substrate succinyl-L-alanyl-L-alanyl-L-prolyl-L-phenylalanyl p-nitroanilide (Suc-AAPF-pNA) was measured as a function of pH (Table 3).

TABLE 3

Polymerization conditions and property of free PDMAEMA

| sample | Polymerization Condition[1] $[M]_0/[I]_0$ | Yield[2] (%) | $M_n$ ($M_w/M_n$)[3] | Degree of Polymerization[4] | $R_g$[5] |
|---|---|---|---|---|---|
| F1 | 25/1 | 70 | 4,600 (1.71) | 29.3 | 2.7 |
| F2 | 50/1 | 73 | 9,600 (1.53) | 61.1 | 3.9 |
| F3 | 100/1 | 83 | 13,500 (1.56) | 86.0 | 4.6 |
| F4 | 200/1 | 88 | 23,000 (1.73) | 142.0 | 6.0 |

[1] $[I]_0:[Cu(I)Br]_0:[HMTETA]_0$ 1:1.5:1.5, DI water, 18 h.
[2] Yield (%) = total weight of lyophilized free PDMAEMA/total weight of loaded initiator and DMAEMA × 100.
[3] Molecular weight of free PDMAEMA was estimated by GPC.
[4] Degree of polymerization = $M_n$ of cleaved pDMAEMA/$M_w$ of DMAEMA unit (157 g/mol).
[5] $R_g$ (radius of gyration of the polymer in the solution) = $0.5N^{0.5}$.

The data revealed that above pH 6 the turnover number, $k_{cat}$, was influenced only when the conjugate moved from the "mushroom" (C1 and C2) to the "brush" conformation (C3 and C4). For PEGylated CT, $k_{cat}$ was a function of chain density but not chain length. (Rodriguez-Martinez, J. A.; Rivera-Rivera, I.; Solá, R. J.; Griebenow, K. *Biotechnol. Lett.* 2009, 31, 883-887) It was observed that above pH 9 the $k_{cat}$'s for all the conjugates were similar; above pH 9 the grafted PDMAEMA on all of conjugates would be deprotonated. Below pH 6, a significant increase in $k_{cat}$ for the conjugates was observed relative to native enzyme. This result is interpreted as the protonated PDMAEMA stabilizing the negatively charged carboxyl group of Aspartate 102 in the catalytic triad of the CT, thereby shifting the pH-dependence of the enzyme so as to increase activity at low pH. Similarly, site-directed mutagenesis on serine proteases has been shown to tailor rationally pH-dependence by altering enzyme surface charge. (Russell, A. J.; Thomas, P. G.; Fersht, A. R. *J. Mol. Biol.* 1987, 193, 803-813; 21. Russell, A. J.; Fersht, A. R. *Nature* 1987, 328, 496-500).

Figure 5:
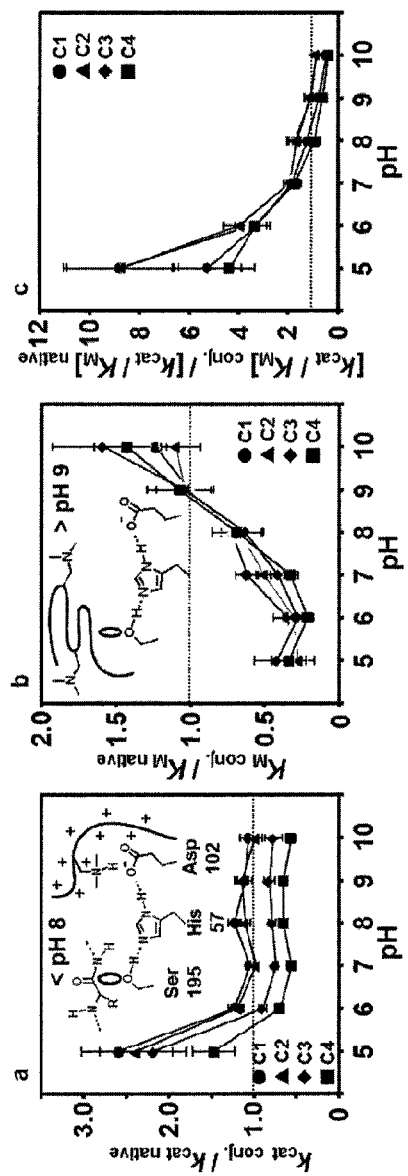
FIG. 5 illustrates the impact of Polymer-Based Protein Engineering on the relative Michaelis-Menten kinetics of the chymotrypsin-catalyzed hydrolysis of Suc-AAPF-pNA. (a) pH-dependence of turnover numbers ($k_{cat}$) for PDMAEMA-CT conjugates relative to those for the native enzyme. The inset schematic illustrates how protonated PDMAEMA could stabilize the deprotonation of Asp 102 below pH 8; (b) pH-dependence of substrate affinities ($K_M$) of chymotrypsin conjugates relative to those for the native enzyme. The inset schematic illustrates how the deprotonated grafted PDMAEMA could sterically hinder the active site of CT above pH 9; (c) pH dependence of catalytic efficiency ($k_{cat}/K_M$) of CT conjugates relative to the native enzyme.

Once a substrate has bound to CT, the charge relay system governs the activity of the enzyme. PBPE's impact on the binding affinity between CT and its model substrate was examined in another example. The Michaelis constant, $K_M$, for all the conjugates at a range of pH's was determined. Below pH 8 substrate binding was improved by PBPE, resulting in a lowered $K_M$ (FIG. 5b). Within this pH range, the PDMAEMA conjugates were, of course, charged, with long-separated chains. PEGylation of CT is known to increase $K_M$ but the structure of PEG on a surface cannot be tuned by changing pH. The results described herein suggest that the well separated ATRP-generated chains did not interfere with the natural state of the active site and at low pH the enzyme retained its native conformation more effectively as a result of increased surface charge. Above the $pK_a$ of PDMAEMA it was observed that the $K_M$s of the conjugates relative to native CT were significantly increased. Without wishing to be bound by theory, it is hypothesized that this reduction of affinity of the substrate at higher pH was because the substrate binding to the active site was inhibited by hydrophobic-hydrophobic interaction between the substrate and deprotonated grafted PDMAEMA chains. Also, collapsed PDMAEMA chains would be expected to sterically hinder the substrate binding pocket of the conjugate. A significant increase in $K_M$ for conjugates C3 and C4 was observed, which have longer grafted PDMAEMA chains at pH 10 (FIG. 5b). Thus, the impact of PBPE methods of the present invention on CT-substrate binding was tunable and permitted reliable prediction of protein-polymer conjugate function.

Combining the data and understanding for the impact of PBPE on $k_{cat}$ and $K_M$ separately, it was observed higher catalytic efficiency ($k_{cat}/K_M$) at lower pHs (FIG. 5c). PBPE led to an almost ten-fold increase in catalytic efficiency of the conjugates at pH 5. For conjugates C1 and C2, which had shorter PDMAEMA chains, the catalytic efficiency was not significantly changed above pH 8.0. Conjugates C3 and C4, however, did exhibit an approximately 50% reduction in catalytic efficiency above pH 8.0. This pH-dependence of enzyme activity for long chain modified enzyme was undoubtedly driven by the $K_M$ effects described above (FIG. 5b).

Impact of Polymer Conformation Temperature Dependence on PBPE-CT Activity

Figure 6:
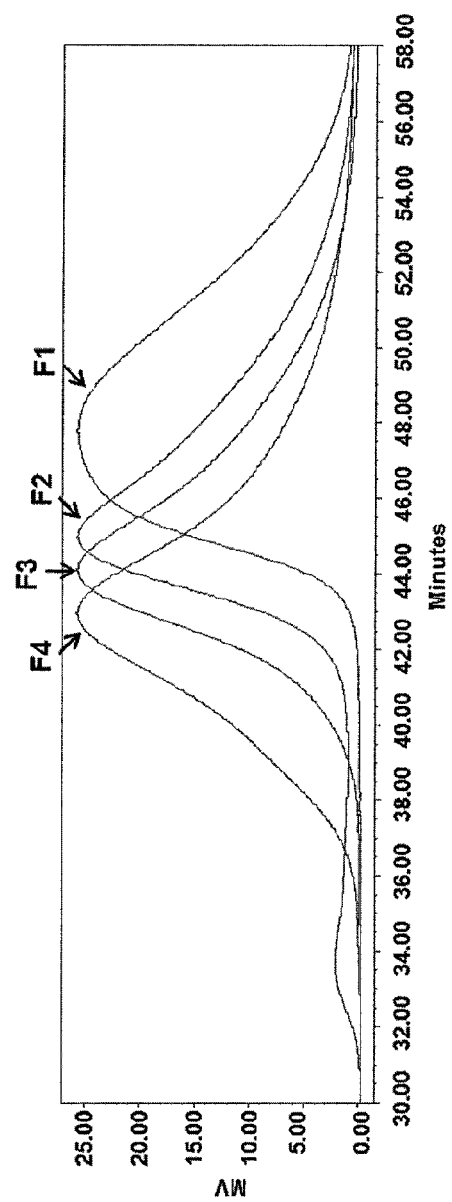
FIG. 6 shows the GPC traces of free PDMEMA prepared separately.

PDMAEMA is also a thermo-responsive polymer with an LCST that is dependent on pH, ionic strength, and molecular weight. Linear and star-shaped PDMAEMAs have LCST's of approximately 50° C. at pH 8. The LCST drops as chain length increases. Below the LCST, PDMAEMA chains of sufficient lengths are hydrated and expanded. (Dong, Z.; Wei, H.; Mao, J.; Wang, D.; Yang, M.; Bo, S.; Ji, X. *Polymer* 2012, 53, 2074-2084) It was determined that the bioconjugates would also change in conformation and relative activity with changes in temperature. The PBPE conjugates showed cloud points between 47-51° C. in the buffer at pH 8.0, exhibiting a drop in LCST with increasing chain length (Table 1 and FIG. 6). Repeated cloud point transitions did not alter enzyme activity in solution.

Figure 7:
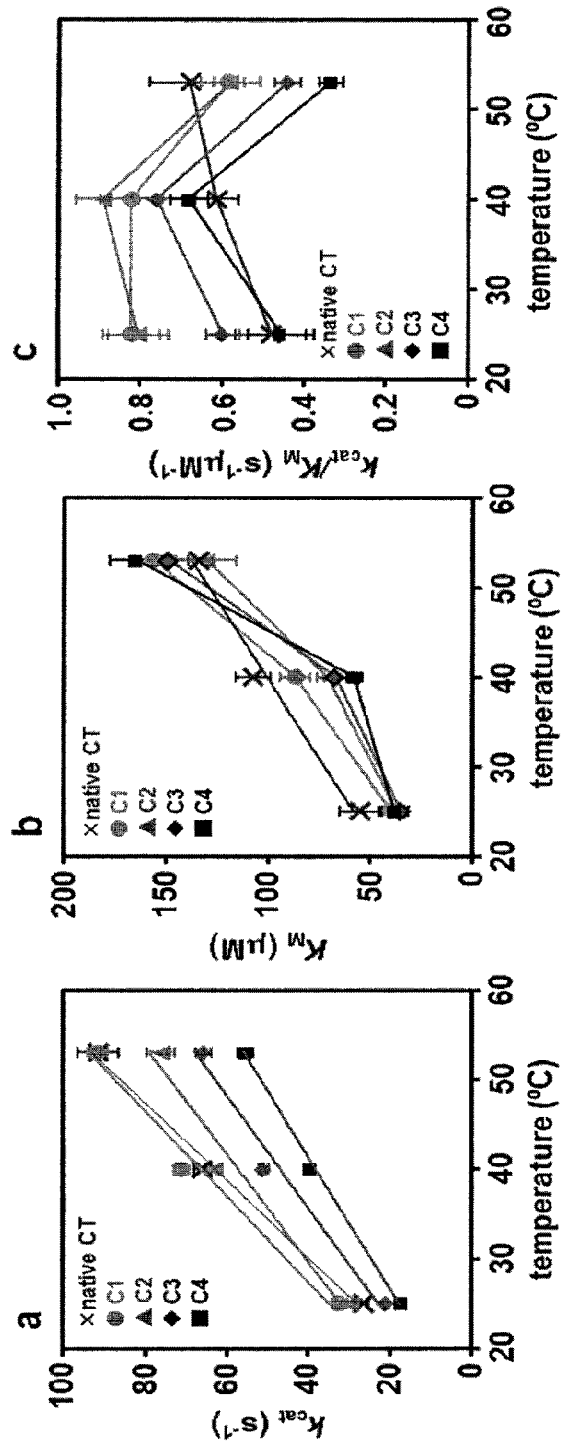
FIG. 7 illustrates the temperature dependence of kinetic constants for native and PBPE-modified chymotrypsin. (a) temperature dependence activity; (b) temperature dependence of specificity; (c) temperature dependence of productivity.
Figure 8:
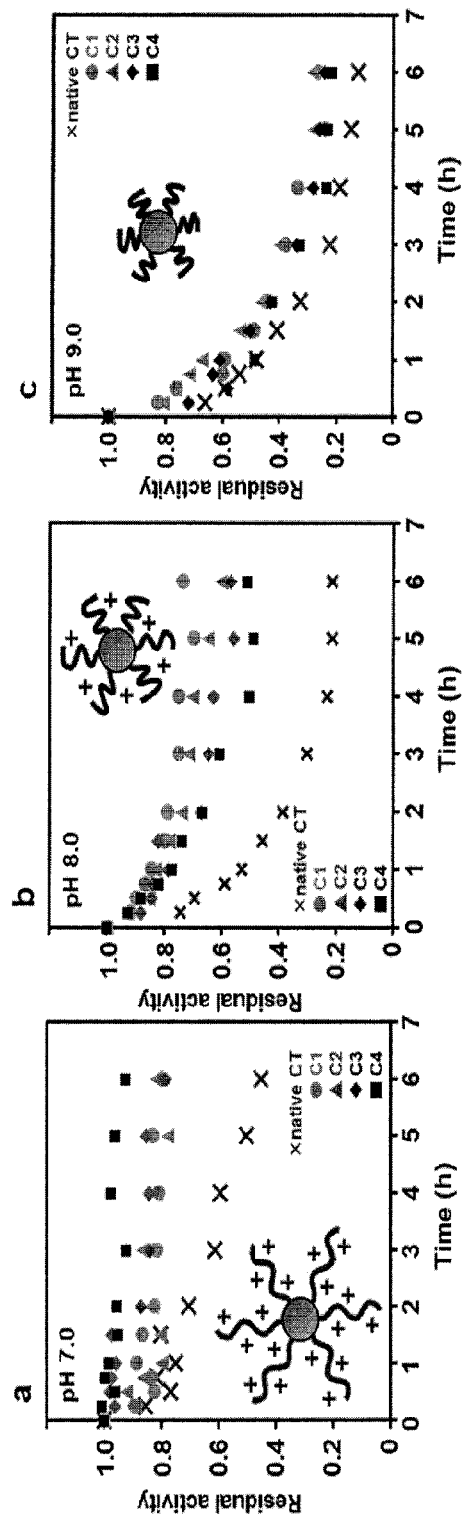
FIG. 8 illustrates the pH-dependence of the rate of irreversible inactivation of and native PBPE-modified chymotrypsin at 40° C. Native chymotrypsin and the conjugates were incubated at pH 7.0 (a), pH 8.0 (b) and pH 9.0 (c). All enzyme assays were performed at 25° C. The inset schematics illustrate the likely conformation of the grafted PDMAEMA chains at each pH (not to scale).

In one embodiment, the effect of PBPE on the temperature dependence of activity was determined by measuring the complete kinetic profiles of the native and modified enzymes with respect to the hydrolysis of the Suc-AAPF-pNA in 100 mM sodium phosphate buffer (pH 8.0) between 25 and 53° C. (FIG. 7 and Table 4).

unfold the protein and also by inhibiting autolysis directly. Since the autolysis reaction of proteases is favored when the enzyme concentration is high, (Yang, Z.; Domach, M.; Auger, R.; Yang, F. X.; Russell, A. J. *Enzyme Microb. Technol.* 1996, 18, 82-89) stability at relatively high enzyme concentration (40 μM) was investigated. At 40° C. the residual activity of the enzyme was measured as a function of pH and shown in FIG. 8, and the first order rate constant for deactivation and half-life were calculated (Table 5).

TABLE 4

Michaelis-Menten parameters of hydrolysis of N-Suc-AlaAlaProPhe-pNA under different pH buffer solution.

| sample | | pH 5.0 | pH 6.0 | pH 7.0 | pH 8.0 | pH 9.0 | pH 10.0 |
|---|---|---|---|---|---|---|---|
| native | $k_{cat}$ | 2.28 ± 0.36 | 12.13 ± 0.57 | 21.54 ± 0.63 | 26.67 ± 1.47 | 29.49 ± 2.00 | 27.69 ± 1.11 |
| | $K_m$ | 212.2 ± 67.2 | 188.9 ± 18.3 | 84.1 ± 7.5 | 55.2 ± 9.7 | 103.6 ± 17.6 | 257.7 ± 19.2 |
| | $k_{cat}/K_m$ | 0.011 ± 0.004 | 0.064 ± 0.007 | 0.256 ± 0.024 | 0.483 ± 0.089 | 0.284 ± 0.052 | 0.107 ± 0.009 |
| C1 | $k_{cat}$ | 5.90 ± 0.30 | 14.90 ± 0.63 | 22.69 ± 0.74 | 32.82 ± 0.75 | 32.85 ± 1.54 | 29.49 ± 2.64 |
| | $K_m$ | 62.5 ± 9.6 | 65.7 ± 8.2 | 52.2 ± 6.1 | 39.8 ± 3.3 | 105.1 ± 12.4 | 318.7 ± 49.4 |
| | $k_{cat}/K_m$ | 0.094 ± 0.015 | 0.227 ± 0.030 | 0.435 ± 0.053 | 0.825 ± 0.070 | 0.313 ± 0.040 | 0.092 ± 0.017 |
| C2 | $k_{cat}$ | 5.44 ± 0.40 | 14.51 ± 0.60 | 21.08 ± 0.34 | 29.49 ± 0.70 | 33.85 ± 0.75 | 27.18 ± 1.84 |
| | $K_m$ | 57.9 ± 13.2 | 57.2 ± 7.4 | 42.5 ± 2.6 | 36.8 ± 3.2 | 107.6 ± 6.0 | 283.1 ± 34.7 |
| | $k_{cat}/K_m$ | 0.094 ± 0.023 | 0.254 ± 0.035 | 0.496 ± 0.032 | 0.801 ± 0.073 | 0.313 ± 0.019 | 0.096 ± 0.013 |
| C3 | $k_{cat}$ | 4.97 ± 0.38 | 10.85 ± 0.20 | 15.96 ± 0.33 | 20.82 ± 0.42 | 24.03 ± 0.75 | 21.31 ± 2.63 |
| | $K_m$ | 88.2 ± 17.8 | 51.9 ± 3.1 | 34.3 ± 2.9 | 34.7 ± 2.3 | 108.3 ± 8.4 | 408.6 ± 81.2 |
| | $k_{cat}/K_m$ | 0.056 ± 0.012 | 0.209 ± 0.013 | 0.466 ± 0.041 | 0.600 ± 0.041 | 0.222 ± 0.019 | 0.052 ± 0.012 |
| C4 | $k_{cat}$ | 3.36 ± 0.16 | 8.38 ± 0.31 | 11.96 ± 0.26 | 17.30 ± 0.80 | 19.21 ± 0.80 | 15.46 ± 1.29 |
| | $K_m$ | 71.4 ± 9.6 | 39.4 ± 5.3 | 27.1 ± 2.8 | 38.0 ± 6.5 | 112.2 ± 11.5 | 368.2 ± 50.8 |
| | $k_{cat}/K_m$ | 0.047 ± 0.007 | 0.213 ± 0.030 | 0.442 ± 0.046 | 0.455 ± 0.081 | 0.171 ± 0.019 | 0.042 ± 0.007 |

Units are as follows: $k_{cat}$, sec$^{-1}$; $K_m$, μM; $k_{cat}/K_m$, sec$^{-1}$ · μM$^{-1}$.

As was the case for pH-induced changes in bioconjugate conformation, the $k_{cat}$'s of the bioconjugates did not exhibit unusual changes at the LCST (FIG. 7a). Some indication was observed that as polymer chain length increased, the degree of temperature dependence of $k_{cat}$ decreased, but this difference was not statistically significant. As temperature increased and the polymer became more "mushroom-like", being tightly woven around the protein surface, a significant increase in $K_M$ relative to that of the native enzyme (FIG. 7b) was observed. Although only three temperatures were probed, the response of $K_M$ to temperatures above the LCST resembled the impact of pH>8.0 on binding affinity. Once again, the hydrophobic characteristics of the peptide substrate were likely interacting with the now hydrophobic PDMAEMA chain that was also sterically hindering access to the active site of the CT (FIG. 7b). Consequently, catalytic efficiency ($k_{cat}/K_M$) of the PBPE-synthesized conjugate was significantly decreased at temperatures above the LCST of the grafted PDMAEMA (FIG. 7c).

Functional Stability of CT-PDMAEMA Conjugates

CT inactivation can occur through unfolding and/or autolysis. The polymer component of the PBPE conjugates may stabilize the enzyme by increasing the energy needed to

TABLE 5 pH-Dependence of irreversible enzyme inactivation for native CT and PBPE conjugates.

| pH | | Native CT | C1 | C2 | C3 | C4 |
|---|---|---|---|---|---|---|
| 7.0 | $k_d$ (1/s) | 2.69 × 10$^{-5}$ | 9.91 × 10$^{-7}$ | 8.13 × 10$^{-7}$ | 9.30 × 10$^{-7}$ | 1.06 × 10$^{-6}$ |
| | $t_{1/2}$ (h) | 7.15 ± 0.91 | 194 ± 41 | 237 ± 58 | 207 ± 50 | 183 ± 14 |
| 8.0 | $k_d$ (1/s) | 9.88 × 10$^{-5}$ | 5.22 × 10$^{-6}$ | 6.38 × 10$^{-6}$ | 9.91 × 10$^{-6}$ | 2.78 × 10$^{-5}$ |
| | $t_{1/2}$ (h) | 1.95 ± 0.25 | 36.87 ± 6.46 | 30.19 ± 6.83 | 19.43 ± 4.92 | 6.92 ± 1.73 |
| 9.0 | $k_d$ (1/s) | 1.26 × 10$^{-4}$ | 7.14 × 10$^{-5}$ | 6.82 × 10$^{-5}$ | 7.24 × 10$^{-5}$ | 8.99 × 10$^{-5}$ |
| | $t_{1/2}$ (h) | 1.53 ± 0.20 | 2.69 ± 0.42 | 2.82 ± 0.35 | 2.66 ± 0.4 | 2.14 ± 0.34 |

The upper row of data at each pH provide the measured first order deactivation constant ($k_d$ (1/s)) and lower row are the calculated half-lives ($t_{1/2}$ (h)).

CT-PDMAEMA conjugates retained 80 to 90% of initial activity at pH 7 and 40° C. after 6 h, whereas native CT retained only 50% of initial activity (FIG. 8a). The half-lives of all conjugates (182 to 237 h) were significantly longer than the native enzyme (7.2 h). Indeed, all of the conjugates retained around 70% of residual activity at pH 7 and 40° C. after incubation for 10 days, demonstrated in FIG. 9. At pH 7, all of the surface amine groups of the grafted PDMAEMA on the conjugates would have been protonated. It was hypothesized that the considerable net additional charge on each enzyme molecule (from the protonated subunits in the conjugated polymers) would be sufficient to reduce protein-protein interactions (FIG. 8a). The stability of protonated PDMAEMA-CT conjugates were significantly greater than that of PEGylated CT. (Rodriguez-Martinez, J. A.; Rivera-Rivera, I.; Solá, R. J.; Griebenow, K. Biotechnol. Lett. 2009, 31, 883-887) As the pH increased and net surface charges decreased, it was observed that CT and the PBPE conjugates had reduced half-lives. Since the average $pK_a$ value of PDMAEMA decreased with increasing molecular weight, (Dong, Z.; Wei, H.; Mao, J.; Wang, D.; Yang, M.; Bo, S.; Ji, X. Polymer 2012, 53, 2074-2084.) longer grafted PDMAEMA conjugates would also tend to be more collapsed and dehydrated at pH 8, thereby inhibiting autolysis through steric hindrance. Both native CT and the PBPE conjugates, when incubated at pH 9, lost 70-80% of biocatalytic activity after 6 h (FIG. 8c). At pH 9, the amine groups of the PDMAEMA would be deprotonated and dehydrated. One could envisage that the now hydrophobic outer shell of the protein might have induced hydrophobic-hydrophobic interactions that enhanced the degree of autolysis. At all pHs tested, the PBPE conjugates had greater stability than native CT (Table 5).

Using PBPE, examples of dense PDMAEMA-CT conjugates with relatively narrow molecular weight distributions have been synthesized. The ATRP-enabled PBPE approach of the present invention was used to tailor the pH and temperature dependences of activity and stability of the enzyme chymotrypsin. The CT-PDMAEMA conjugates had higher relative enzyme activities compared to native CT below pH 8. Indeed, the conjugates had a ten-fold higher enzyme activity than native enzyme at pH 5.0. The data demonstrated that points of inflection in the pH-activity profiles coincided with points at which the molecular conformation of the conjugate changed. It is observed that biocatalytic activity was strongly influenced by the charge state, conformational morphology, and length of the grafted polymer, and that one could rationally tailor these properties using pH and temperature as tunable variables. The method of polymer-based protein engineering described herein can be used to predictably alter the properties of a protein or even to add a new functionality to an existing protein. The water-soluble, protein reactive ATRP initiator provides a key new tool in harnessing the potential of rationally combining biology and polymer science.

A unique, water soluble ATRP initiator enabling polymer-based protein engineering was designed and has been demonstrated and described in accordance with several examples, which are intended to be illustrative in all aspects rather than restrictive. Thus, the present invention is capable of many variations in detailed implementation, which may be derived from the description contained herein by a person of ordinary skill in the art.

Experimental Series II

Relating to Tailoring Enzyme Activity and Stability

In the previous series of experiments, the ability and benefits of binding one type of polymer to multiple amine binding sites on a protein surface were demonstrated. In the second series of experiments, the ability of the method of the present invention to bind more than one type of polymer to a protein is shown. Because a purpose of polymer based protein engineering is to modify the protein in a controlled and reliable manner to achieve, for example, a physiological benefit when the modified protein functions in vivo, polymers having a known response to a biological parameter were chosen for the experiments.

Two polymers that show temperature responsiveness are poly (N-isopropylacrylamide) (pNIPAm) and poly [N,N'-dimethyl (methacryloylethyl) ammonium propane sulfonate] (pDMAPS), though they respond to temperature in sharply distinct ways. pNIPAm exhibits lower critical solution temperature (LCST) behavior where above ~32° C. the polymer experiences a reversible change in conformation, increasing its hydrophobicity and becoming immiscible in water. The same reversible change is seen for pDMAPS, except that the polymer is immiscible below the upper critical solution temperature (UCST). The UCST of pDMAPS has been shown to have strong dependence on polymer chain length and solution ionic strength while the LCST of pNIPAm is less variable, but still can be affected by several factors, such as degree of chain branching and molecular weight.

A goal of this second experimental series was to controllably manipulate the kinetics and stability of CT-pDMAPS and CT-pNIPAm bioconjugates using temperature as the trigger for a change in enzyme function. Both pNIPAm and pDMAPS were chosen in order to examine changes in relative enzyme activity and stability at stimuli responsive temperatures both above and below room temperature. The contrasting temperature responsive behavior of the UCST and LCST bioconjugates provided an attractive approach to examine how polymer chain collapse at varying temperatures affects enzyme bioactivity, stability, and substrate affinity.

The reaction is illustrated schematically as follows:

Scheme I

1) Initiator immobilization

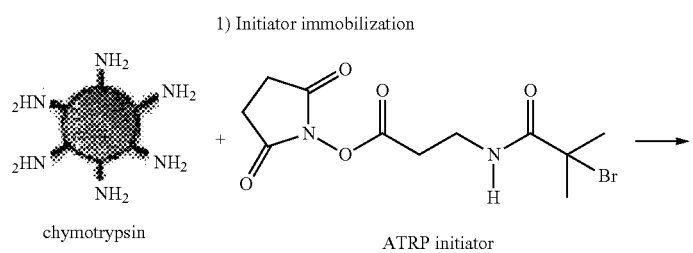

chymotrypsin        ATRP initiator

-continued
2) Surface Initiated ATRP

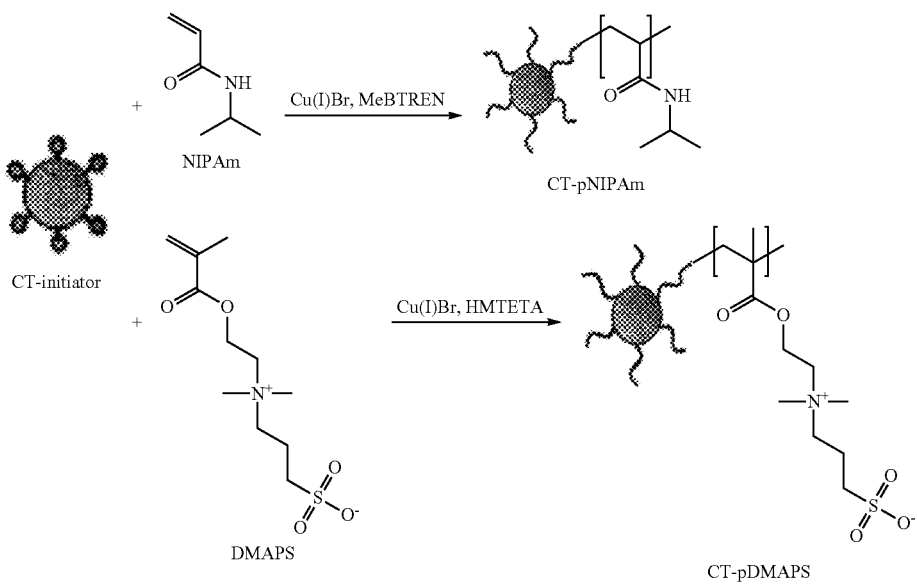

Reaction between the ATRP Initiator and Chymotrypsin

Synthesis of the ATRP initiator was carried out as described previously. Following synthesis, the ATRP initiator (469 mg, 1.4 mmol) and CT (1.0 g, 0.04 mmol protein, 0.56 mmol—$NH_2$ group in lysine residues) were dissolved in sodium phosphate buffer (100 ml. of 0.1 M at pH 8.0). The solution was stirred at 4° C. for 3 h, then dialyzed against deionized water, using dialysis tubing with a molecular weight cut off of 15 kDa, for 24 h at 4° C. and then lyophilized.

Surface Initiated ATRP from CT-Initiator

To synthesize the CT-pDMAPS conjugates, the CT-Initiator complex (50 mg. 0.024 mmol initiator) and DMAPS (335 mg. 1.2 mmol) were dissolved in sodium phosphate buffer (20 mL, pH 6.0). In a separate flask, HMTETA (33 μL, 0.12 mmol) was dissolved in deionized water (10 mL) and bubbled with Argon for 10 min. Cu(1) Br (17 mg. 0.12 mmol) was added to the HMTETA solution and Argon was bubbled for an additional 50 min prior to addition of the copper catalyst solution. The solution was then stirred for 18 h at 4° C. Lastly, the solution was purified using dialysis tubing with a molecular weight cut off of 25 kDa for 48 h against deionized water at 4° C., and the lyophilized.

For CT-pNIPAM synthesis, CT-Initiator conjugate (50 mg. 0.024 mmol initiator) and NIPAm (271 mg. 2.4 mmol) were dissolved in deionized water (20 mL). In a separate flask, Me6TREN (32 μL. 0.12 mmol) was dissolved in deionized water (10 mL) and bubbled with Argon for 10 min. Cu(I)Br (17 mg. 0.12 mmol) was added to the Me6TREN solution and Argon was bubbled for an additional 10 min. The procedure for CT-pNIPAM synthesis from this point forward was the same as described above for CT-pDMAPS synthesis.

Polymer Cleavage from CT Surface

Both PDMAPS and pNIPAm were cleaved from the surface of CT using acid hydrolysis. CT-pDMAPS conjugates were incubated (15 mg/mL) in 6 N HCl at 110° C. under vacuum for 24 h. CT-pNIPAm (20 mg/mL) conjugates were incubated in 4.5 N p-toluene sulfonic acid at 80° C. under vacuum for 72 h. Following incubation, samples were isolated from CT using dialysis tubing (MWCo 1 kDa) for 48 h. and then lyophilized. Lastly, polymer molecular weight was determined using GPC.

Gel Permeation Chromatography

Number and weight average molecular weights ($M_n$ and $M_w$) and the poly-dispersity index ($M_w/M_n$) were estimated by gel permeation chromatography (GPC). For pDMAPS, analysis was conducted on a Waters 2695 Series with a data processor, using 80% 100 mM sodium phosphate buffer (pH=9.0) 20% Acetonitrile with 0.01 volume % $NaN_3$ as an eluent at a flow rate 1 mL/min, with detection by a refractive index (RI) detector. Polystyrene sulfonate standards were used for calibration. For pNIPAm, analysis was conducted using dimethylformamide (DMF) with 50 mM LiBr at a flow rate of 1 mL/min and 50° C., with detection by an RI detector. Poly(ethylene oxide) standards were used for calibration and diphenylethylene was used as a flow marker.

LCST/UCST Determination

CT-pDMAPS and CT-pNIPAm (2-3 mg polymer/mL each) were dissolved in 0.1 M phosphate buffet (pH 8.0). CT-pNIPAm samples were heated from 20 to 35° C. and CT-pDMAPS samples were cooled from 30 to 5° C. at ±1° C./min. The absorbance at 490 nm was measured and LCST/UCST temperature was calculated from the inflection point on the temperature versus absorbance curves.

Dynamic Light Scattering

CT-pDMAPS (3 mg/mL) and CT-pNIPAm (0.5 mg/mL) samples were dissolved in 0.1 M phosphate buffer (pH 8.0) and then filtered using a 0.45 μM cellulose filter. A Malvern Zetasizer nano-ZS was used to measure hydrodynamic radius ($R_h$). Each sample was measured in triplicate or greater at each specified temperature.

CT and CT-Conjugate Biocatalytic Activity

N-succinyl-Ala-Ala-Pro-Phe p-nitroanilide was used at a substrate for enzyme bioactivity assays. In a 1 mL cuvette, 0.1 M sodium phosphate buffer (810-990 μL, pH 8.0, incubated at 25° C.), substrate (0-180 μL, 6 mg/mL in DMSO (0-1.2×10$^{-3}$M)), and enzyme (10 μL, 0.1 mg enzyme/mL 0.1 M pH 8.0 sodium phosphate buffer (4×10$^{-8}$ M)) were mixed. The rate of the hydrolysis was determined by recording the increase in absorbance at 412 nm for the first 30 s after mixing $K_M$ and $k_{cat}$ values were calculated using EnzFitter software when plotting substrate concentration versus initial rate.

Enzyme Stability

Native CT and CT conjugates (1 mg enzyme/mL) were dissolved in 0.1 M sodium phosphate buffer (pH 8.0) and incubated in a water bath at either 25° C. or 40° C. At various time points, aliquots were removed and diluted to 0.1 mg enzyme/mL using 0.1 M phosphate buffer (pH 8.0). Residual activity was calculated as the percentage of activity remaining relative to the activity at time zero. Substrate (Suc-AAPF-pNA) concentration was kept constant at 288 µM for each sample and time points.

Results and Discussion

Reaction Between the ATRP Initiator and Chymotrypsin

In order to generate highly modified enzyme-polymer conjugates a water-soluble protein-reactive ATRP initiator was synthesized. To determine the efficiency of reaction between the enzyme (chymotrypsin) and the initiator, the increase in molecular weight was measured using MALDI-TOF. On average, 12 ATRP initiating moieties were attached to each CT molecule, through the reaction of an NHS-ester on the initiator molecule with primary amine groups, either on surface accessible lysine residues or the N-terminus. Consequently, for each CT molecule there were 12 different sites from which polymer chains could be grown. Following conjugate synthesis, acid hydrolysis was used to cleave both pDMAPS and pNIPAm from the surface of CT molecules for polymer molecular weight determination. Subsequent GPC analysis yielded number average molecular weight values ($M_n$) of 10 kDa for pDMAPS and 9 kDa for pNIPAm. From these $M_n$ values, conjugate molecular weights were calculated to be 148 kDa for CT-pDMAPS and 135 kDa for CT-pNIPAm. Now that it had been ensured that chymotrypsin could be modified through the high density attachment of thermo-responsive grown from polymers, the temperature dependence of bioconjugate structure and function was explained.

Physical Properties of CT-pDMAPS and CT-pNIPAM Conjugates

The lower critical solution temperature (LCST) and upper critical solution temperature (UCST) behavior of the free polymers and CT bioconjugates were determined. The polymer component of the bioconjugates clearly responded to changes in temperature in the same manner as the free polymer. For CT-pDMAPS, the UCST temperature was 13° C. which compares well with the UCST temperature for free pDMAPS polymer (12° C.). The LCST for the polymer component of CT-pNIPAm (~29.5° C.) was only slightly lower than the LCST for free pNIPAm (30° C.). LCST and UCST transitions for the free polymer are representative of polymer chain collapse, but the thermodynamics governing these behaviors are not the same. Phase transition during LCST is an entropy driven process, while UCST events are generally governed by changes in enthalpy. For each of the conjugates, the change from extended polymer to collapsed polymer occurred slightly more rapidly than for free polymer (note the difference in slope). It is possible that the protein-polymer interface was influencing the thermo-responsive behavior. Above a polymer's LCST, the polymer chains collapse and become insoluble in aqueous media, pushing water molecules to the outside of a newly formed hydrophobic polymer shell. This behavior is reversible; thus, as the sample is cooled back to a temperature below the LCST, the polymer chains rearrange, and are once again soluble in aqueous media. For a polymer that exhibits UCST behavior, the polymer chains are extended and water-soluble above the UCST, and collapsed/insoluble below the UCST temperature in aqueous media. When translating this temperature sensitive behavior from free polymer to enzyme-polymer conjugates, it was hypothesized that two different polymer conformations would be likely when temperature was varied above or below LCST/UCST temperature. Both above the LCST and below the UCST, the bioconjugates should have a collapsed, insoluble behavior. When below LCST and above UCST, an extended polymer component of the bioconjugate, with higher water solubility compared to the collapsed state, should be in existence.

The cloud point curves for the bioconjugates were determined and showed that there was phase separation and insolubility at the specific UCST and LCST temperatures for each of the CT-polymer conjugates. The impact of temperature on bioconjugate size was examined. The hydrodynamic radius ($R_h$) for the CT-pDMAPS and CT-pNIPAm conjugates, measured by Dynamic Light Scattering (DLS) at temperatures of interest near the LCST and UCST, was temperature-dependent. Owing to the longer polymer chain, CT-pNIPAm conjugates had a larger extended state $R_h$ of ~8 nm compared with ~6.5 nm for CT-pDMAPS. The hydrodynamic radius decreased above the LCST for CT-pNIPAm and below the UCST for CT-pDMAPS as the polymers collapsed and became hydrophobic. We hypothesized that as the polymers collapsed, they more fully covered the surface area of the protein rather than extending outward. The specific phase separation behavior for each conjugate exhibited in the cloud point curves was conserved in the $R_h$ measurements. The CT-pDMAPS UCST transition encompassed a larger temperature range when compared with CT-pNIPAm. For CT-pDMAPS, a gradual decrease in $R_h$ plateaued at ~3.8 nm around 15° C. In comparison, CT-pNIPAm conjugates showed a more rapid phase transition with the $R_h$ quickly decreasing from 30 to 31° C. The quick formation of hydrophobic aggregates (high $R_h$) for each CT-polymer conjugate at extreme temperatures prevented the examination of the $R_h$ at temperatures further away from the UCST and LCST. We next completed an exhaustive analysis of the chymotrypsin bio-conjugate activity and specificity as a function of temperature.

Bioconjugate Activity

Overall enzyme activity was retained during cycling of CT-pNIPAm and CT-pDMAPS conjugates above and below their respective LCST and UCST temperatures. As the polymers in the conjugate switched between a collapsed and extended state, no large decrease in conjugate residual activity was observed.

The kinetic constants ($k_{cat}$ and $K_M$) were determined at three different temperatures (5° C., 25° C., and 40° C.) for each of the conjugates and native CT, using Suc-AAPF-pNA as the model substrate. These temperatures were chosen so as to observe enzyme function above and below the UCST and LCST that we determined for the bioconjugates. At 25° C., both CT-pDMAPS and CT-pNIPAm polymers were in their polymer chain extended state.

At 25° C., CT-pDMAPS conjugates showed similar $k_{cat}/K_M$ values to native CT, while CT-pNIPAm conjugates showed slightly lower $k_{cat}/K_M$ values (Table 6 shown in FIG. 26). In addition, CT-Initiator conjugates showed increased $k_{cat}/K_M$ values at each temperature. The ATRP initiator molecule was covalently coupled to the CT surface through the amine side group on lysine residues. Due to this attachment technique, CT surface charge was modified after initiator immobilization, and this modification is believed to be responsible for the increase in bioactivity seen for the CT-Initiator conjugate at all three temperatures.

Several interesting trends were observed when closely examining the temperature dependence of $k_{cat}$ and $K_M$ for the CT-pDMAPS and CT-pNIPAm conjugates. for each temperature, the relative $k_{cat}$ ratio for CT-pDMAPS stayed CT-pNIPAm active site above pNIPAm LCST would be observed in a reduced $k_{cat}$, as observed. These two factors are believed to have caused a lower bioactivity for CT-pNIPAm conjugates at 40° C.

The impact of the polymer-based protein engineering on enzyme stability was assessed.

TABLE 7

Temperature dependence of first order inactivation rate constants and half-lives for chymotrypsin and polymer-based protein engineered chymotrypsin.

| Sample | 25° C. | | 40° C. | |
| --- | --- | --- | --- | --- |
| | $k_{inact}$ (days-1) | $t_{1/2}$ (days) | $k_{inact}$ (days$^{-1}$) | $t_{1/2}$ (days) |
| Native CT | $0.13 \pm 1.2 \times 10^{-2}$ | $5.43 \pm 0.51$ | $6.61 \pm 0.47$ | $0.10 \pm 7.5 \times 10^{-3}$ |
| CT-Initiator | $0.26 \pm 2.0 \times 10^{-2}$ | $2.67 \pm 0.21$ | $23.8 \pm 3.1$ | $0.03 \pm 3.8 \times 10^{-3}$ |
| CT-pDMAPS | $0.05 \pm 8.3 \times 10^{-3}$ | $14.2 \pm 2.39$ | $1.69 \pm 0.16$ | $0.41 \pm 3.9 \times 10^{-2}$ |
| CT-pNIPAm | $0.01 \pm 3.4 \times 10^{-3}$ | $61.2 \pm 18.7$ | $1.04 \pm 0.14$ | $0.66 \pm 8.8 \times 10^{-2}$ |

Stabilities of native CT and CT conjugates were determined by incubating 1 mg enzyme/mL. The inactivation constants ($k_{inact}$) and half-lives ($t_{1/2}$) were calculated by fitting a first order decay to the data.

constant at ~0.75. At all three temperatures, for CT-pDMAPS conjugates, $K_M$ was lower when compared with native CT, meaning there was higher substrate affinity with the CT-pDMAPS conjugate than native CT. It has been hypothesized that reduced $K_M$ values for CT-zwitterionic polymer conjugates resulted from the interaction of the model substrate with pDMAPS polymer. Taking a similar approach, it can be hypothesized that the model hydrophobic substrate for CT used in this study interacted with the hydrophilic pDMAPS polymer surrounding CT, increasing the local concentration of the substrate near the hydrophobic substrate binding pocket, thereby lowering $K_M$ for CT-pDMAPS. As shown in the relative $K_M$ values, this higher affinity was seen at each temperature, but was reduced, perhaps by the collapsed nature of pDMAPS, below the UCST. At 5° C., the relative $K_M$ value for CT-pDMAPS was higher when compared to relative $K_M$ values at 25° C. and 40° C. At temperatures below the UCST of CT-pDMAPS (13° C.), the polymer was in its collapsed state. It is not unreasonable to presume that once pDMAPS was in a collapsed state it would have restricted the access of the substrate to the active site via steric hindrance.

At 40° C., a sharp decrease in CT-pNIPAm bioactivity was seen with a relative $k_{cat}/K_M$ value of 0.12. At this temperature pNIPAm was in its collapsed, hydrophobic state, and $K_M$ likely increased due to steric hindrance. In addition, since pNIPAm is more hydrophobic than pDMAPS, pNIPAm would have a stronger association with the hydrophobic model substrate. It was likely, then, that the long and dense pNIPAm molecules could partition the substrate in the polymer phase, thereby increasing $K_M$. The interaction of pNIPAm with the substrate, which can be seen from the increase in $K_M$ at 25° C., was also exhibited at other temperatures. For CT-pNIPAm conjugates, relative $k_{cat}$ values were similar at both 5° C. and 25° C., and only slightly lower than native CT. At 40° C., the first order rate constant ($k_{cat}$) was much lower for CT-pNIPAm conjugates when compared to native CT, and it was hypothesized that $k_{cat}$ decreased because of a decrease in water availability at the active site. CT catalyzes peptide bond hydrolysis through a charge stabilizing amino acid triad, and consequently, water is needed for the reaction to occur. As pNIPAm polymer chains surrounding CT collapse above the LCST, the polymer would be expected to alter the mobility of enzyme bound water molecules. Changes in water mobility at the Polymer-Based Protein Engineering of Enzyme Stability A first order inactivation model was used to examine the irreversible thermal inactivation of native CT and the bioconjugates at both 25° C. and 40° C. the CT-pNIPAm and CT-pDMAPS conjugates showed dramatically enhanced stability compared to native CT and initiator modified CT. While CT-conjugate stability was higher at both temperatures, the deactivation mechanisms at these temperatures are likely to differ. At 25° C., CT inactivation is due mostly to autolysis whereas at 40° C. both protein structure denaturation and autolysis contribute to the irreversible inactivation of CT. In addition, the stabilization mechanisms for pNIPAm and pDMAPS were likely different. It was expected that pNIPAm would dampen the structural dynamics of CT thereby preventing structural unfolding in a manner similar to that observed after protein PEGylation. In contrast, pDMAPS likely formed charge interactions between the polymer and protein given its zwitterionic structure thereby stabilizing the protein. While different, both mechanisms dramatically increased stability of CT-polymer conjugates at both 25° C. and 40° C. (Table 7). The half-lives of the bioconjugates were orders of magnitude greater than the native chymotrypsin.

In addition to higher general conjugate stability than native CT stability, at both experimental temperatures (25° C. and 40° C.), the stability of CT-pNIPAm conjugates was higher compared to CT-pDMAPS conjugates. At 25° C., both CT-pNIPAm and CT-pDMAPS polymers were in their extended state. The higher stability of CT-pNIPAm was attributed to the lower activity values seen in Table 6 in FIG. 26. Since autolysis was the main contributor to CT denaturation at 25° C., the lower activity values seen as this temperature corresponded to a higher stability. At 40° C., CT-pNIPAm was in its collapsed state, which likely caused a decrease in autolysis by blocking CT molecules access to the active site. The effect of collapsed versus expanded state for the polymer on the tertiary structure of the protein is not known at this time, but is a potential topic for future studies. At 40° C., CT-pDMAPS was in its extended state, and still provided increased stability compared to native CT through steric hindrances and structural stabilization, but to a lower degree than CT-pNIPAm conjugates.

Conclusion

Polymer-based protein engineering alters in a controlled manner the temperature dependence of relative enzyme activity, stability, and substrate affinity. LCST behavior in pNIPAm and UCST behavior in pDMAPS polymers were conserved in the enzyme-polymer bioconjugates grown from the surface of chymotrypsin. In addition, enzyme bioactivity was conserved when activity assays were conducted at temperatures where the conjugates were in both their extended and collapsed states. Interactions between the model substrate and the polymer surrounding the protein core influenced changes in relative substrate affinity ($K_M$), although pDMAPS and pNIPAm showed opposing behavior. Relative substrate affinity was increased in CT-pDMAPS conjugates (lower $K_M$), but decreased (higher $K_M$) in CT-pNIPAm conjugates. When above the LCST and below the UCST (polymer collapsed state), relative activity of the conjugates was maintained, though slightly reduced, while increasing CT stability to autolysis and denaturation. CT-conjugate stability was also higher compared to native CT at 25° C., where the polymer is in its extended, non-temperature responsive conformation. In summary, these results show that water-soluble protein-reactive ATRP initiator could be used as the foundation of a polymer-based protein engineering strategy designed to tailor the temperature dependence of enzyme stability, activity and specificity.

Experimental Series III Relating to Rational Tailoring of Substrate and Inhibitor Affinity Via ATRP Polymer-Based Protein Engineering The various embodiments of the polymer-based protein engineering methods described herein add significantly to the rational design of polymers, whether synthetic or biological, grown from the surface of proteins to specifically alter protein structure and function. Polymer-based protein engineering focuses on rational tailoring of polymer choice based on targeted benefits of polymer conjugation, rather than the chemistry used to yield such bioconjugates. Polymer-based protein engineering is a simpler synthetic approach than those heretofore used, similar in outcomes to protein glycosylation, a natural post-translational modification that assists with correct protein folding and helps regulate cellular functions, such as cell-cell communication, that are dependent upon protein signaling. (see Elmouelhi, N. Y., K. J. *In Biotechnol Bioeng*; Flynne, W. G., Ed.; Nova Science Publishers, Inc.: New York, 2008, p 37.) Protein function can be altered by polymer-based protein engineering using synthetic or biologically inspired monomers much like glycosylation. With polymer-based protein engineering, some of the advantages that come with glycosylation, such as improved stability, can be imparted onto the protein without often complicated biological techniques.

As described extensively herein, protein-polymer conjugates with high density polymers around the protein core can be synthesized using the "grafting from" approach.

In this series of experiments, a massive reversal of chymotrypsin (CT) surface charge using polymer-based protein engineering with poly(quaternary ammonium) (pQA) is described. pQA is a cationic polymer that has commonly been used for antibacterial applications. (Chen, C. Z.; Beck-Tan, N. C.; Dhurjati, P.; van Dyk, T. K.; LaRossa, R. A.; Cooper, S. L. *Biomacromolecules* 2000, 1, 473; Huang, J.; Koepsel, R. R.; Murata, H.; Wu, W.; Lee, S. B.; Kowalewski, T.; Russell, A. J.; Matyjaszewski, K. *Langmuir* 2008, 24, 6785) Other cationic synthetic polymers have seen wide use in delivery of both RNA (Sioud, M.; Sorensen, D. R. *Biochemical and Biophysical Research Communications* 2003, 312, 1220; Averick, S. E.; Paredes, E.; Irastorza, A.; Shrivats, A. R.; Srinivasan, A.; Siegwart, D. J.; Magenau, A. J.; Cho, H. Y.; Hsu, E.; Averick, A. A.; Kim, J.; Liu, S.; Hollinger, J. O.; Das, S. R.; Matyjaszewski, K. *Biomacromolecules* 2012, 13, 3445.) and DNA (Benns, J. M.; Choi, J.-S.; Mahato, R. I.; Park, J.-S.; Kim, S. W. *Bioconjugate Chem* 2000, 11, 637.) nucleotide based therapies to enable transport of drugs across the cell membrane. Modification of enzyme surface charge by site directed mutagenesis or synthetic chemistry has also been shown to cause dramatic effects on protein function. Specifically, modifying protein surface charge has been shown to influence the stability and activity profiles of enzymes in non-aqueous solvents such as ionic liquids (Nordwald, E. M.; Kaar, J. L. *Biotechnol Bioeng* 2013, 110, 2352) as well as shifting the pH-profile of enzyme activity (Russell, A. J.; Fersht, A. R. *Nature* 1987, 328, 496; Sandanaraj, B. S.; Vutukuri, D. R.; Simard, J. M.; Klaikherd, A.; Hong, R.; Rotello, V. M.; Thayumanavan, S. *J Am Chem Soc* 2005, 127, 10693).

Herein, "grafting from" ATRP to form a high density cationic shell around the chymotrypsin core is described. As stated above, exogenous chymotrypsin dosing could be used to treat pancreatic exocrine deficiency, but low stability to stomach acid degradation of unmodified chymotrypsin would likely require high dosing. It was hypothesized that the high density cationic pQA shell surrounding chymotrypsin would dramatically increase stability, shift the pH profile of chymotrypsin activity, and influence inhibitor binding. Four different molecular weight chymotrypsin-pQA conjugates were synthesized to study the effect of PBPE surface charge modification on enzyme kinetics, stability, and inhibitor affinity.

Synthesis of 2-(dimethylethylammonium)ethyl methacrylate (QA Monomer)

2-(dimethyamino)ethyl methacrylate (21.4 mL, 127 mmol) and bromoethane (11.4 mL, 153 mmol) were added in acetonitrile (80 mL). The mixture was stirred at 35° C. overnight. After Diethyl ether (200 mL) was added, crystalized QA monomer was filtered off, washed with diethyl ether, and dried in vacuo; yield 33.7 g (99%), mp 112-114° C. $^1$H NMR (300 MHz, DMSO-$d_6$) δ 1.26 (t, 2H, J=7.2 Hz, $N^+$(CH$_3$)$_2$CH$_2$CH$_3$), 1.90 (s, 3H, =CCH$_3$), 3.12 (s, 6H, $N^+$(CH$_3$)$_2$CH$_2$CH$_3$), 3.49 (q, 2H, J=7.2 Hz, N+(CH$_3$)$_2$CH$_2$CH$_3$), 3.74 (t, 2H, J=4.5 Hz, OCH$_2$CH$_2$N$^+$), 4.51 (t, 2H, OCH$_2$CH$_2$N$^+$), 5.75 (s, 1H, CH=), and 6.08 (s, 1H, CH=) ppm. IR (KBr) 3447, 2986, 1718, 1635, 1457, 1320, 1299, 1168, 1014, 958, 816, 646, 603, and 554 cm$^{-1}$.

Dynamic Light Scattering (DLS).

The DLS data were collected on a Malvern Zetasizer nano-ZS, which was located in the Department of Chemistry, Carnegie Mellon University, Pittsburgh, USA. The concentration of the sample solution was kept at 1.0 mg/mL. Hydrodynamic diameters ($D_h$) of native CT and conjugates were measured three times (12 runs/measurement) in 100 mM sodium phosphate buffer (pH 7.0) at 25° C.

"Grafting from" ATRP of QA Monomer from the CT-ATRP Initiator Conjugate.

A solution of QA monomer (284 mg, 1.07 mmol (CT-pQA$_{25}$); 567 mg, 2.13 mmol (CT-pQA$_{50}$); 1.13 g, 4.26 mmol (CT-pQA$_{100}$); 2.27 g, 8.52 mmol (CT-pQA$_{200}$) and CT-initiator conjugate (α-Chymotrypsin-NHS ATRP initiator) (100 mg, 0.043 mmol of initiator groups) in de-ionized water (30 mL) was sealed and bubbled with Argon in an ice bath for 50 min. Deoxygenated catalyst solutions of HMTETA (24 μL, 0.2 mmol) and Cu(I)Br (13 mg, 0.2 mmol) in de-ionized water (10 mL) was added to the conjugation reactor under Argon bubbling. The mixture was sealed and stirred in a refrigerator for 4 h. CT-pQA conjugates were isolated by dialysis with a 25-kDa molecular weight cut-off dialysis tube in de-ionized water in a refrigerator for 24 h, and then lyophilized.

Cleavage of the Grafted PQA from the Conjugate.

Chymotrypsin-pQA conjugates (10 to 20 mg) and 6 N HCl aq. (2 to 3 mL) were placed in separate hydrolysis tubes. After three freeze-pump-thaw cycles, hydrolysis was performed at 110° C. for 24 h in vacuum. The cleaved polymer was isolated using a 1 kDa molecular weight cut off dialysis tubing in de-ionized water and then lyophilized. The molecular weight of the cleaved polymer was measured by GPC.

Determination of molecular weight of the prepared conjugates. Molecular weights of the prepared CT-pQA conjugates were calculated from estimated molecular weight of cleaved PQA from the conjugate. BCA and absorption assays were also carried out to determine molecular weight of the conjugates. Detailed procedures for BCA and absorption molecular weight calculations are provided in the experimental series above.

Enzyme Activity

N-Succinyl-Ala-Ala-Pro-Phe p-nitroanilide (0 to 50 µL of 9.60 mM in DMSO) was added to sodium phosphate buffer (990 to 940 µL of 100 mM, pH 5-10). Native CT or conjugates solution (10 µL of 4.0 µM) was added to the substrate solution. The initial rate of hydrolysis of the peptide substrate was monitored by recording the increase in absorption at 412 nm using a UV-VIS spectrometer. The Michaelis-Menten parameters ($k_{cat}$, $K_M$ and $k_{cat}/K_M$) were determined by non-linear curve fitting (using the well known Michaelis-Menten kinetics equation, $V=V_{max}[S]/K_M+[S]$, $k_{cat}=V_{max}[E]$ where [E] is enzyme concentration, [S] is substrate concentration, and V is initial rate of the reaction) of plots of initial rate versus substrate concentration using the Enzfitter software. Table 8 below provides the Michaelis-Menten parameters of hydrolysis of Suc-AAPF-pNA from pH 5-10.

Enzyme activity ($k_{cat}$), specificity ($K_M$), and productivity ($k_{cat}/K_M$) values were determined for each of the conjugates and native chymotrypsin at 25° C. in 0.1 M phosphate buffer (pH 5-10). Values were determined by monitoring the enzyme catalyzed hydrolysis of Suc-AAPF-pNA. Enzyme concentration for each of the reactions was 39 nM, with substrate concentrations ranging from 0-700 µM. The reaction was monitored for the first 30 seconds after mixing enzyme and substrate.

Stability

Native CT and conjugates (1.5 to 2.0 mL, 4.0 µM) were incubated in 100 mM sodium phosphate buffer (pH 7.0) at 50 or 60° C., and an artificial gastric acid solution (167 mM HCl aq. pH 1.5) at 37° C. Aliquots (50 µL) were removed and kept at 0° C. before measuring residual activity. The residual activity was calculated as a ratio of initial rates of hydrolysis reaction at given incubation time over the initial activity for each specific sample.

Inhibitor Binding Study.

Enzyme inhibition was assayed by measuring the hydrolytic activities of samples which contained a fixed concentration of protease and varying amounts of inhibitor, including a blank with no inhibitor. Inhibitors and peptide substrate were simultaneously added to the native and conjugate solutions immediately before measuring initial rates. The initial rate of hydrolysis of the peptide substrate was monitored by recording the increase in absorption at 412 nm. To determine dissociation constant of the enzyme-inhibitor complexes (Ki), $V_{max\ app}$ and $K_{M\ app}$ were determined by non-linear curve fitting (equation for Michaelis-Menten parameters) of plots of initial rate versus substrate concentration using the Enzfitter software. The dissociation constants were calculated from secondary plot of $K_{M\ app}/V_{max\ app}$ versus initial inhibitor concentration.

TABLE 8

|   |   | pH 5.0 | pH 6.0 | pH 7.0 | pH 8.0 | pH 9.0 | pH 10.0 |
|---|---|---|---|---|---|---|---|
| native | $k_{cat}$ | 2.85 ± 0.21 | 14.80 ± 1.07 | 26.81 ± 0.80 | 32.00 ± 1.18 | 33.30 ± 1.31 | 36.62 ± 3.11 |
|  | $K_M$ | 184.0 ± 31.1 | 171.1 ± 28.4 | 94.3 ± 11.1 | 82.6 ± 9.3 | 122.7 ± 12.7 | 336.3 ± 52.7 |
|  | $k_{cat}/K_M$ | 0.016 ± 0.003 | 0.086 ± 0.016 | 0.285 ± 0.034 | 0.387 ± 0.045 | 0.272 ± 0.029 | 0.109 ± 0.019 |
| C1 | $k_{cat}$ | 5.06 ± 0.12 | 10.87 ± 0.24 | 14.49 ± 0.17 | 17.5 ± 0.34 | 13.26 ± 0.61 | 9.96 ± 0.30 |
|  | $K_M$ | 68.5 ± 5.1 | 54.1 ± 4.1 | 32.0 ± 1.6 | 34.4 ± 2.8 | 46.61 ± 8.05 | 72.6 ± 6.8 |
|  | $k_{cat}/K_M$ | 0.074 ± 0.006 | 0.201 ± 0.016 | 0.453 ± 0.024 | 0.509 ± 0.107 | 0.285 ± 0.051 | 0.137 ± 0.013 |
| C2 | $k_{cat}$ | 5.50 ± 0.16 | 13.57 ± 0.27 | 16.57 ± 0.18 | 20.95 ± 0.30 | 15.21 ± 0.60 | 7.54 ± 0.16 |
|  | $K_M$ | 70.8 ± 6.5 | 56.0 ± 3.8 | 31.8 ± 1.6 | 36.0 ± 2.1 | 54.0 ± 7.5 | 51.2 ± 4.0 |
|  | $k_{cat}/K_M$ | 0.078 ± 0.008 | 0.242 ± 0.017 | 0.521 ± 0.027 | 0.582 ± 0.035 | 0.282 ± 0.041 | 0.147 ± 0.012 |
| C3 | $k_{cat}$ | 4.42 ± 0.10 | 9.24 ± 0.29 | 13.06 ± 0.22 | 17.22 ± 0.64 | 15.77 ± .78 | 12.96 ± 0.38 |
|  | $K_M$ | 55.2 ± 4.3 | 39.9 ± 4.9 | 34.1 ± 2.4 | 43.6 ± 6.2 | 62.7 ± 10.3 | 88.4 ± 7.6 |
|  | $k_{cat}/K_M$ | 0.080 ± .007 | 0.231 ± 0.030 | 0.383 ± 0.028 | 0.395 ± 0.058 | 0.252 ± 0.043 | 0.147 ± 0.013 |
| C4 | $k_{cat}$ | 4.73 ± 0.12 | 10.85 ± 0.29 | 15.59 ± 0.27 | 21.73 ± 0.40 | 18.89 ± 1.17 | 9.86 ± 0.24 |
|  | $K_M$ | 59.4 ± 5.2 | 49.8 ± 4.9 | 29.3 ± 2.4 | 36.2 ± 2.7 | 62.5 ± 12.8 | 57.6 ± 4.9 |
|  | $k_{cat}/K_M$ | 0.079 ± 0.007 | 0.219 ± 0.023 | 0.521 ± 0.043 | 0.601 ± 0.047 | 0.302 ± 0.065 | 0.171 ± 0.015 |

Units are as follows: $k_{cat}$, sec$^{-1}$; $K_M$, µM; $k_{cat}/K_M$, sec$^{-1}$ · µM$^{-1}$.

Results and Discussion
Polymer-Based Protein Engineering of CT with a Positively Charged Polymer In order to test the hypothesis that a massive reversal of surface charge would affect prot TABLE 9-continued Impact of polymerization reaction conditions on molecular weight and size of cationic shell encapsulated chymotrypsin

| | polymerization | | Cleaved | Molecular weight of conjugate (kDa) | | | |
|---|---|---|---|---|---|---|---|
| sample | Condition[1] [I]$_0$:[M]$_0$ | Yield[2] (%) | Polymer[3] M$_n$ (M$_w$/M$_n$) | cleaved polymer[4] | BCA[5] | Absorption[5] | D$_h$[6] (nm) |
| CT-pQA$_{198}$ | 1:200 | 88 | 52,600 (1.95) | 636.7 | 578.5 | 575.4 | 28.6 ± 6.1 |

[1]12 initiator units per CT-initiator conjugate, [I]0:[Cu(I)Br]0:[HMTETA]0 = 1:2:2, DI water, 4° C., 4 h.
[2]Yield (%) is the total weight of lyophilized CT-pQA conjugate/total weight of loaded CT-initiator and QA monomer × 100.
[3]Grafted pQA was cleaved by vacuum hydrolysis method using 6N HCl at 110° C, 24 h. Cleaved polymer was isolated by dialysis (Mwco 1,000). Molecular weight of cleaved polymer was estimated by GPC.
[4]Molecular weight of conjugate is reported as Mn of cleaved polymer × 12 + 28,000 (molecular weight of CT-initiator).
[5]Methods for molecular weight determined by BCA and absorption methods are provided in Supplementary Materials section.
[6]Hydrodynamic diameter of the chymotrypsin-pQA conjugate was measured using dynamic light scattering with sample conc. 1.0 mg/mL in 100 mM sodium phosphate (pH 7.0) at 25° C.

For the longest chain conjugate (CT-pQA$_{198}$), the conjugate molecular weight was increased over twenty fold from native chymotrypsin. The hydrodynamic diameters (D$_h$) of the conjugates were determined using dynamic light scattering (DLS) in 100 mM sodium phosphate buffer (pH 8). As expected, the D$_h$ of chymotrypsin-pQA increased with the length of the grown pQA, and CT-pQA$_{198}$ D$_h$ was increased ~6 fold over native chymotrypsin. PBPE of chymotrypsin using ATRP provided us with a method to rationally control the molecular weight and size of chymotrypsin-pQA conjugates. The molecular weight of the conjugates described in this series of experiments are much higher than that described hereinabove for the first series of chymotrypsin polymer conjugates. The longest chain conjugate (polymer molecular weight 53 kDa) is double the length of the longest grown pH-responsive polymers, and 1.5 times the length of the longest temperature-responsive grown block copolymer.

Impact of PBPE on Enzyme Bioactivity

Figure 15:
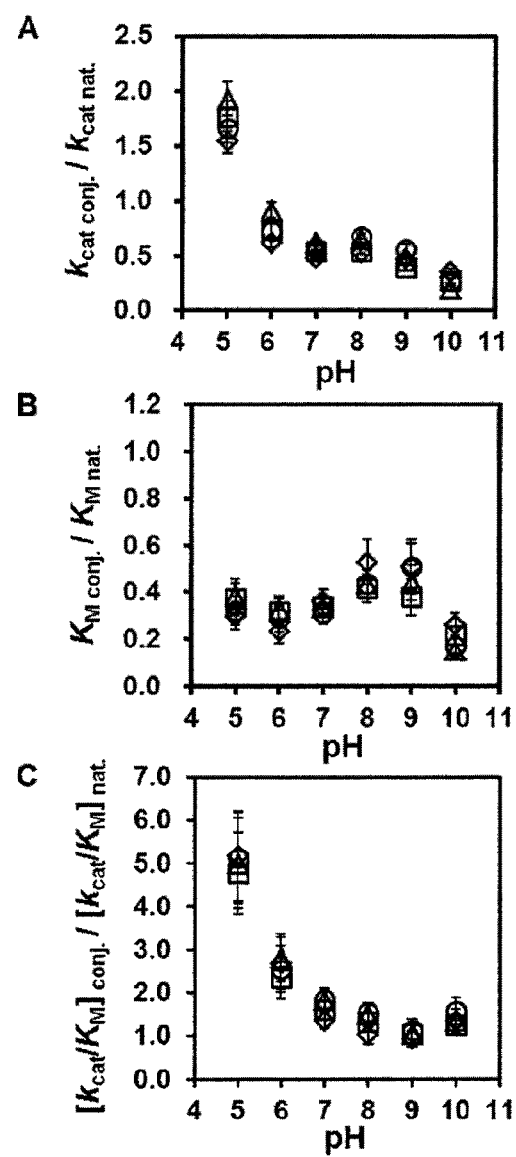
FIG. 15 shows the impact of polymer-based protein engineering on the relative Michaelis-Menten kinetics of chymotrypsin catalyzed hydrolysis of Suc-AAPF-pNA. A. pH dependence of relative turnover number for chymotrypsin-pQA conjugates relative to native chymotrypsin. (CT-pQA27; open square, CT-pQA54; open triangle, CT-pQA108; open diamond, CT-pQA198; open circle) B. pH dependence of relative substrate affinity of chymotrypsin conjugates C. pH dependence of catalytic efficiency of chymotrypsin conjugates.

Following synthesis and physical characterization, the effect of positively charged polymer shells on bioactivity and specificity was examined. Chymotrypsin-pQA bioactivity was determined for each conjugate by monitoring the rate of enzyme catalyzed hydrolysis of N-succinyl-Ala-Ala-Pro-Phe-p-nitroanilide from pH 5-10 at 25° C. Conjugation of the positively charged pQA to chymotrypsin had an effect on both KM and k$_{cat}$ at all pH's (FIG. 15). However, the activity of chymotrypsin-pQA conjugates were not dependent upon molecular weight of the conjugated polymer. (FIG. 15A).

Between pH 7 and 10 the relative k$_{cat}$ for each conjugate was about half of that for native chymotrypsin. The turnover number for enzymes conjugated with a large number and density of polymers are often decreased, likely due to reduced structural dynamics of the protein (see Rodriguez-Martínez, J. A.; Solá, R. J.; Castillo, B.; Cintrón-Colón, H. R.; Rivera-Rivera, I.; Barletta, G.; Griebenow, K. *Biotechnol Bioeng* 2008, 101, 1142.), so this result was not surprising. At lower pH's (pH 5 and 6), the activity ratios for the chymotrypsin-pQA conjugates of each molecular weight were increased compared to kcat values at higher pH's. Chymotrypsin catalytic activity is dependent upon a charge stabilizing amino acid triad consisting of Ser195, Asp102, and His57. In this triad, a negative charge on Asp102 is required for enzyme catalyzed hydrolysis to proceed. In native chymotrypsin, the carboxyl group of Asp102 would be protonated at low pH, and the charge stabilizing effect would be expected to be absent, greatly reducing enzyme activity. For chymotrypsin-pQA, the hypothesis was that the positive charge density imparted by pQA polymer shell stabilized the negative charge on Asp102, which shifted the pH profile for chymotrypsin-pQA conjugates.

Figure 16:
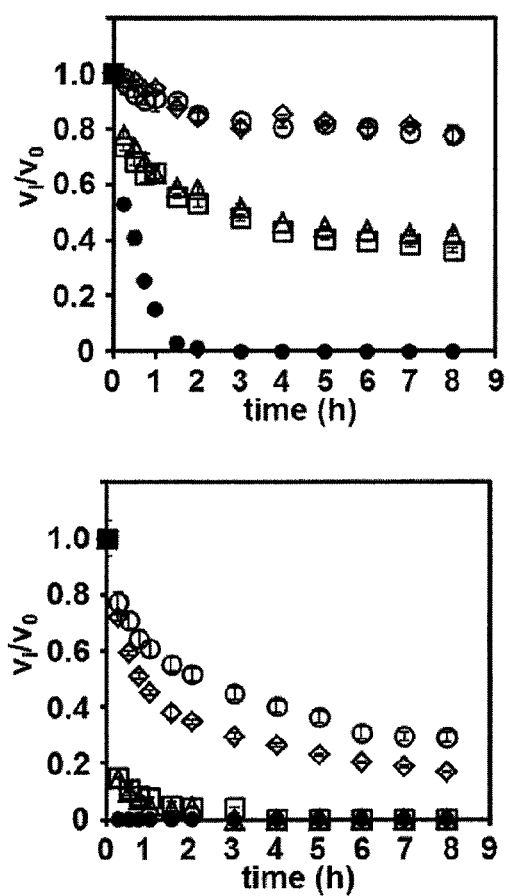
FIG. 16 shows the temperature dependence of irreversible inactivation of chymotrypsin and chymotrypsin-pQA. (A) 50° C. (B) 60° C. Conjugates (CT-pQA$_{27}$; open square, CT-pQA$_{54}$; open triangle, CT-pQA$_{108}$; open diamond, CT-pQA$_{198}$; open circle) and native chymotrypsin (closed circle) were incubated in 100 mM sodium phosphate buffer (pH 8) at 3.9 μM for 8 hours.
Figure 17:
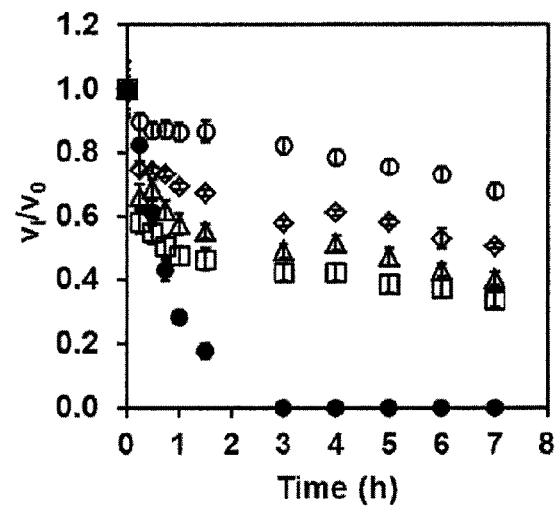
FIG. 17 is a graph showing the rate of irreversible inactivation in 167 mM HCl aq. (pH 1.0) at 37° C. for native chymotrypsin and chymotrypsin conjugates (CT-pQA$_{27}$; open square, CT-pQA$_{54}$; open triangle, CT-pQA$_{108}$; open diamond, CT-pQA$_{198}$; open circle) and native CT (closed circle).
Figure 18:
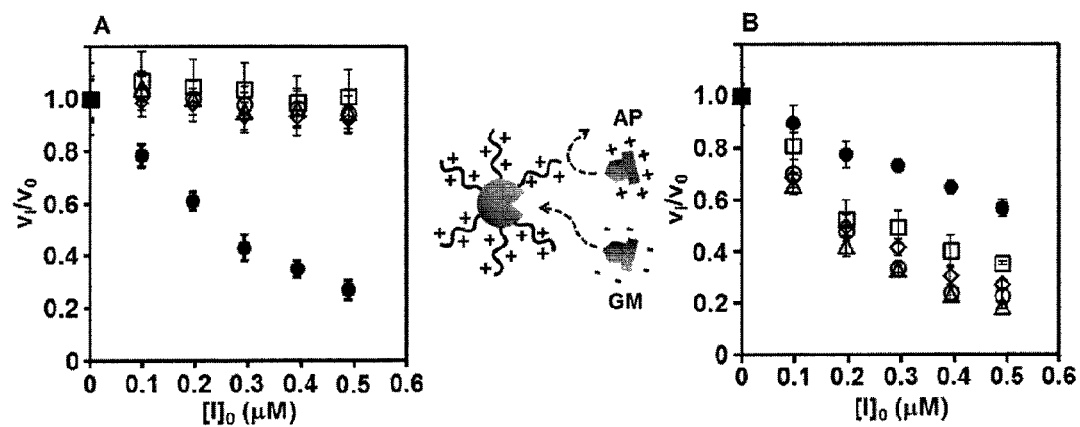
FIG. 18 shows the impact of polymer-based protein engineering on the inhibitor binding to chymotrypsin-pQA conjugates. Concentration dependence of aprotinin (AP) (A) and Bowman-Birk trypsin-chymotrypsin inhibitor from glycine max (GM) (B) on the relative enzymatic activity of conjugates (CT-pQA$_{27}$; open square, CT-pQA$_{54}$; open triangle, CT-pQA$_{108}$; open diamond, CT-pQA$_{198}$; open circle)

It was observed that relative K$_M$'s were not dependent upon chain length (as for k$_{cat}$), and were also independent of pH (FIG. 16B). K$_M$'s for each of the chymotrypsin-pQA conjugates were greatly decreased at each pH, indicating higher substrate affinity compared to native chymotrypsin. At each pH (5-10) relative K$_M$ values were between ~0.2 and ~0.5. The lower K$_M$ values for chymotrypsin-pQA, which have been seen before with charged polymers conjugated to chymotrypsin, were likely due to a partitioning effect between the substrate and the hydrophilic polymer shell around chymotrypsin. It has been suggested that the hydrophobic substrate exhibited a preferential accumulation in the hydrophobic active site pocket of chymotrypsin rather than the pQA shell. (see Keefe, A. J.; Jiang, S. Y. *Nat Chem* 2012, 4, 60) The data produced in these experiments tended to support this hypothesis, although it was interesting to observe that the substrate readily crossed the shell layer since activity was observed.

Enzyme productivity (k$_{cat}$/K$_M$) for each of the chymotrypsin-pQA conjugates was, of course, higher than native chymotrypsin from pH 5 to 10 (FIG. 15C). Relative productivity values were highest at pH 5 (5 fold increase) and 6 (2-3 fold increase), where the increased enzyme activity (k$_{cat}$) and higher substrate affinity (K$_M$) for each molecular weight conjugate improved the performance over native chymotrypsin. Chymotrypsin-pQA conjugates also showed 1-2 fold increases in enzyme productivity at pH values from 7-10. At these higher pH values, the increase in enzyme productivity was due mainly to the lower K$_M$ values as discussed above.

Conjugate Stability at Extremes of Temperature and pH

Next, the stability of native chymotrypsin and chymotrypsin-pQA were examined at extremes of temperature and pH. Chymotrypsin-pQA conjugates of each molecular weight were more stable than native chymotrypsin at both 50° C. (FIG. 16A) and 60° C. (FIG. 16B) in 0.1 M sodium phosphate buffer (pH 8.0). Unlike bioactivity and substrate affinity, the degree of increase in stability for chymotrypsin-pQA conjugates was dependent on polymer molecular weight.

At 50° C., native chymotrypsin lost all activity after 2 h, while all chymotrypsin-pQA conjugates maintained at least 40% of initial activity after 8 h of incubation. At 60° C., where native chymotrypsin lost all activity in 30 min, similar increases in chymotrypsin-pQA stability were observed. CT-pQA$_{198}$ maintained 35% of initial activity after 8 hours.

At these extreme temperatures and at the optimum pH for CT (pH 8), it is believed that two factors influenced irreversible thermo-inactivation of the enzyme. First, chymotrypsin molecules unfolded from their native structure which led to inactivation. Second, after unfolding, access for peptide bond cleavage by other CT molecules (autolysis) was increased. It is believed that each of these mechanisms contributed to CT inactivation at high temperature, and that the growth of pQA from the surface of the enzyme at high density stabilized the enzyme by inhibiting both of these processes. First, it was possible that cationic ammonium ions in the backbone of pQA could have stabilized the tertiary structure of CT similarly to ion salt stabilization in solution following the Hoffmeister series. (see Baldwin, R. L. *Biophys J* 1996, 71, 2056) Second, it has been observed previously that steric hindrance of the polymers around the CT core restricted access for CT molecules to perform autolysis. At both 50° C. and 60° C., the degree of stabilization was polymer chain length dependent. Enzymes are held together by thousands of interactions, but the balance of forces that create a stable structure is delicate. It has been known for a long time that multipoint cross-linking and enzyme crystallization can dramatically stabilize enzymes. A covalently coupled layer of high density polymer that cannot collapse would be expected to prevent unfolding by adding hundreds of polymer-polymer stabilizing forces to the network that retains the structure of the protein.

Chymotrypsin-pQA conjugates of each chain length were also remarkably stable in 167 mM HCl (pH 1) at 37° C. (FIG. 17). Native chymotrypsin lost all activity after 3 hours, but each chymotrypsin-pQA conjugate maintained at least 40% of activity after 8 hours. Chymotrypsin-pQA conjugates were still active up to 99 hours after incubation at this low pH. At pH 1, stabilization of chymotrypsin by the pQA shell must have resulted from structural stabilization since autolysis cannot contribute at pH 1. It has been shown herein that a charged block copolymer enzyme shell dramatically stabilized chymotrypsin at low pH by inhibiting protein unfolding. As was seen with increased stability at elevated temperature, the stability profiles for chymotrypsin-pQA conjugates were dependent on polymer chain length. Chymotrypsin-$pQA_{27}$ showed the lowest stability of the conjugates, while chymotrypsin-$pQA_{198}$ showed the greatest increase in stability. Interestingly, stability profiles of the conjugates at low pH showed a consistent trend with polymer chain length. Conversely, stability for chymotrypsin-pQA conjugates at elevated temperature showed a biphasic behavior where chymotrypsin-$pQA_{27}$ and chymotrypsin-$pQA_{54}$ had similar, but lower stability and chymotrypsin-$pQA_{108}$ and chymotrypsin-$pQA_{198}$ had similar, increased stability. Since chymotrypsin is not active at low pH and autolysis could not contribute to inactivation, it is likely that the polymer only stabilized chymotrypsin structurally through charge effects. Classically, ions were thought to stabilize proteins based on their ability to create a more or less ordered bulk water structure (Lo Nostro, P.; Ninham, B. W. *Chem Rev* 2012, 112, 2286). More recently, it is believed that direct interactions between ions and surface residues in the protein play a more important role in determining protein stability (Paterova, J.; Rembert, K. B.; Heyda, J.; Kurra, Y.; Okur, H. I.; Liu, W. S. R.; Hilty, C.; Cremer, P. S.; Jungwirth, P. *J Phys Chem B* 2013, 117, 8150.; Zhang, Y.; Cremer, P. S. *Current Opinion in Chemical Biology* 2006, 10, 658.). Still, the end result of these interactions is a “salting out” effect, where tertiary structure is stabilized by strengthened hydrophobic interactions in the protein. Within the cationic pQA shell, the local concentration of these stabilizing ions was high which contributed to the increased stability of chymotrypsin-pQA conjugates at both high temperature and low pH.

Rational Tailoring of Enzyme-Inhibitor Binding

Next, the effect of the dense cationic pQA shell around the surface of CT towards inhibitor binding of positively and negatively charged inhibitors was examined. Two protein inhibitors, aprotinin (AP) and Bowman-Birk trypsin-chymotrypsin inhibitor from glycine max (GM), were chosen due to their contrasting surface charges. GM with a pI (4-4.3)41 below the tested pH (8) had negative surface charge, and AP, which has a pI of 10.542, had a positive surface charge. The dense cationic molecular shell should have predictable effects on the ability of the inhibitors to bind to the enzyme. AP was not as effective as an inhibitor for chymotrypsin-pQA conjugates compared to native chymotrypsin, but GM was able to inhibit chymotrypsin-pQA conjugates more quickly than native chymotrypsin (FIG. 18). As shown in Table 10 below, AP Ki values were over 27 fold higher for chymotrypsin-$pQA_{198}$ compared to native chymotrypsin, and GM Ki values were almost 4 fold higher for native chymotrypsin than chymotrypsin-$pQA_{198}$.

TABLE 10

Inhibition constants of aprotinin and glycine max for native and chymotrypsin-pQA198 at 25° C.

| Inhibitor | Sample | Ki (nM) |
|---|---|---|
| Aprotinin | Native CT | 56.3 |
| | CT-$pQA_{198}$ | 1560 |
| Glycine Max | Native CT | 172.0 |
| | CT-$pQA_{198}$ | 46.1 |

It was hypothesized that electrostatic attraction and repulsion were responsible for the change in inhibition kinetics seen for chymotrypsin-pQA conjugates. As AP was positively charged, electrostatic repulsion between the high density cationic pQA shell surrounding CT and AP pushed the inhibitor molecule away from the enzyme active site. Conversely, electrostatic attraction between pQA and the negatively charged GM pulled the inhibitor toward the active site. These repulsive and attractive forces would be expected to influence the local concentration of inhibitor in the region of the active site.

In addition to having opposite surface charges, AP is a completive inhibitor, whereas GM is a noncompetitive inhibitor. Competitive inhibitors, which function by competing for the enzyme active site with the natural substrate, will increase $K_M$ values while not affecting $k_{cat}$ during inhibition. GM, a mixed noncompetitive inhibitor, can inhibit by binding to the active site and other locations on CT's surface, causing both $K_M$ and $k_{cat}$ to change during inhibition. Chymotrypsin-pQA conjugates showed the same changes in $k_{cat}$ and KM as would be expected with each type of inhibition (FIGS. 23/25). Thus, while the cationic pQA shell did predictably manipulate inhibition kinetics of CT, it is likely that the mechanism of binding is still the same as native chymotrypsin.

Conclusions

In this series of experiments, protein-initiated ATRP was used to synthesize chymotrypsin-pQA conjugates of four molecular weights with a dense cationic shell surrounding each enzyme molecule. In support of the hypothesis behind this series, these conjugates changed enzyme activity, substrate affinity, stability, and inhibitor binding in the manner predicted by the hypothesis. Enzyme activity for chymotrypsin-pQA conjugates at low pH was increased compared to native CT due to charge stabilization of the active site catalytic triad. Substrate affinity at pH 5-10 was increased for chymotrypsin-pQA conjugates due to favorable partitioning effects between the cationic shell and the hydrophobic substrate. Enzyme stability was increased at elevated temperature and low pH after pQA conjugation due to both structural stabilization and steric hindrance of autolysis by pQA. The inhibition kinetics of two chymotrypsin inhibitors, aprotinin (competitive) and chymotrypsin inhibitor from glycine max (mixed non-competitive), were also modified by electrostatic attraction and repulsion between the cationic shell and the inhibitor. It has been shown in this study that many different enzyme properties as well as protein-protein interactions can be tuned for a desired purpose using polymer-based protein engineering.

Figure 22:
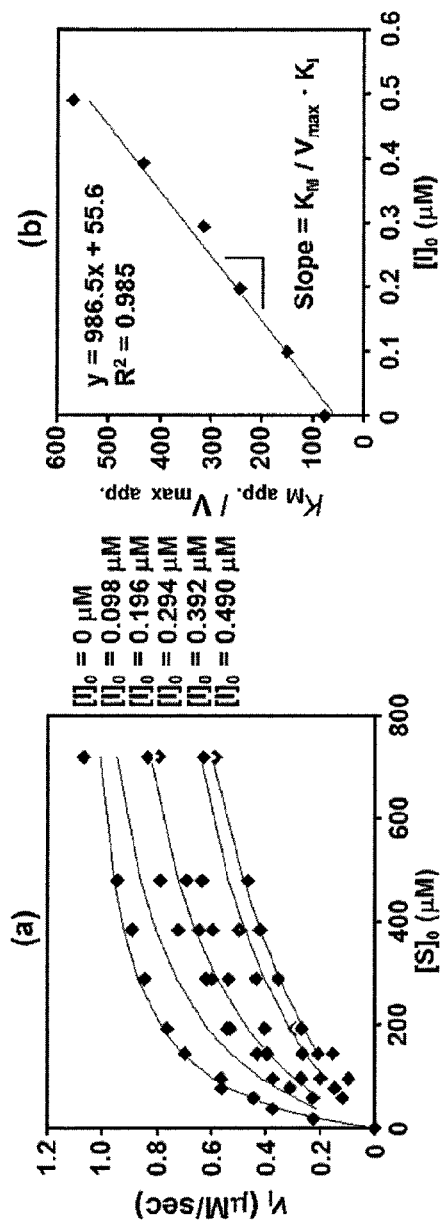
Figure 24:
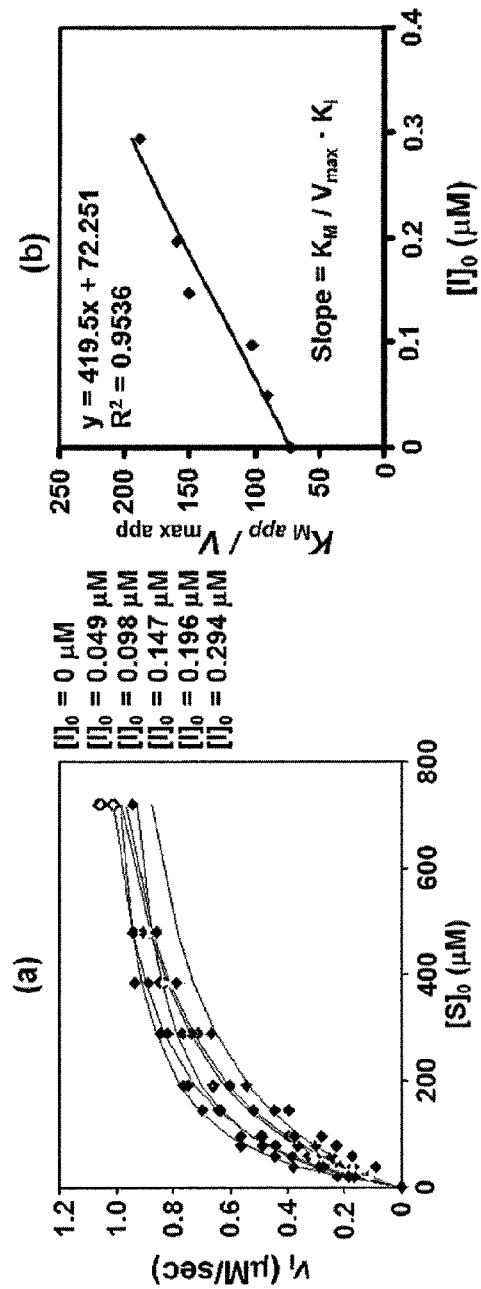

In further support of the foregoing series, the NMR peaks in FIGS. 19 and 20 showed that no degradation of the polymer occurred during the acid hydrolysis procedure. NMR spectra peaks in FIG. 19 are slightly broader due to the overlapping of chymotrypsin peaks. Large peaks that would be assigned to chymotrypsin cannot be seen in FIG. 19, because it is hidden due to its orientation in the center of the dense polymer shell. $^1$H NMR spectra of chymotrypsin-pQA conjugates and cleaved pQA from the conjugates, GPC traces of the cleaved pQA, Table 8 showing the Michaelis-Menten kinetic values of hydrolysis of Suc-AAPF-pNA at different pH, and first ($V_i$ versus $[S]_0$ on hydrolysis of Suc-AAPF-pNA) and secondary plots ($K_{M\ app}/V_{max\ app}$ versus $[I]_0$) for determination of dissociation constant of enzyme-inhibitor complexes. FIGS. 21, 22 and 24 plot additional data and Tables 11, 12, 13 and 14 and apparent $K_M$ and $V_{max}$ values for native chymotrypsin and hymotrypsin-pQA$_{200}$ incubated with aprotinin or GM at 25° C. in 0.1 M sodium phosphate buffer (pH 8.0).

TABLE 11

Apparent $K_M$ and $V_{max}$ values for native chymotrypsin incubated with aprotinin at 25° C. in 0.1M sodium phosphate buffer (pH 8.0)

| [I]0 (mM) | 0 | 0.098 | 0.196 | 0.294 | 0.392 | 0.490 |
|---|---|---|---|---|---|---|
| $K_M$ (mM) | 85.9 | 174.9 | 276.6 | 374.7 | 450.3 | 645.8 |
| $V_{max}$ (mM/sec) | 1.13 | 1.17 | 1.14 | 1.19 | 1.04 | 1.13 |
| $K_M/V_{max}$ (sec−1) | 76.3 | 149.2 | 242.8 | 314.3 | 431.6 | 569.45 |

TABLE 12

Apparent KM and $V_{max}$ values for chymotrypsin-pQA$_{200}$ incubated with aprotinin at 25° C. in 0.1M sodium phosphate buffer (pH 8.0)

| [I]0 (mM) | 0 | 0.98 | 1.96 | 2.94 | 3.92 |
|---|---|---|---|---|---|
| KM (mM) | 46.4 | 69.6 | 106.4 | 113.6 | 160.6 |
| $V_{max}$ (mM/sec) | 0.79 | 0.77 | 0.82 | 0.74 | 0.78 |
| KM/$V_{max}$ (sec−1) | 58.9 | 90.1 | 129.4 | 152.9 | 204.6 |

TABLE 13

Apparent $K_M$ and $V_{max}$ values for native chymotrypsin incubated with GM at 25° C. in 0.1M sodium phosphate buffer (pH 8.0)

| [I]0 (mM) | 0 | 0.049 | 0.098 | 0.147 | 0.196 | 0.294 |
|---|---|---|---|---|---|---|
| $K_M$ (mM) | 78.7 | 94.9 | 120.5 | 182.1 | 196.5 | 213.4 |
| $V_{max}$ (mM/sec) | 1.10 | 1.05 | 1.18 | 1.21 | 1.23 | 1.14 |
| $K_M/V_{max}$ (sec−1) | 71.8 | 90.4 | 102.2 | 150.1 | 159.9 | 188.0 |

TABLE 14

Apparent $K_M$ and $V_{max}$ values for chymotrypsin-pQA$_{200}$ incubated with GM at 25° C. in 0.1M sodium phosphate buffer (pH 8.0)

| [I]0 (mM) | 0 | 0.049 | 0.098 | 0.147 | 0.196 | 0.294 |
|---|---|---|---|---|---|---|
| $K_M$ (mM) | 46.4 | 94.0 | 120.5 | 141.0 | 165.7 | 242.4 |
| $V_{max}$ (mM/sec) | 0.79 | 0.74 | 0.68 | 0.60 | 0.61 | 0.56 |
| $K_M/V_{max}$ (sec−1) | 58.9 | 125.9 | 177.4 | 236.5 | 273.6 | 435.3 |

Effect of pQA Conjugation on Aprotinin Binding to Chymotrypsin

The electrostatic repulsion described in the discussion section required the inhibitor concentration to be approximately 10 fold higher (0-3.92 µM) for chymotrypsin-pQA conjugates compared to native chymotrypsin when determining apparent and KM values.

Experimental Series IV

Relating to Use of Dual Block Polymer-Based Protein Engineering to Increase pH and Temperature Stability In Experimental Series IV, dual temperature responsive CT-pSBAm-block-pNIPAm conjugates with different polymer chain lengths and molecular weights were synthesized using a "grafting from" approach with two successive ATRP reactions. The NHS-functionalized Amide ATRP initiator halide was chlorine.

Synthesis of N-2-chloropropionyl-β-alanine N'-oxysuccinimide ester (1)

A mixture of 2-chloropropionyl chloride (9.7 mL, 100 mmol) and 1,4-dioxane (50 ml) was slowly added into a solution of β-alanine (8.9 g, 100 mmol) and sodium hydrogen carbonate (21 g, 250 mmol) in mixture of deionized water (200 mL) and 1,4-dioxane at 0° C. The mixture was stirred at room temperature for 2 h. The water phase was washed with diethyl ether (100 mL×3) and adjusted to pH 2 with 1.0 N HCl aq. at 0° C. The product was extracted with ethyl acetate (150 mL×6). The organic phase was dried with MgSO$_4$ and evaporated to remove solvent. N-2-chloropropionyl-β-alanine was isolated by recrystallization from a mixture of diethyl ether and n-hexane (1:1 volume ratio); yield 6.8 g (38%), mp 102-105° C. $^1$H NMR (300 MHz, CDCl$_3$) δ 1.73 (d, 3H, J=6.9 Hz, NHC═OCHCH$_3$Cl), 2.66 (t, 2H, J=6.3 Hz, HOOCCH$_2$CH$_2$NHC═O), 3.58 (q, 2H, J=6.3 Hz, HOOCCH$_2$CH$_2$NHC═O), 4.44 (q, 1H, J=6.9 Hz, NHC═OCHCH$_3$Cl) and 7.19 (broad s, 1H, amide proton) ppm. IR (KBr) 3290, 3097, 2980, 2919, 1701, 1657, 1567, 1443, 1370, 1299, 1223, 1078, 988, 936 and 670 cm$^{-1}$.

N,N'-diisopropylcarbodiimide (3.0 g, 24 mmol) was slowly added to the solution of N-2-chloropropionyl-β-alanine (3.6 g, 20 mmol) and N-hydroxysuccinimide (2.8 g, 24 mmol) in dichloromethane (100 mL) at 0° C. The mixture was stirred at room temperature overnight. After filtration, the solution was evaporated to remove solvent. N-2-chloropropionyl-β-alanine. N'-oxysuccinimide ester (III) was purified by recrystallization from 2-propanol with a yield of 4.5 g (82%), mp 93-97° C. $^1$H NMR (300 MHz, CDCl$_3$) β 1.73 (d, 3H, J=6.9 Hz, NHC═OCHCH$_3$Cl), 2.87 and 2.89 (s and t, 4H and 2H, J=6.6 Hz, ethylene of succinimide and NHSOOCCH$_2$CH$_2$NHC═O), 3.70 (t, 2H, J=6.6 Hz, NHSOOCCH$_2$CH$_2$NHC═O), 4.41 (q, 1H, J=6.9 Hz, NHC═OCHCH$_3$Cl), and 7.13, (broad s, 1H, amide proton).

IR (KBr) 3369, 2991, 2934, 1813, 1782, 1729, 1671, 1560, 1449, 1420, 1381, 1297, 1218, 1073, 992, 885, 810, 655 and 597 cm$^{-1}$.

Calculation of ATRP Initiator Immobilization on Enzyme Molecule

FIG. 27 shows the MALDI-TOF-MS spectra for native chymotrypsin and ATRP initiator modified chymotrypsin. Calculated $M_n$ values were 25493 Da for native CT and 28534 Da for CT-initiator-Cl. From these values, calculations indicated that there were 15 initiating sites for every chymotrypsin molecule. The presence of fifteen initiating sites per chymotrypsin molecule indicates that all of the 14 lysines on CT as well as the N-terminus were modified using this technique. From the MALDI spectra, two peaks were seen for native CT (one large intensity peak and one lower intensity) and this shape is conserved in the CT-initiator-Cl molecule as well. However, the peak for CT-initiator-Cl is broader than native CT, indicating the macroinitiator molecules are not completely monodisperse. Thus, it was estimated that each chymotrypsin molecule had between 13-15 initiating molecules, or an average of 14 polymers per enzyme molecule.

Reaction between the ATRP Initiator and Chymotrypsin

Synthesis of the ATRP initiating molecules was carried out as shown in Scheme IV.

Scheme III

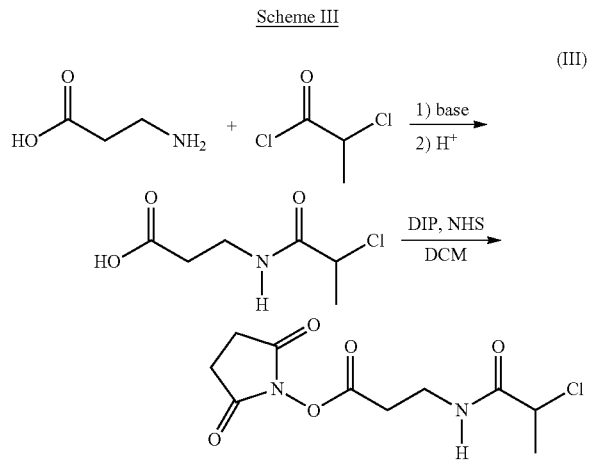

Scheme IV: Synthesis of CT-pSBAm-block-pNIPAm diblock conjugates. Number of initiators and polymer chains per enzyme not drawn to scale.

1) Initiator immobilization

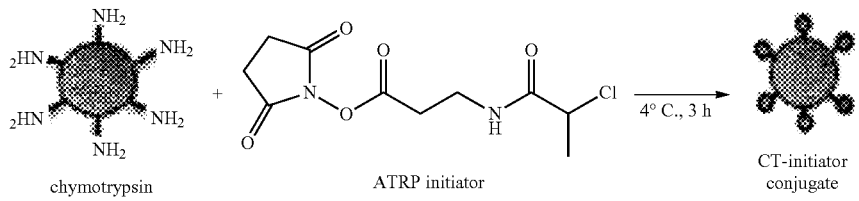

2) Surface Initiated ATRP and chain extension

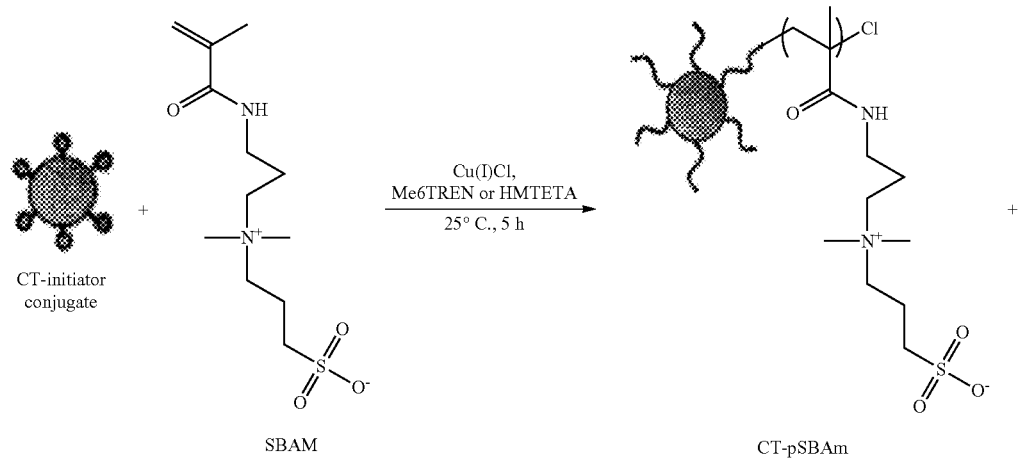

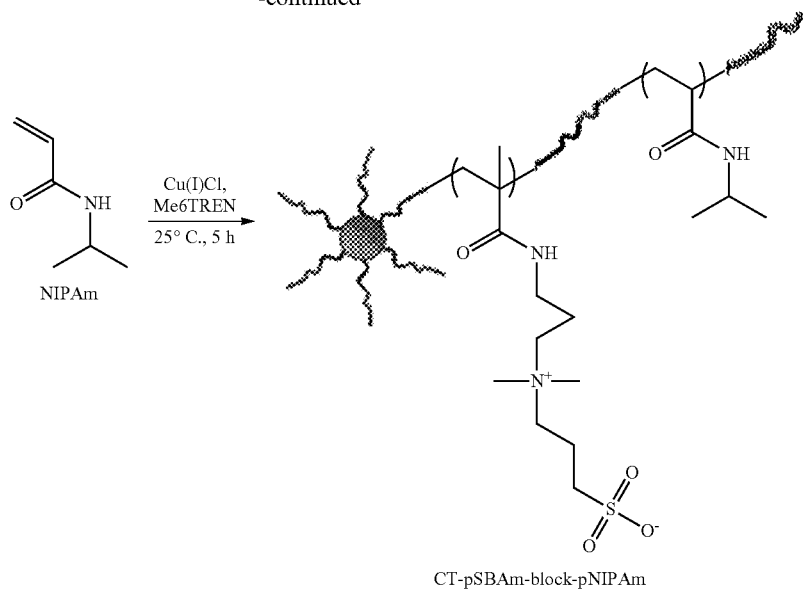

CT-pSBAm-block-pNIPAm

Following synthesis, initiator molecule (194 mg, 0.7 mmol) and CT (500 mg, 0.02 mmol protein, 0.32 mmol primary amine) were dissolved in 0.1 M sodium phosphate buffer (pH 8.0). The solution was stirred at 4° C. for 4 hours, and then dialyzed against deionized water, using dialysis tubing with a molecular weight cut off of 15 kDa, for 24 hours at 4° C. and then lyophilized.

Surface Initiated ATRP from CT-Initiator

To synthesize CT-pSBAm-block-pNIPAm conjugates, first the CT-NHS-Cl functionalized initiator conjugate (50 mg, 0.029 mmol initiator) and SBAm [335 mg (1.2 mmol), 525 mg (1.8 mmol), 701 mg (2.4 mmol)] were dissolved in 0.1 M sodium phosphate buffer (20 mL, pH 6.0) with 35 mg NaCl (30 mM). In a separate flask, Me6TREN (33 µL, 0.12 mmol) was dissolved in deionized water (5 mL) and bubbled with argon for 10 min. Cu(I)Cl (17 mg, 0.12 mmol) was added to the Me6TREN solution and Argon was bubbled for an additional 50 minutes prior to addition of the copper catalyst solution to the monomer solution. After combining the two solutions, the reaction mixture was stirred for 5 h at 25° C. until the reaction was stopped by exposing the solution to air. Lastly, the solution was purified using dialysis tubing with a molecular weight cutoff (MwCO) of 25 kDa for 48 hours against deionized water at 4° C. and then lyophilized.

Following initial synthesis of CT-pSBAm conjugates of different chain lengths, pNIPAm was grown from CT-pSBAm using chain extension to yield CT-pSBAm-block-pNIPAm conjugates. CT-pSBAm conjugates [200 mg of CT-35 (0.02 mmol initiator), 280 mg of CT-50 (0.02 mmol initiator), 350 mg of CT-90 (0.01 mmol initiator)] and NIPAm [108 mg (0.96 mmol), 163 mg (1.44 mmol), 135 mg (1.2 mmol)] were dissolved in 0.1 M sodium phosphate buffer (20 mL, pH 6.0) with 35 mg NaCl (30 mM) and bubbled with argon. In a separate flask Me6TREN [10.7 µL (0.05 mmol), 10.7 µL (0.05 mmol), 6.4 µL (0.03 mmol)] was dissolved in deionized water (5 mL) and bubbled with Argon for 10 min. Cu(I)Cl (4 mg (0.04 mmol), 4 mg (0.04 mmol), 2.4 mg (0.03 mmol)) was added to the Me6TREN solution and argon was bubbled for an additional 50 minutes. The Me6TREN/CuCl solution was quickly transferred to the CT-pSBAm/NIPAm solution and reaction was allowed to proceed for 5 h at 25° C. The reaction was stopped by quenching with air and the reaction mixture was purified using dialysis tubing with MwCO 25 kDa for 48 h against deionized water at 4° C., and then lyophilized.

UCST Cloud Point Curves for CT-pSBAm Conjugates

CT-pSBAm conjugates (CT-50-closed diamond, CT-75-closed circle, CT-100-closed square) were dissolved in 0.1 M phosphate buffer (pH 8.0) at 3 mg/mL. Samples were placed in quartz cuvette and were cooled from 35° C. or 25° C. to 5° C. at 0.5° C./min. Absorbance at 490 nm (solution turbidity) for each CT-pSBAm conjugate was measured in increments of 1° C. UCST phase transition for CT-pSBAm conjugates was dependent on polymer molecular weight. Phase transitions were quicker and absolute absorbance measurements after phase transition were higher for CT-pSBAm conjugates compared to CT-pSBAM-b/ock-pNIPAm conjugates. (FIG. 27)

Method to Determine $M_n$ of Second Block pNIPAm

Due to the contrasting size of pNIPAm and pSBAm (pSBAm monomer unit is much larger than that of pNIPAm), there was not an appropriate standard for GPC analysis. Thus, $M_w$ and $M_n$ for pSBAm-block-pNIPAm polymers could not be calculated using GPC techniques. Instead of GPC, $M_n$ values for chain extended second block pNIPAm was determined using relative ratios of peaks in NMR spectra. $M_n$ for each of the second block pNIPAm segments were estimated using the NMR spectra of diblock polymers cleaved from chymotrypsin (FIGS. 29, 30, 31). To do this, the relative intensity from peak c (3.8-4.0 ppm), corresponding to one proton in the pNIPAm block was compared with the broad signal complex from 0.8-2.3 ppm (signals a+b+d+e+f+g+h) corresponding to 18 total protons in both the pNIPAm and pSBAm blocks. From these ratios, the $M_n$ of the pNIPAm block was calculated when comparing to the for pSBAm calculated from GPC analysis.

Polymer Cleavage from CT Surface

Both pSBAm and pSBAm-block-pNIPAm were cleaved from the surface of CT-polymer conjugates using acid hydrolysis. CT-pSBAm conjugates were incubated (15 mg/mL) in 6N HCl at 110° C. under vacuum for 24 hours.

CT-pSBAm-block-pNIPAm (20 mg/mL) conjugates were incubated in 4.5N p-toluene sulfonic acid at 80° C. under vacuum for 72 hours. Following incubation, cleaved polymers were isolated from CT using dialysis tubing (MwCO 1K Da) for 48 hours and then lyophilized.

Characterization of Cleaved Polymers

Number and weight average molecular weights ($M_n$ and $M_w$) and the polydispersity index ($M_w/M_n$) were estimated by gel permeation chromatography (GPC) for pSBAm polymers cleaved from CT. Analysis was conducted on a Water 2695 Series with a data processor, using 80/20 mixture of 0.1 M sodium phosphate buffer (pH 9.0) and acetonitrile with 0.01 volume % $NaN_3$ as an eluent at a flow rate 1 mL/min, with detection by a refractive index (RI) detector. Polystyrene sulfonate standards were used for calibration. $M_n$ was calculated for pSBAm-block-pNIPAm cleaved from CT by quantitatively comparing NMR peaks (integration of peaks) of copolymer to cleaved first block pSBAm NMR spectra.

LCST/UCST Determination

CT-pSBAm-block-pNIPAm conjugates (2-3 mg polymer/mL) were dissolved in 0.1 M phosphate buffer (pH 8.0) in quartz cuvette. Conjugates were cooled from 25° C. to 1° C. and then heated up to 40° C. at ±0.5° C./min. The absorbance at 490 nm was measured in 1° C. increments and LCST/UCST temperature was calculated from the inflection point in the cloud point curves.

CT and CT Conjugate Biocatalytic Activity

N-succinyl-L-Ala-L-Ala-L-Pro-L-Phe-p-nitroanilide was used as a substrate for enzyme bioactivity assays. In a cuvette, 0.1 M sodium phosphate buffer (2820-2970 µL, pH 8.0), substrate (0-150 µL, 6 mg/mL in DMSO (0-500 µM)), and enzyme (30 µL, 0.1 mg enzyme/mL 0.1 M pH 8.0 sodium phosphate buffer (0.04 µM)) were mixed. The rate of the hydrolysis was determined by recording the increase in absorbance at 412 nm for the first 30 seconds after mixing. $K_M$ and $k_{cat}$ values were calculated using EnzFitter software when plotting substrate concentration versus initial hydrolysis velocity.

Thermal Stability

Native CT and CT-conjugates (40 µM) were dissolved in 0.1 M sodium phosphate buffer (pH 8.0) and incubated in a water bath in 50 µL aliquots at 37° C. At specified time points, aliquots were removed and diluted to 4 µM using 0.1 M sodium phosphate buffer (pH 8.0). Residual activity, measured in 0.1 M sodium phosphate buffer (pH 8.0) at 25° C., was calculated as the ratio of activity remaining relative to the activity at time zero. Substrate (Suc-AAPF-pNA) concentration was kept constant at 288 µM for each sample and time point. Native CT and conjugate activities were measured in duplicate at each time point.

In Vitro Gastric Acid Stability

Native CT and CT-conjugates were incubated at 4 µM in 167 mM HCl at 37° C. in 50 µL aliquots. Aliquots were removed at specified time points and residual activity was measured at 25° C. in 0.1 M sodium phosphate buffer (pH 8.0) with Suc-AAPF-pNA as substrate (288 µM). Each time point was measured in duplicate and residual activity was calculated as the ratio of activity remaining from time zero.

Stability to Pepsin Degradation

Native CT and CT-conjugates (4 µM) were incubated in 167 mM HCl with 16 nM pepsin at 37° C. in 50 µL aliquots. Samples were retrieved at specified time points and residual activity was measured in 0.1 M sodium phosphate buffer (pH 8.0) at 25° C. with Suc-AAPF-pNA as substrate (288 µM). Each time point was measured in duplicate and residual activity was calculated as the ratio of activity remaining from time zero. As a control, pepsin (16 nM) bioactivity towards Suc-AAPF-pNA was measured at pH 8.0 and no product formation was observed.

Size Measurements During 167 mM HCl (pH 1) Incubation

CT conjugates (4 µM) and native CT (29 µM) passed through a 0.2 µM cellulose filter were incubated in 167 mM HCl at 37° C. in 1 mL aliquots. Aliquots were removed from incubation at each specified time point. Hydrodynamic diameter was then determined using a Malvern zetasizer nano-ZS at 25° C. Intensity PSD measurements, averaged over five sample runs at each time point, were used to calculate hydrodynamic diameter ($D_h$).

Results and Discussion

Conjugate Synthesis and Polymer Characterization

As described above, separate CT-pDMAPS and CT-pNIPAm conjugates with temperature responsiveness were synthesized by "grafting from" a water soluble bromine functionalized ATRP initiator coupled to chymotrypsin (CT-Br). In this study, a similar water soluble initiating molecule (Ini-Cl), functionalized with chlorine rather than bromine, was conjugated to chymotrypsin to yield the chymotrypsin ATRP macroinitiator (CT-Cl) (Scheme IV). Similar to Ini-Br, the Ini-Cl molecule was functionalized with an NHS-ester to react with primary amines on surface lysines and the N-terminus of CT. Following synthesis of the CT-Cl macroinitiator, pSBAm was first grown from the surface of CT with three different molecular weights, yielding three conjugates with UCST behavior (CT-35, CT-50, CT-90). From GPC chromatograms (not shown), it was determined no residual free chymotrypsin was left after first block synthesis. The synthesis of CT-pNIPAm-block-pSBAm conjugates was explored, but sequential ATRP reactions in this order were not possible without optimization. After purification of CT-pSBAm conjugates, chain extension with pNIPAm was completed to yield three CT-pSBAm-block-pNIPAm conjugates with three different molecular weights that showed both UCST and LCST behavior (CT-35/39, CT-50/67, CT-90/100). The nomenclature used for each of the conjugates corresponds to degree of polymerization of each conjugate based on GPC and NMR analysis of cleaved polymers (not shown). The use of Ini-Cl/Cu(I)Cl, the addition of NaCl to the polymerization solution, and short polymerization time helped to lower the PDI of polymers grown from the surface of CT in this study (Table 15).

TABLE 15

Molecular weight and hydrodynamic diameter of CT-pSBAm-block-pNIPAm conjugates

| Sample | Cleaved Polymer | | CT Conjugate MW | | Size ($D_h$) [nm] |
| --- | --- | --- | --- | --- | --- |
| | $M_n$ | PDI ($M_w/M_n$) | BCA | GPC/NMR | |
| CT-pSBAm$_{35}$ | 10.2 kDa | 1.59 | 173 kDa | 171 kDa | 24.2 ± 2.5 |
| CT-pSBAm$_{50}$ | 15.7 kDa | 1.43 | 248 kDa | 248 kDa | 22.7 ± 1.9 |
| CT-pSBAm$_{90}$ | 26.2 kDa | 1.86 | 362 kDa | 395 kDa | 23.3 ± 1.0 |
| CT-pSBAm$_{35}$-block-pNIPAm$_{39}$ | 14.6 kDa | — | 302 kDa | 232 kDa | 46.1 ± 4.5 |
| CT-pSBAm$_{50}$-block-pNIPAm$_{67}$ | 23.3 kDa | — | 427 kDa | 354 kDa | 47.6 ± 8.7 |
| CT-pSBAm$_{90}$-block-pNIPAm$_{100}$ | 37.5 kDa | — | 475 kDa | 553 kDa | 64.1 ± 4.5 |

It is also likely the reaction conditions reduced growing chain termination and ligand/catalyst degradation, which conserved the living nature of the polymer chain to allow chain extension of pNIPAm from CT-pSBAm (Simakova, A.; Averick, S. E.; Konkolewicz, D.; Matyjaszewski, K. *Macromolecules* 2012, 45, 6371; Tsarevsky, N. V.; Pintauer, T.; Matyjaszewski, K. *Macromolecules* 2004, 37, 9768.). Gas chromatogram results (not shown) indicated that minimal amounts (<10%) of CT-pSBAm conjugates did remain after chain extension indicating some chain termination might have occurred during first block synthesis.

Phase Transition Temperatures of CT-pSPAm-block-pNIPAm Conjugates

Figure 10:
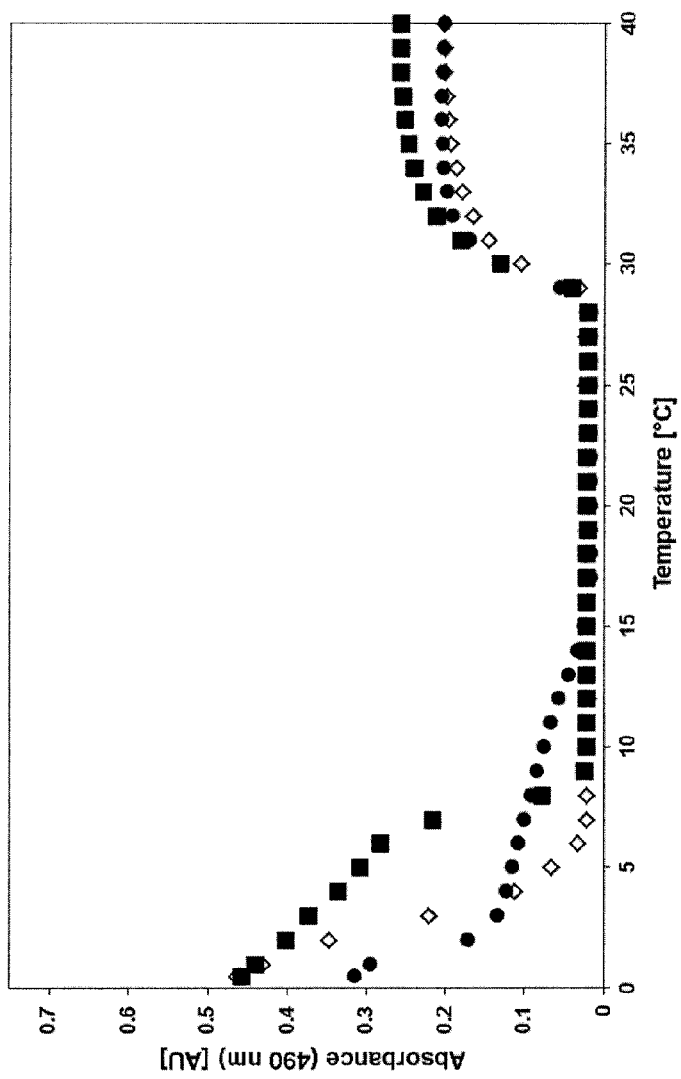
FIG. 10 shows cloud point curves for CT-pSBAm-block-pNIPAm conjugates (CT-35/39-open diamond, CT-50/67-closed square, CT-90/100-closed circle). Each conjugate (3 mg/mL) was incubated in 0.1 M sodium phosphate buffer (pH=8.0), heated/cooled at ±0.5° C./min, and absorbance at 490 nm was recorded.
Figure 11:
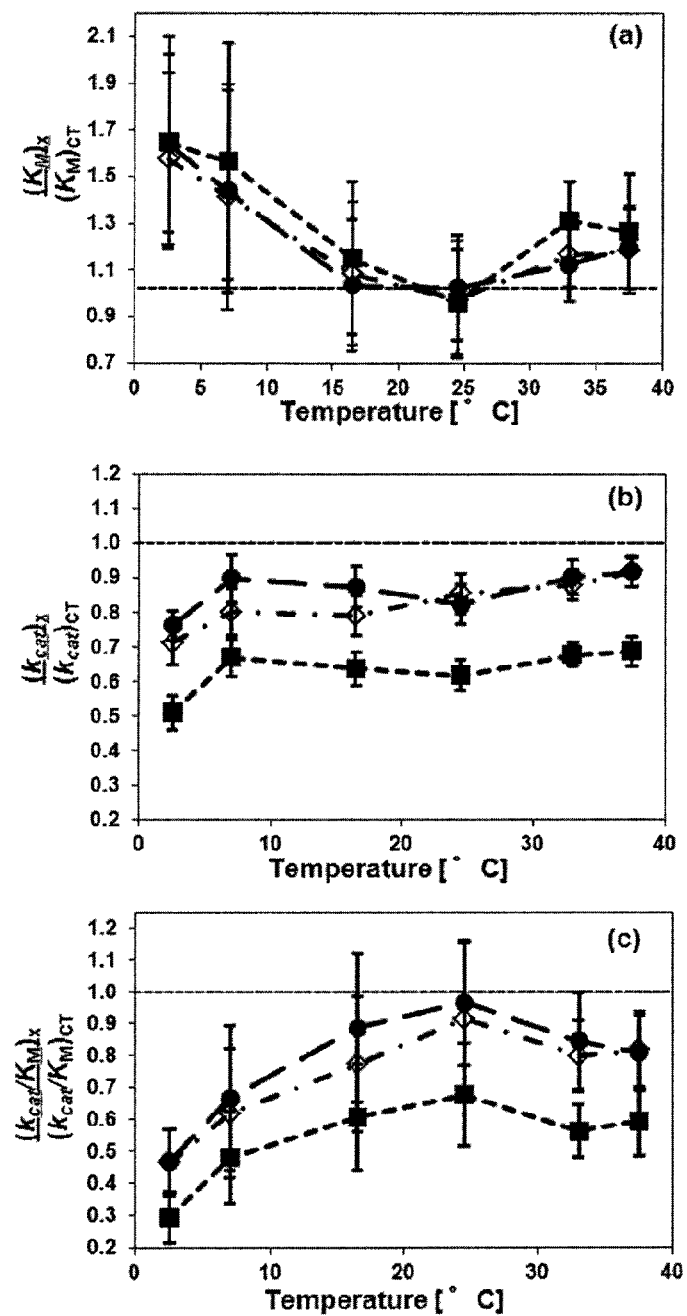
FIGS. 11A-C illustrate Temperature dependence of enzyme (A) specificity ($K_M$), (B) activity ($k_{cat}$), and (C) productivity ($k_{cat}/K_M$) relative values in the hydrolysis of NS-AAPF-pNA by CT-pSBAm-block-pNIPAm conjugates (CT-35/39-open diamond/dash-dot line, CT-50/67-closed circle/large dash line, CT-90/100-closed square/short dash line) relative to native CT in 0.1 M sodium phosphate buffer (pH=8.0). Values for native chymotrypsin at increasing temperature (2.5° C., 7° C., 16.5° C., 24.5° C., 33° C., and 37.5° C.) are as follows: $K_M$(μM)-30±5.1, 29±6.9, 37±8.6, 51±8.7, 57±5.0, 59±6.9; $k_{cat}$(sec$^{-1}$)-8.9±0.4, 9.7±0.5, 16±0.9, 25±1.3, 36±1.3, 47±1.7; $k_{cat}/K_M$(sec$^{-1}$/μM)-0.33±0.06, 0.34±0.09, 0.43±0.10, 0.50±0.1, 0.80±0.1. CT-pSBAm-block-pNIPAm kinetic values are shown in SI Table 1.

UCST and LCST temperatures for each of the three molecular weight conjugates (CT-35/39, CT-50/67, and CT-90/100) were determined by measuring solution turbidity (absorbance at 490 nm) at temperatures from 0-40° C. Each of the conjugates displayed both LCST and UCST behavior, but the specific phase change temperature was dependent upon the polymer chain length (FIG. 10). Each of the conjugates showed LCST behavior at 29° C. in 0.1 M phosphate buffer (pH=8.0). As previously reported, linear pNIPAm LCST is independent of molecular weight when the molecular weight is not ultra-high[23], so this result was not unexpected. LCST phase transition at 29° C. was slightly lower than previously reported LCST values for pNIPAm, but the lowered value is consistent with LCST behavior in salt buffers compared to deionized water (Zhang, Y.; Furyk, S.; Sagle, L. B.; Cho, Y.; Bergbreiter, D. E.; Cremer, P. S. *J. Phys. Chem. C* 2007, 111, 8916). The LCST also agreed well with the LCST temperature determined in Experimental Section II for CT-pNIPAm conjugates. The turbidity of these solutions (0.2-0.25 AU) was also lower than CT-pNIPAM conjugates. When above the LCST, pNIPAm polymer chains are insoluble in aqueous solutions and thermodynamically prefer to minimize interactions with water. Thus, as each of the conjugates reached temperatures above 29° C., the pNIPAm component of the bioconjugate collapsed. For free pNIPAm in solution, large aggregates form; greatly increasing turbidity. However, for CT-pSBAm-block-pNIPAm, hydrophilic CT and pSBAm components, even at temperatures above the LCST, prevented more extreme aggregation, which caused turbidity measurements above the LCST to plateau at a lower value than free pNIPAM or CT-pNIPAm conjugates.

When comparing CT-pSBAm-block-pNIPAm cloud point curves with CT-pSBAm curves (FIG. 28), it was clear that the pNIPAm block influenced the UCST behavior of the pSBAm component in the final bioconjugate. A lower temperature was required for the CT-pSBAm-b/ock-pNIPAm conjugates to show collapsed, insoluble behavior compared with CT-pSBAm conjugates. At low temperature, pSBAm was hydrophobic, but the pNIPAm and CT components of the conjugate were still hydrophilic and influenced the overall behavior of the conjugate. In addition to polymer collapse, aggregation of hydrophobic pSBAm polymer blocks between different CT molecules contributed to the turbidity seen in the cloud point curves. The pNIPAm block, located on the outside of the CT conjugates, likely sterically hindered pSBAm association between CT molecules, which could lower the transition temperature onset as determined by cloud point curves. The UCST behavior for CT-90/100, the longest chain conjugate, did not show a sharp increase in absorbance at a specific temperature. Instead, turbidity measurements for CT-90/100 increased linearly when decreasing temperature from 15-3° C., and ultimately showed a sharp increase in absorbance around 2° C. As with CT-35/39 and CT-50/67, it was hypothesized that this effect was due to steric hindrance of pNIPAm and the hydrophilicity of CT and pNIPAm at this temperature range. However, the long chain length of pNIPAm on the outside of CT-90/100 prevented a sharp increase in turbidity at the temperature where insolubility was initially observed.

Effect of Double Shelled Polymer-Based Protein Engineering on CT Bioactivity

CT conjugate kinetics were examined at a variety of temperatures (2.5° C., 7° C., 16.5° C., 24.5° C., 33° C., and 37.5° C.) to determine the effect of polymer UCST and LCST phase transitions and molecular weight on enzyme kinetics (see FIGS. 11(*a*)-(*c*) and Table 16 below).

TABLE 16

Michelis-Menten kinetics for CT and CT conjugate catalyzed hydrolysis of NS-AAPF-pNA from zero to 37.5° C.

| Sample | $K_M$ [μM] | $k_{cat}$ [$sec^{-1}$] | $k_{cat}/K_M$ [$sec^{-1}$/μM] | $(K_M) \times (K_M)_{CT}$ | $(k_{cat}) \times (k_{cat})_{CT}$ | $(k_{cat}/K_M) \times (k_{cat}/K_M)_{CT}$ |
|---|---|---|---|---|---|---|
| 2.5° C. | | | | | | |
| Native CT | 30 ± 5.1 | 8.9 ± 0.4 | 0.33 ± 0.06 | — | — | — |
| CT-35/39 | 47 ± 7.5 | 6.3 ± 0.5 | 0.14 +0.02 | 1.59 | 0.71 | 0.42 |
| CT-50/67 | 49 ± 7.7 | 6.8 ± 0.2 | 0.14 ± 0.02 | 1.65 | 0.76 | 0.42 |
| CT-90/100 | 49 ± 10 | 4.5 ± 0.4 | 0.08 ± 0.02 | 1.66 | 0.51 | 0.24 |
| 7° C. | | | | | | |
| Native CT | 29 ± 6.9 | 9.7 ± 0.5 | 0.34 ± 0.09 | — | — | — |
| CT-35/39 | 41 ± 9.6 | 7.8 ± 0.5 | 0.19 ± 0.05 | 1.42 | 0.80 | 0.57 |
| CT-50/67 | 41 ± 7.3 | 8.7 ± 0.5 | 0.21 ± 0.06 | 1.45 | 0.90 | 0.62 |
| CT-90/100 | 45 ± 9.6 | 6.5 ± 0.4 | 0.15 ± 0.03 | 1.58 | 0.67 | 0.43 |
| 16.5° C. | | | | | | |
| Native CT | 37 ± 8.6 | 16 ± 0.9 | 0.43 ± 0.10 | — | — | — |
| CT-35/39 | 41 ± 6.8 | 13 ± 0.5 | 0.31 ± 0.05 | 1.09 | 0.79 | 0.72 |
| CT-50/67 | 39 ± 5.6 | 14 ± 0.5 | 0.36 ± 0.05 | 1.04 | 0.87 | 0.84 |
| CT-90/100 | 43 ± 7.1 | 10 ± 0.5 | 0.24 ± 0.04 | 1.16 | 0.64 | 0.56 |
| 24.5° C. | | | | | | |
| Native CT | 51 ± 8.7 | 25 ± 1.3 | 0.50 ± 0.10 | — | — | — |
| CT-35/39 | 50 ± 10 | 22 ± 0.9 | 0.43 ± 0.08 | 0.98 | 0.86 | 0.87 |
| CT-50/67 | 53 ± 7.3 | 21 ± 0.9 | 0.41 ± 0.06 | 1.03 | 0.82 | 0.92 |
| CT-90/100 | 50 ± 7.8 | 16 ± 0.7 | 0.31 ± 0.05 | 0.97 | 0.62 | 0.63 |
| 33° C. | | | | | | |
| Native CT | 57 ± 5.0 | 36 ± 1.3 | 0.64 ± 0.08 | — | — | — |
| CT-35/39 | 67 ± 5.3 | 32 ± 0.9 | 0.47 ± 0.04 | 1.18 | 0.88 | 0.75 |
| CT-50/67 | 65 ± 7.2 | 33 ± 1.4 | 0.51 ± 0.07 | 1.14 | 0.90 | 0.80 |
| CT-90/100 | 75 ± 6.9 | 25 ± 0.7 | 0.33 ± 0.03 | 1.32 | 0.68 | 0.51 |
| 37.5° C. | | | | | | |
| Native CT | 59 ± 6.9 | 47 ± 1.7 | 0.80 ± 0.10 | — | — | — |
| CT-35/39 | 71 ± 6.7 | 43 ± 1.4 | 0.61 ± 0.06 | 1.19 | 0.92 | 0.77 |
| CT-50/67 | 71 ± 6.3 | 43 ± 1.3 | 0.61 ± 0.06 | 1.21 | 0.92 | 0.76 |
| CT-90/100 | 75 ± 11 | 32 ± 1.6 | 0.43 ± 0.07 | 1.27 | 0.69 | 0.54 |

The rate of hydrolysis of N-succinyl-L-Ala-L-Ala-L-Pro-L-Phe-p-nitroanilide by CT and CT conjugates in 0.1 M sodium phosphate buffer (pH 8.0) was used to determine the impact of doubled-shelled PBPE on CT bioactivity. CT conjugate bioactivity was temperature dependent after conjugation of pSBAm-block-pNIPAm. Relative $K_M$ and $k_{cat}$ values for CT-35/39, CT-50/67, and CT-90/100 were all modified after conjugation, but only relative $K_M$ values were dependent upon temperature. For CT-35/39 and CT-50/67, relative $k_{cat}$ values were between 0.8 and 0.9 at each of the tested temperatures. Relative $k_{cat}$ values for CT-90/100 were slightly lower than CT-35/39 and CT-50/67 conjugates, but similarly, enzyme activity was conserved and was independent of temperature. In experiments described in Experimental Section III herein relating to the methods of the invention described herein, long chain polymer conjugation has decreased $k_{cat}$ values due to limited structural flexibility, which likely contributed to decreased $k_{cat}$ values in this study as well (Rodríguez-Martínez, J. A.; Solá, R. J.; Castillo, B.; Cintrón-Colón, H. R.; Rivera-Rivera, I.; Barletta, G.; Griebenow, K. *Biotechnol. Bioeng.* 2008, 101, 1142).

While $k_{cat}$ values were independent of temperature, relative $K_M$ values for CT-pSBAm-block-pNIPAm bioconjugates showed a significant dependence to both low and high temperatures. At 25° C., each of the conjugates calculated $K_M$ values were similar to native CT. However, at temperatures both higher and lower than 25° C., relative $K_M$ values increased significantly for each of the conjugates. At low temperatures the increase in relative $K_M$ was more extreme than the $K_M$ increase at high temperature. At assay temperatures below 25° C., relative $K_M$ values increased until reaching a maximum (~1.6-1.7 for each of the conjugates) at 2.5° C. At 40° C., relative $K_M$ for each of the conjugates was approximately 1.2, indicating lower substrate infinity for the conjugates compared to native CT at this temperature. For CT-35/39 and CT-50/67, relative $K_M$ values were slightly lower at 35° C. than $K_M$ values at 40° C. CT-90/100 relative $K_M$ values were only slightly higher at 35° C. than 40° C.

Figure 12:
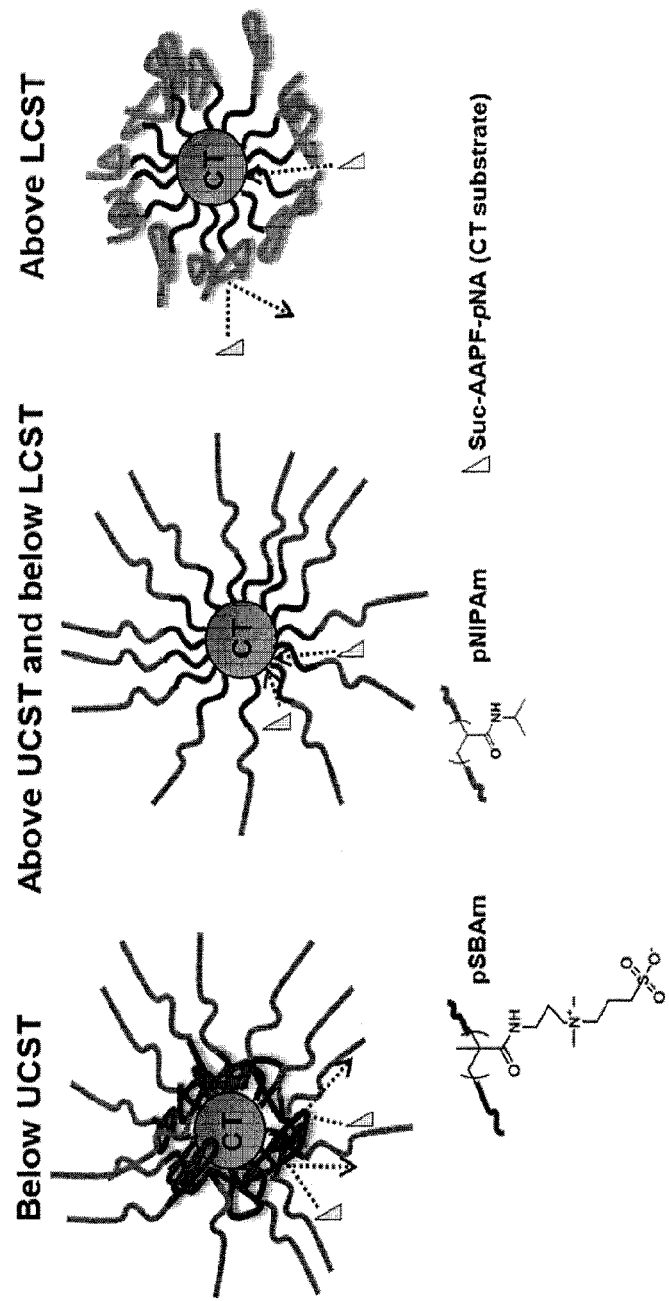
FIG. 12 is a schematic of the hypothesized effect of pSBAm and pNIPAm polymer collapse on substrate affinity ($K_M$). At 25° C., both pSBAm and pNIPAm were in their extended conformation and allowed Suc-AAPF-pNA access to CT active site. At temperatures below pSBAm UCST and above pNIPAm LCST, polymer collapse inhibited access to the active site for Suc-AAPF-pNA due to steric blocking. At temperatures below pSBAm UCST, this effect is hypothesized to be more pronounced than at temperatures above pNIPAm LCST, because the pSBAm block was closer to the enzyme core than the pNIPAm block.

It was hypothesized that the increase in $K_M$ values at both high and low temperature was a result of restricted access to the active site for the model substrate due to steric hindrance caused by polymer collapse during both UCST and LCST phase transitions. FIG. 12 shows the hypothesis of how polymer collapse impacted substrate access to the enzyme active site, drawn to the scale of each polymer block approximated from dynamic light scattering data (Table 15 of this Section). At temperatures above 29° C., as determined by cloud point curves, the pNIPAm block of the polymer was collapsed upon itself to minimize its interaction with water. As the pNIPAm polymers collapsed, a more compact shell existed compared to pNIPAm orientation at 25° C., which likely restricted the model substrate's ability to reach the active site. At low temperature, it was hypothesized that the increase in relative $K_M$ was also due to steric hindrance from polymer collapse, except the pSBAm polymer block collapsed at low temperature rather than pNIPAm. As seen from the cloud point curves, CT-90/100 UCST polymer collapse began at 16° C., so it was not surprising to see the highest relative $K_M$ increase of the three conjugates at this assay temperature. As temperature decreased, the UCST induced polymer collapse appeared to continue to increase as evidenced by the increase in turbidity measurements in cloud points curves. The increase seen in relative $K_M$ values at lower temperatures was most likely due to this increase in polymer collapse and dehydration. Once the substrate reached the active site, the rate of the reaction was similar at each temperature measured, as shown by the lack of dependence of relative $k_{cat}$ values on temperature.

Chain length of the polymers did not appear to have a large effect on the relative $K_M$ values. While CT-90/100 conjugates did have slightly higher relative $K_M$ values than CT-35/39 and CT-50/67, a clear trend between the three conjugates was not noticeable. It is also important to notice the difference in relative $K_M$ values with respect to the location of the collapsed polymer in the conjugate. Since the pSBAm block was synthesized first, this polymer was closer to the core of the conjugate, while the pNIPAm block was on the outside of the conjugates. It was surmised that, due to this orientation, polymer collapse and turbidity increases were seen at both high and low temperatures, but the specific geometry of the overall collapsed conjugate was different. It was hypothesized that the pSBAm collapse showed higher relative $K_M$ values due to its location closer to the core of the conjugate (closest to the active site). In addition, while pNIPAm collapse at high temperature also induced increased relative $K_M$ values, the effect was not as pronounced due to its location on the outside of the conjugate.

Relative productivity ($k_{cat}/K_M$) ratios for each of the CT-pSBAm-block-pNIPAm conjugates were also dependent upon temperature. Relative productivity values for CT-35/39 and CT-50/67 were similar to native CT at 25° C., and CT-90/100 was slightly reduced due to lower $k_{cat}$ values at this temperature. For each temperature tested other than 25° C., $k_{cat}/K_M$ values were decreased, mostly as a result of the increased relative $K_M$ values seen after phase transitions. The largest decrease in productivity ratios was seen at 2.5° C., where relative $K_M$ values were the highest and a slight decrease in $k_{cat}$ values was seen for each conjugate.

CT Conjugate Stability

Figure 13:
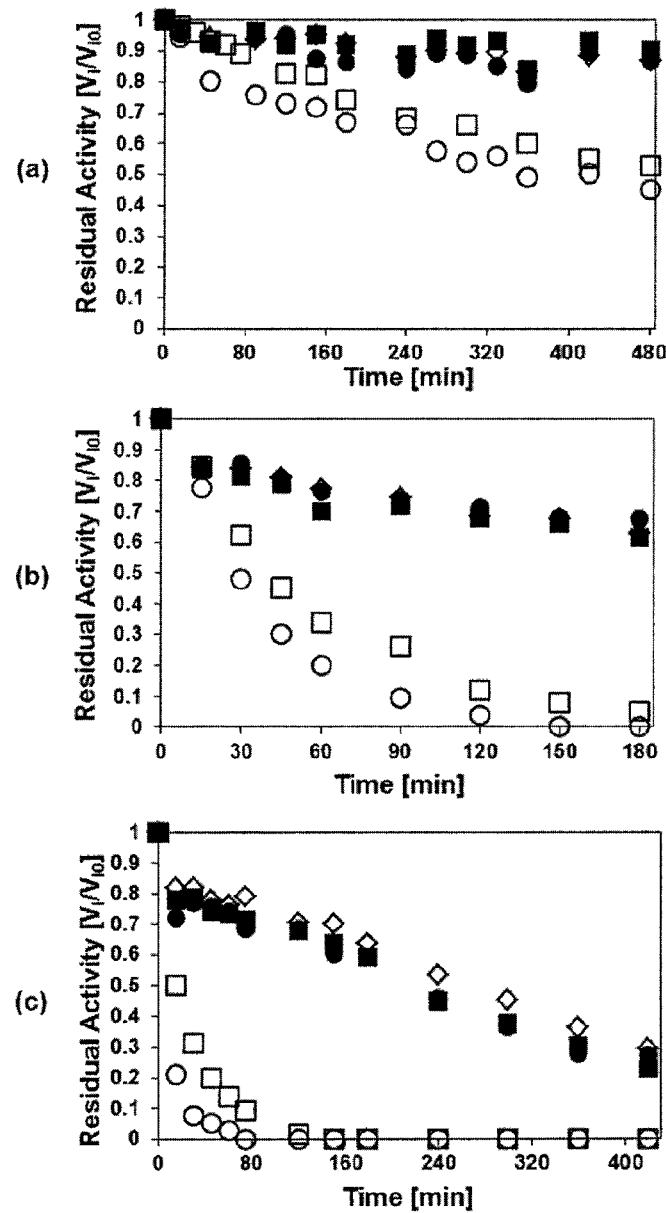
FIGS. 13A-C provide graphs showing the rate of irreversible inactivation for CT-pSBAm-block-pNIPAm conjugates (CT-35/39-open diamonds, CT-50/67-closed squares, and CT-90/100-closed circles), native CT (open circles), and native CT with pSBAm-block-pNIPAm in solution (open squares) at 37° C. in (a) 0.1 M sodium phosphate buffer (pH=8.0), (b) 167 mM HCl (pH=1), and (c) 167 mM HCl with 19 nM pepsin. Residual activity was calculated as the activity remaining from t=0. All assays were conducted at 25° C.
Figure 14:
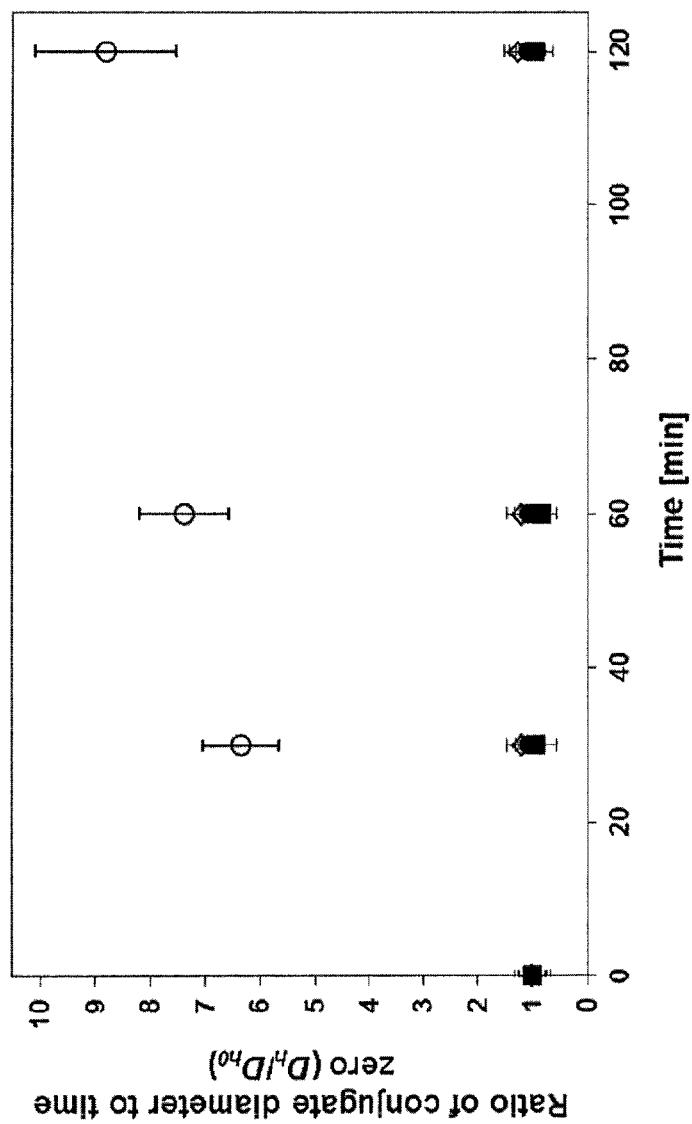
FIG. 14 illustrates the dependence of native and CT conjugate hydrodynamic diameter during incubation in 167 mM HCl (pH 1) at 37° C. Size values are presented as ratios of each samples size at time zero. Increased hydrodynamic diameter ($D_h$) indicates protein unfolding. $D_h$ values at time zero were: native CT (open circle)-6.3±0.5 nm, CT-35/39 (open diamond)-51±9.7 nm, CT-50/67 (closed circle)-63±14 nm, CT-90/100 (closed square)-72±12 nm.

The thermal stability, pH stability, and protease degradation stability conditions of the CT-pSBAm-block-pNIPAm conjugates were explored in detail. CT conjugates of each molecular weight had higher stability than native CT to (a) incubation at 37° C., (b) incubation in 167 mM HCl (pH 1), and (c) incubation with pepsin (FIG. 13). Specifically, maintaining stability of proteins as they are subjected to extreme pH and protease degradation (as would be seen in the GI tract) is a large challenge. Most studies on oral peptide delivery technologies have focused on transport through the intestinal membrane (Reineke, J.; Cho, D. Y.; Dingle, Y. L.; Cheifetz, P.; Laulicht, B.; Lavin, D.; Furtado, S.; Mathiowitz, E. *J. Controlled Release* 2013, 170, 477) or pharmacokinetics/biodistribution, (Xu, Q.; Boylan, N. J.; Cai, S.; Miao, B.; Patel, H.; Hanes, J. *J. Controlled Release* 2013, 170, 279.) but do not examine stability of the protein in the GI tract.

Stability at Ambient Temperature and Neutral pH

CT conjugates lost only 10% of their activity after 8 hours incubation at 40 µM in 0.1 M sodium phosphate buffer (pH 8.0), while native CT lost half of its activity over the same time period (FIG. 13*a*). At 37° C. and pH 8, CT was still active and, consequently, one contributor to irreversible inactivation at this temperature and pH was autolysis. As a protease, CT hydrolyzes peptide bonds to break down proteins, and CT inactivates itself due to self-digestion of unfolded CT in solution. As a result of the polymer density around CT conjugates, steric hindrance limited CT molecules access to each other, decreasing autolysis and increasing stability. Previously, PEGylation of protein molecules has been shown to reduce structural dynamics (Rodríguez-Martinez, J. A.; Solá, R. J.; Castillo, 13.; Cintrón-Colón, H. R.; Rivera-Rivera, I.; Barletta, G.; Griebenow, K. *Biotechnol. Bioeng.* 2008, 101, 1142), and charged polymers have increased the stability of CT after conjugation due to charge effects (Keefe, A. J.; Jiang, S. Y. *Nat. Chem.* 2012, 4, 60; Baldwin, R. L. *Biophys. J.* 1996, 71, 2056). Increased stability imparted by CT-pSBAm-block-pNIPAM conjugates was likely due to a combination of both effects as the pSBAm block contained protein stabilizing ions and pNIPAm chemical structure was similar to PEG.

Stability at Extremes of pH

Interestingly, CT conjugates also showed increased to stability to low pH. Native CT and CT conjugates were incubated in 167 mM HCl (pH 1) at 37° C. for 3 hours to mimic gastric acid. In vivo, gastric acid promotes unfolding of proteins to increase access of pepsin to cleavable amino acid sequences, Each of the CT conjugates maintained at least 60% of activity after incubation in 167 mM HCl for 3 hours, compared to complete activity loss for native CT after the same time period (FIG. 13*b*). In 167 mM HCl, (pH 1), native CT unfolds due to disruption of hydrogen bonding. One can imagine two mechanisms through which PBPE might stabilize CT to such a dramatic extent. First, the polymer stabilized the structure of CT, which reduced unfolding. Second, as some CT molecules unfolded, access to cleavage sites by autolysis was restricted by steric hindrance of polymer as seen at 37° C. and pH 8.0. However, at pH 1 the enzyme should be inactive, and autolysis cannot contribute to CT inactivation. The activity of CT and CT-conjugates was measured at pH 1.0 and no product formation was observed with large excess of substrate (data not shown). Thus, protein unfolding without autolysis was the main mechanism for CT inactivation in 167 mM HCl. To further develop the mechanistic understanding, dynamic light scattering was used to examine native CT and CT conjugate hydrodynamic diameter during incubation at pH 1 (FIG. 14). After 2 hours, the hydrodynamic diameter ($D_h$) for native CT increased 9-fold, while CT conjugate size increased less than 20%. After incubation at low pH in 167 mM HCl, hydrogen bonding and other forces that maintain globular structure of proteins were likely disrupted for native CT. The disruption of forces led to protein unfolding, causing the protein to transition from a globular conformation to a more linear structure, which increased $D_h$ measurements for native CT. While very small increases in $D_h$ were seen for CT conjugates, the magnitude was much lower due to the structural stabilization provided by the conjugated polymers that maintained CT globular structure. In a control experiment, it was also shown that free pSBAm-block-pNIPAm in solution had a small effect on structural stabilization of native CT at pH 1 (FIG. 13*b*). It was surmised that structure stabilizing ions in the pSBAm block (ammonium and sulfonate) of the free polymer slightly increased solution total salt concentration to stabilize CT tertiary structure. While stabilization was increased a small amount with free polymer in solution, polymer conjugation to the protein was superior for structural stabilization due to the high local concentration of the polymer near the enzyme surface.

The stability of CT conjugates to pepsin degradation in acid was next explored. CT bioconjugates were stable to pepsin incubation at 37° C. in 167 mM HCl (FIG. 13*c*). Native CT lost all activity after only 75 minutes, while CT conjugates maintained approximately 70% residual activity after the same time period and still had 30% of initial activity after 7 hours. For pepsin to cleave proteins through hydrolysis, pepsin molecules must be able to access the specifically favored amino acid sequence on chymotrypsin. Due to the high density polymer shell around CT-pSBAm-block-pNIPAm conjugates of each molecular weight, access for pepsin was inhibited. In addition, due to the low pH conditions, unfolding occurred for native CT, which increased access for pepsin degradation.

Multi-stimuli responsive polymers represent a new class of protein-polymer conjugates that can respond to two stimuli through separate responses from each block. Temperature responsive polymer conjugation has previously been utilized for separation purposes (Chen, J. P.; Hoffman, A. S. *Biomaterials* 1990, 11, 631.), and the conjugate described herein could be used for separations at both high and low temperature, which could be driven by the need to conserve energy required for high temperatures or prevent protein denaturation. In addition, protein-polymer conjugates with both UCST and LCST behavior show that other protein-polymer conjugates with separate blocks of pH and temperature responsive behavior can be synthesized as well. UCST and LCST are just two of the multitude of responsive properties that can be incorporated into block copolymers. A dual block conjugate with pH and temperature sensitive behavior could be used to treat cancer by responding to lower pH (Callahan, D. J.; Liu, W. E.; Li, X. H.; Dreher, M. R.; Hassouneh, W.; Kim, M.; Marszalek, P.; Chilkoti, A. *Nano Lett.* 2012, 12, 2165) that is common in a tumor mass, as well as responding to targeted external heating at the tumor. (McDaniel, J. R.; Dewhirst, M. W.; Chilkoti, A. *Int. J. Hyperthermia.* 2013, 29, 501) The dual block system lets scientists design the pH and temperature triggers more specifically than could be done for a single polymer block with dual responsiveness. Lastly, this approach shows that smart polymer functionality can be implemented with equal success on the inside or outside block of a diblock polymer shell.

Conclusion

In Experimental Series IV, dual temperature responsive CT-pSBAm-block-pNIPAm conjugates with different polymer chain lengths and molecular weights were synthesized using a "grafting from" approach with two successive ATRP reactions. Chain extension of the pNIPAm block from homopolymer CT-pSBAm conjugate was utilized to grow the block copolymer from the surface of CT. From cloud point curves, it has been shown that CT-35/39, CT-50/67, CT-90/100 conjugates each had both UCST and LCST phase transition behavior. LCST behavior was due to the pNIPAm polymer block and was not affected by chain length. The pSBAm polymer block imparted UCST behavior on each of the conjugates, but the specific transition temperature and behavior was dependent upon the chain length of attached polymers. Polymer conjugation to CT affected both enzyme turnover number ($k_{cat}$) and substrate affinity ($K_M$) values, but only relative $K_M$ values were dependent upon temperature. Relative productivity ($k_{cat}/K_M$) ratios were also dependent upon temperature, mostly due to observed effects of relative $K_M$ values. Stability of CT-pSBAm-block-pNIPAm conjugates was dramatically higher than native CT. Without being bound by theory, it is believed that the polymers reduced protein unfolding and restricted access of proteases thru steric hindrance for a variety of incubation conditions including thermal, low pH, and protease degradation. The present invention has been used to generates a protein that would be expected to survive passage through the stomach. A variety of proteins may be modified with responsive polymers that first protect enzymes from this environment and then respond to stimuli as needed.

All publications, including associated Supplemental materials, are hereby incorporated by reference in their entirety as if each individual publication was specifically and individually incorporated by reference. In case of conflict, the present application, including any definitions herein, will control.

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

The invention claimed is:

1. A method comprising:

in an aqueous solution, immobilizing an active ester-functionalized amide-containing controlled radical polymerization CRP initiator comprised of the structure

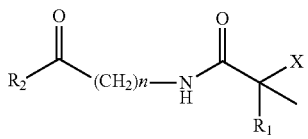

wherein X is a halogen or a chain transfer agent;
$R_1$ is H or alkyl;
$R_2$ is an active ester moiety; and
n is an integer from 1 to 6,
on each of a plurality of amino binding sites on a protein surface to form a protein-initiator conjugate;
isolating the protein-initiator conjugate;
mixing a first group of monomers having one or more desired properties with the protein-initiator conjugate;
polymerizing the monomers from the protein-initiator conjugate to grow a polymer under controlled radical polymerization conditions to form a protein-polymer conjugate; and,
isolating the protein-polymer conjugate.

2. The method recited in claim 1 wherein immobilizing the initiator comprises mixing protein and the initiator in a buffer at a pH of about 8 to 9 and stirring for a period of time sufficient to allow the formation of covalent bonds between the initiator and at least a majority of the amino binding sites.

3. The method recited in claim 1 wherein isolating the protein-initiator conjugate comprises removing unreacted and unattached compounds from the solution.

4. The method recited in claim 3 wherein removing unreacted and unattached compounds from the solution comprises passing the solution through a dialysis membrane.

5. The method recited in claim 4 further comprises lyophilizing the protein-polymer conjugate.

6. The method recited in claim 1 wherein the controlled radical polymerization conditions comprise conditions for one of an atom radical polymerization (ATRP) procedure or a reversible-addition fragmentation chain transfer (RAFT) procedure.

7. The method recited in claim 1 wherein the polymerization is an ATRP procedure and the method further comprises:
mixing the protein-initiator conjugate and monomers in a buffer and removing oxygen from the mixture;
separately adding a deoxygenated ligand to an aqueous copper catalyst solution;
transferring the copper-ligand catalyst solution to the protein-initiator conjugate and monomer mixture; and
stirring at 4-25° C. for a sufficient time to allow polymerization.

8. The method recited in claim 7 wherein removing oxygen from the protein-initiator conjugate and monomer mixture comprises bubbling Ar or $N_2$ through the mixture.

9. The method recited in claim 7 wherein isolating the protein-polymer conjugate comprises passing the mixture through a dialysis membrane and refrigerating for a period of time sufficient to remove copper-ligand catalyst and unreacted monomer.

10. The method recited in claim 7 wherein X in the initiator structure is one of Br, Cl, or F.

11. The method recited in claim 7 wherein the initiator comprises N-2-bromo-2-methylpropanoyl-β-alanine N'-oxysuccinimide ester.

12. The method recited in claim 7 wherein the initiator comprises N-2-chloro-propanoyl-β-alanine N'-oxysuccinimide ester.

13. The method recited in claim 1 wherein the active ester moiety is selected from the group consisting of N-oxysuccinimde ester, nitrophenyl ester, pentahalophenyl ester wherein the halogen is F or Cl, 1-oxybenzotriazole ester, and 2-oxy-4,6-dimethyloxy-1,3,5-triazine ester.

14. The method recited in claim 1 wherein the polymerization comprises a RAFT procedure and the chain transfer agent comprises a thiocarbonylthio agent.

15. The method recited in claim 1 wherein the protein comprises an enzyme and the initiator covalently binds to a majority of the binding sites on the surface of the enzyme.

16. The method recited in claim 1 wherein the protein comprises an enzyme and the initiator covalently binds to at least 85% of the binding sites on the surface of the enzyme.

17. The method recited in claim 1 wherein the enzyme is selected from the group consisting of chymotrypsin, lysozyme, β-Galactosidase, carbonic anhydrase, glucose oxidase, laccase, and acetylcholinesterase.

18. The method recited in claim 1 wherein the polymer comprises a stimuli responsive polymer that responds to at least one stimulus.

19. The method recited in claim 18 wherein the stimulus is one or both of pH and temperature.

20. The method recited in claim 1 wherein the protein-polymer conjugate comprises chymotrypsin modified through high density attachment of thermo-responsive polymers.

21. The method recited in claim 1 wherein the protein-polymer conjugate formed from the controlled radical polymerization comprises a protein-homopolymer conjugate of different polymer chain lengths and the method further comprises:
following the polymerization of the first group of monomers from the protein-initiator conjugate, mixing a second group of monomers having one or more desirable properties with the protein-homopolymer conjugate under controlled radical polymerization conditions to form a block copolymer.

22. The method recited in claim 21 wherein the block copolymer comprises a dual temperature responsive enzyme-pSBAm-block-pNIPAm conjugate having different polymer chain lengths and molecular weights.

23. The method recited in claim 1 wherein the protein comprises an enzyme and the surface charge of the enzyme is modified by growing cationic pQA from multiple sites on the surface of enzyme.

24. The method recited in claim 1 wherein the polymers grown from the plurality of surface amino sites of the protein core form a high density cationic polymer shell around the protein core.

25. The method recited in claim 1 wherein the chain length of the polymers is controlled by adjusting the molar concentration of the first group of monomers added to the protein initiator conjugate to a desired amount.

26. A macroinitiator comprising:
a water soluble active ester-functionalized amide-containing controlled radical polymerization initiator comprised of the structure

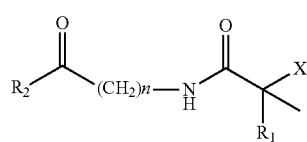

wherein X is a halogen or a chain transfer agent;
$R_1$ is H or alkyl;
$R_2$ is an active ester moiety; and
n is an integer from 1 to 6, covalently bound to each of a plurality of surface amino acid residues on a protein.

27. The macroinitiator recited in claim 26 wherein the initiator further covalently binds to the N-terminus of the protein.

28. The macroinitiator recited in claim 26 wherein the initiator is N-2-bromo-2-methylpropanoyl-β-alanine N'-oxysuccinimide ester.

29. The macroinitiator recited in claim 26 wherein the initiator is N-2-chloro-propanoyl-β-alanine N'-oxysuccinimide ester.

30. The macroinitiator recited in claim 26 wherein the active ester moiety is selected from the group consisting of N-oxysuccinimde ester, nitrophenyl ester, pentahalophenyl ester, 1-oxybenzotriazole ester, and 2-oxy-4,6-dimethyloxy-1,3,5-triazine ester.

31. The macroinitiator recited in claim 26 wherein the initiator binds to at least 85% of the lysine residues on the protein.

32. A composition comprising:
a water soluble active ester-functionalized amide-containing controlled radical polymerization initiator comprised of the structure

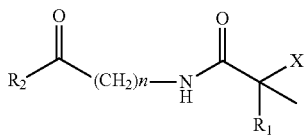

wherein X is a halogen or a chain transfer agent;
$R_1$ is H or alkyl;
$R_2$ is an active ester moiety; and
n is an integer from 1 to 6,
covalently bound to each of a plurality of surface amino acid residues on a protein to form a densely modified protein-polymer conjugate with a density of polymer chains per unit surface area greater than one polymer chain per 10 $nm^2$ of protein surface area.

33. The composition recited in claim 32 wherein the protein comprises an enzyme core having surface amino residues covalently bound at each of at least 85% of the surface amino residues to the initiator.

34. The composition recited in claim 32 wherein the densely modified protein-polymer conjugate comprises a stimuli responsive polymer.

35. The composition recited in claim 32 wherein the densely modified protein-polymer conjugate comprises an enzyme selected from the group consisting of chymotrypsin, lysozyme, β-galactosidase, carbonic anhydrase, glucose oxidase, laccase, and acetylcholinesterase.

36. The composition recited in claim 32 wherein each polymer chain comprises a block copolymer.

37. The composition recited in claim 32 wherein the polymer chains form a shell around the protein.

38. The composition recited in claim 32 wherein the polymer chains comprise polypeptides with free amine groups.

39. The composition recited in claim 32 wherein the polymer chains are formed from monomers polymerizable by ATRP.

* * * * *